US006406867B1

(12) United States Patent
Yu et al.

(10) Patent No.: US 6,406,867 B1
(45) Date of Patent: Jun. 18, 2002

(54) ANTIBODY TO HUMAN ENDOKINE ALPHA AND METHODS OF USE

(75) Inventors: Guo-Liang Yu, Berkeley, CA (US); Jian Ni, Rockville; Craig A. Rosen, Laytonsville, both of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/513,584

(22) Filed: Feb. 25, 2000

Related U.S. Application Data

(60) Continuation-in-part of application No. 09/345,790, filed on Jul. 1, 1999, which is a division of application No. 08/912,227, filed on Aug. 15, 1997, now Pat. No. 5,998,171.
(60) Provisional application No. 60/136,788, filed on May 28, 1999, provisional application No. 60/122,099, filed on Feb. 26, 1999, and provisional application No. 60/024,058, filed on Aug. 16, 1996.

(51) Int. Cl.[7] .......................... C07K 16/22; G01N 33/53; G01N 33/567

(52) U.S. Cl. ................. 435/7.2; 530/387.1; 530/387.9; 530/388.1; 530/388.15; 530/388.24; 530/389.2; 424/130.1; 424/139.1; 424/141.1; 424/142.1; 424/158.1

(58) Field of Search .......................... 530/387.1, 387.9, 530/388.1, 388.15, 388.24, 389.2; 424/130.1, 139.1, 141.1, 142.1, 145.1, 158.1; 435/7.1, 7.2

(56) References Cited

U.S. PATENT DOCUMENTS

| 5,288,852 A | 2/1994 | Yamada et al. ............. 530/351 |
| 5,998,171 A | 12/1999 | Yu et al. .................... 435/69.5 |

FOREIGN PATENT DOCUMENTS

| EP | 0 212 489 | 3/1987 |
| EP | 0 218 868 | 4/1987 |
| EP | 0 288 088 | 10/1988 |
| WO | WO 98/07880 | 2/1998 |

OTHER PUBLICATIONS

Aggarwal, B. B. and K. Natarajan, "Tumor necrosis factors: Developments during the last decade," *Eur. Cytokine Netw.* 7:93–124 (Apr.–Jun. 1996).
Beutler, B. et al., "Passive Immunization Against Cachectin/Tumor Necrosis Factor Protects Mice from Lethal Effect of Endotoxin," *Science* 229:869–871 (1985).
Bringman, T. S. and B. B. Aggarwal, "Monoclonal Antibodies to Human Tumor Necrosis Factors Alpha and Beta: Application for Affinity Purification, Immunoassays, and as Structural Probes," *Hybridoma* 6:489–507 (1987).
Elliott, M. J. and R. N. Maini, "Anti–cytokine therapy in rheumatoid arthritis," *Ballière's Clin. Rheum.* 9:633–652 (Nov. 1995).
Feldmann, M. et al., "TNFα Is an Effective Therapeutic Target for Rheumatoid Arthritis," *Ann. N.Y. Acad. Sci.* 766:272–278 (Nov. 1995).
Fendly, B. M. et al., "Murine Monoclonal Antibodies Defining Neutralizing Epitopes on Tumor Necrosis Factor,"*Hybridoma* 6:359–370 (1987).
Gruss, H–J. and S. K. Dower, "Tumor Necrosis Factor Ligand Superfamily: Involvement in the Pathology of Malignant Lymphomas," *Blood* 85:3378–3404 (Jun. 1995).
Hinshaw, L. B. et al., "Survival of Primates in $LD_{100}$ Septic Shock Following Therapy With Antibody to Tumor Necrosis Factor (TNFα)," *Circ. Shock* 30:279–292 (1990).
Hirai, M. et al., "Production and characterization of monoclonal antibodies to human tumor necrosis factor," *J. Immunol. Methods* 96:57–62 (1987).
Kriegler, M. et al., "A Novel Form of TNF/Cachectin Is a Cell Surface Cytotoxic Transmembrane Protein: Ramifications for the Complex Physiology of TNF," *Cell* 53:45–53 (1988).
Liang, C–M. et al., "Production and Characterization of Monoclonal Antibodies Against Recombinant Human Tumor Necrosis Factor/Cachectin," *Biochem. Biophys. Res. Comm.* 137:847–854 (1986).
Mathison, J. C. et al., "Participation of Tumor Necrosis Factor in the Mediation of Gram Negative Bacterial Lipopolysaccharide–induced Injury in Rabbits," *J. Clin. Invest.* 81:1925–1937 (1988).
Meager, A. et al., "Preparation and Characterization of Monoclonal Antibodies Directed Against Antigenic Determinants of Recombinant Human Tumour Necrosis Factor (rTNF)," *Hybridoma* 6:305–311 (1987).
Möller, A. et al., "Monoclonal Antibodies to Human Tumor Necrosis Factor α:In Vitro and In Vivo Application," *Cytokine* 2:162–169 (1990).
Opal, S. M. et al., "Efficacy of a Monoclonal Antibody Directed against Tumor Necrosis Factor in Protecting Neutropenic Rats from Lethal Infection with *Pseudomonas aeruginosa*," *J. Infect. Dis.* 161:1148–1152 (1990).
Shimamoto, Y. et al., "Monoclonal antibodies against human recombinant tumor necrosis factor: prevention of endotoxic shock," *Immunol. Letters* 17:311–318 (1988).

(List continued on next page.)

*Primary Examiner*—Prema Mertz
(74) *Attorney, Agent, or Firm*—Sterne, Kessler, Goldstein & Fox P.L.L.C.

(57) ABSTRACT

The present invention concerns a novel member of the tumor necrosis factor (TNF) family of cytokines. In particular, isolated nucleic acid molecules are provided encoding the endokine alpha protein. Endokine alpha polypeptides are also provided, as are vectors, host cells and recombinant methods for producing the same. Antibodies and antibody fragments which specifically bind the polypeptides of the invention are also provided, as well as methods for detecting the polypeptides of the invention using said antibodies and antibody fragments. Also provided are diagnostic and therapeutic methods concerning TNF family-related disorders.

56 Claims, 4 Drawing Sheets

OTHER PUBLICATIONS

Silva, A. T. et al., "Prophylactic and Therapeutic Effects of a Monoclonal Antibody to Tumor Necrosis Factor–α in Experimental Gram–Negative Shock," *J. Infect. Dis.* 162:421–427 (1990).

Smith, R. A. and C. Baglioni, "The Active Form of Tumor Necrosis Factor Is a Trimer," *J. Biol. Chem.* 262:6951–6954 (1987).

Tracey, K. J. et al., "Anti–cachetin/TNF monoclonal antibodies prevent septic shock during lethal bacteraemia," *Nature* 330:662–664 (1987).

Tracey, K. J. and A. Cerami, "Tumor necrosis factor: An updated review of its biology," *Crit. Care Med.* 21:S415–S422 (1993).

van der Poll, T. and S. F. Lowry, "Tumor Necrosis Factor in Sepsis: Mediator of Multiple Organ Failure or Essential Part of Host Defense?," *Shock* 3:1–12 (Jan. 1995).

Wherry, J. C. et al., "Tumor necrosis factor and the therapeutic potential of anti–tumor necrosis factor antibodies," *Crit. Care Med.* 21:S436–S440 (1993).

Database EST–STN on MASPAR search, WashU–Merck EST Project, (St. Louis, Mo, USA), No. R38487, from Hillier et al., "yf60c04.s1 *Homo sapiens* cDNA clone 26749 3'," (May 1995).

Database EST–STN on MASPAR search, WashU–Merck EST Project, (St. Louis, MO., USA) No. R1403, from Hillier et al., "yf94c12.s1 *Homo sapiens* cDNA clone 30225 3'," (May 1995).

Database EST–STN on MASPAR search, GenBank at National Library of Medicine, No. s78214, from Miki et al., "Disruption of the APC gene by retrotransposal insertion of L1 sequence in a colon cancer," *Cancer Research* 52:643–645 (1992).

EMBL/GENBANK/DDBJ Data Banks, No. P41086, EMBL U02603, from Wood, "Putative Succinate Dehydrogenase 15 KD Hydrophobic Protein" (Feb. 1995).

International Search Report for Application No. PCT/US96/13282, mailed Nov. 1996.

```
  1 GTTTTCCACAGCTCTCATTTCTCCAAAAATGTGTTTGAGCCACTTGGAAA
 51 ATATGCCTTTAAGCCATTCAAGAACTCAAGGAGCTCAGAGATCATCCTGG
    M  P  L  S  H  S  R  T  Q  G  A  Q  R  S  S  W

101 AAGCTGTGGCTCTTTTGCTCAATAGTTATGTTGCTATTTCTTTGCTCCTT
    K  L  W  L  F  C  S  I  V  M  L  L  F  L  C  S  F

151 CAGTTGGCTAATCTTTATTTTCTCCAATTAGAGACTGCTAAGGAGCCCT
    S  W  L  I  F  I  F  L  Q  L  E  T  A  K  E  P  C

201 GTATGGCTAAGTTTGGACCATTACCCTCAAAATGGCAAATGGCATCTTCT
    M  A  K  F  G  P  L  P  S  K  W  Q  M  A  S  S

251 GAACCTCCTTGCGTGAATAAGGTGTCTGACTGGAAGCTGGAGATACTTCA
    E  P  P  C  V  N  K  V  S  D  W  K  L  E  I  L  Q

301 GAATGGCTTATATTTAATTTATGGCCAAGTGGCTCCCAATGCAAACTACA
    N  G  L  Y  L  I  Y  G  Q  V  A  P  N  A  N  Y  N

351 ATGATGTAGCTCCTTTTGAGGTGCGGCTGTATAAAAACAAAGACATGATA
    D  V  A  P  F  E  V  R  L  Y  K  N  K  D  M  I

401 CAAACTCTAACAAACAAATCTAAAATCCAAAATGTAGGAGGGACTTATGA
    Q  T  L  T  N  K  S  K  I  Q  N  V  G  G  T  Y  E

451 ATTGCATGTTGGGGACACCATAGACTTGATATTCAACTCTGAGCATCAGG
    L  H  V  G  D  T  I  D  L  I  F  N  S  E  H  Q  V

501 TTCTAAAAAATAATACCTACTGGGGTATCATTTTACTAGCAAATCCCCAA
    L  K  N  N  T  Y  W  G  I  I  L  L  A  N  P  Q

551 TTCATCTCCTAGAGACTTGATTTGATCTCCTCATTCCCTTCAGCACATGT
    F  I  S
```

FIG. 1A

```
601   AGAGGTGCCAGTGGGTGGATTGGAGGGAGAAGATATTCAATTTCTAGAGT
651   TTGTCTGTCTACAAAAATCAACACAAACAGAACTCCTCTGCACGTGAATT
701   TTCATCTATCATGCCTATCTGAAAGAGACTCAGGGGAAAAGCCAAAGACT
751   TTTGGTTGGATCTGCAGAGATACTTCATTAATCCATGATAAAACAAATAT
801   GGATGACAGAGGACATGTGCTTTTCAAAGAATCTTTATCTAATTCTTGAA
851   TTCATGAGTGGAAAAATGGAGTTCTATTCCCATGGAAGATTTACCTGGTA
901   TGCAAAAGGATCTGGGGCAGTAGCCTGGCTTTGTTCTCATATTCTTGGG
951   CTGCTGTAATTCATTCTTCTCATACTCCCATCTTCTGAGACCCTCCCAAT
1001  AAAAAGTAGACTGATAGGATGGCCACAGATATGCCTACCATACCCTACTT
1051  TAGATATGGTGGTGTTAGAAGATAAAGAACAATCTGAGAACTATTGGAAT
1101  AGAGGTACAAGTGGCATAAAATGGAATGTACGCTATCTGGAAATTTCTCT
1151  TGGTTTTATCTTCCTCAGGATGCAGGGTGCTTTAAAAAGCCTTATCAAAG
1201  GAGTCATTCCGAACCCTCACGTAGAGCTTTGTGAGAACTTACTGTTGGTG
1251  TGTGTGTCTAAACATTGCTAATTGTAAAGAAAGAGTAACCATTAGTAATC
1301  ATTAGGTTTAACCCCAGAATGGTATTATCATTACTGGATTATGTCATGTA
1351  ATGATTTAGTATTTTTAGCTAGCTTTCCACAGTTTGCAAAGTGCTTTCGT
1401  AAAACAGTTAGCAATTCTATGAAGTTAATTGGGCAGGCATTTGGGGGAAA
1451  ATTTTAGTGATGAGAATGTGATAGCATAGCATAGCCAACTTTCCTCAACT
1501  CATAGGACAAGTGACTACAAGAGGCAATGGGTAGTCCCCTGCATTGCACT
1551  GTCTCAGCTTTAGAATTGTTATTTCTGCTATCGTGTTATAAGACTCTAAA
1601  ACTTAGCGAATTCACTTTTCAGGAAGCATATTCCCCTTTAGCCCAAGGTG
1651  AGCAGAGTGAAGCTACAACAGATCTTTCCTTTACCAGCACACTTTTTTTT
1701  TTTTCCTGCCTGAATCAGGGAGATCCAGGATGCTGTTCAGGCCTTATCCC
1751  AACCAAATTCCCCTCTTCACTTTGCAGGGCCCATCTTAGTCAAATGTGCT
1801  AACTTCTAAAATAATAAATAGCACTAATTCAAAAAAAAAAAAAAAAAAA
```

FIG. 1B

```
  1  MS-TESMIRDVELAEEALPKKTG----------GPQGSRRCLFL-----SLFSFLIV--A  TNFalpha
  1  MT-PPERL--------FLPRVCG----------TT------LHL-----LLLGLLMLLP  TNFbeta
  1  MPLSHSRT--------QGAQRSSVKLWLFCSIVML------LFLCSFSWIEIFLQL--E  Endokine alpha 43  GATTLFCLLHFGVIGPQREESPRDLSLISPLAQAVRSSSRT----PSDKPVAHVVANPQA  TNFalpha
 31  GAQGL-------------------PGVGLTPSAAQTARQHPKMHLAHSTLKPAAHLIGDPSK  TNFbeta
 45  TAKE----------------PCMAKFGPLP----SKWQM----ASSEP------PCV  Endokine alpha 99  EGQLQWLNRRANALLANGVELRDNQLVVPSEGLYLIYSQVLFKGQG----CPSTHVLLTH  TNFalpha
 74  QNSLLWRANTDRAFLQDGFSLSNNSLLVPTSGIYFVYSQVVFSGKAYSPKAPSSPLYLAH  TNFbeta
 72  NKVSDWKLEILQ----------------NGLYLIYGQV---------APNAN-----  Endokine alpha 155  TISRIAVSYQTKVNLLSAIKSPCQRETPEGAEAKPWYEPIYLGGVFQLEKGDRLSAEINR  TNFalpha
134  EVQLFSSQYPFHVPLLSSQK------MVYPGLQEPWLHSMYHGAAFQLTQGDQLSTHTDG  TNFbeta
 99  ----YNDVAPFEVRLYKNKD------MIQTLTNKSKIQNV--GGTYELHVGDTIDLIFNS  Endokine alpha 215  PDYLDFAESGQVYFGIIAL                                          TNFalpha
188  IPHLVLS-PSTVFFGAFAL                                          TNFbeta
147  -EHGVLK-NNT-YWGIILLANPQFIS                                   Endokine alpha
```

FIG.2

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1849 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 53..559

(xi) SEQUENCE DESCRIPTION: SEQ ID NO:1:

```
GTTTTCCACA GCTCTCATTT CTCCAAAAAT GTGTTTGAGC CACTTGGAAA A T ATG            55
                                                         Met
                                                          1

CCT TTA AGC CAT TCA AGA ACT CAA GGA GCT C AG AGA TCA TCC TGG AAG         103
Pro Leu Ser His Ser Arg Thr Gln Gly Ala G ln Arg Ser Ser Trp Lys
            5                  10                  15

CTG TGG CTC TTT TGC TCA ATA GTT ATG TTG C TA TTT CTT TGC TCC TTC         151
Leu Trp Leu Phe Cys Ser Ile Val Met Leu L eu Phe Leu Cys Ser Phe
        20                  25                  30

AGT TGG CTA ATC TTT ATT TTT CTC CAA TTA G AG ACT GCT AAG GAG CCC         199
Ser Trp Leu Ile Phe Ile Phe Leu Gln Leu G lu Thr Ala Lys Glu Pro
    35                  40                  45

TGT ATG GCT AAG TTT GGA CCA TTA CCC TCA A AA TGG CAA ATG GCA TCT         247
Cys Met Ala Lys Phe Gly Pro Leu Pro Ser L ys Trp Gln Met Ala Ser
50                  55                  60                  65

TCT GAA CCT CCT TGC GTG AAT AAG GTG TCT G AC TGG AAG CTG GAG ATA         295
Ser Glu Pro Pro Cys Val Asn Lys Val Ser A sp Trp Lys Leu Glu Ile
                70                  75                  80

CTT CAG AAT GGC TTA TAT TTA ATT TAT GGC C AA GTG GCT CCC AAT GCA         343
Leu Gln Asn Gly Leu Tyr Leu Ile Tyr Gly G ln Val Ala Pro Asn Ala
            85                  90                  95

AAC TAC AAT GAT GTA GCT CCT TTT GAG GTG C GG CTG TAT AAA AAC AAA         391
Asn Tyr Asn Asp Val Ala Pro Phe Glu Val A rg Leu Tyr Lys Asn Lys
            100                 105                 110

GAC ATG ATA CAA ACT CTA ACA AAC AAA TCT A AA ATC CAA AAT GTA GGA         439
Asp Met Ile Gln Thr Leu Thr Asn Lys Ser L ys Ile Gln Asn Val Gly
        115                 120                 125

GGG ACT TAT GAA TTG CAT GTT GGG GAC ACC A TA GAC TTG ATA TTC AAC         487
Gly Thr Tyr Glu Leu His Val Gly Asp Thr I le Asp Leu Ile Phe Asn
```

-continued

```
                130                 135                 140                 145
TCT GAG CAT CAG GTT CTA AAA AAT AAT ACC T AC TGG GGT ATC ATT TTA           535
Ser Glu His Gln Val Leu Lys Asn Asn Thr T yr Trp Gly Ile Ile Leu
                    150                 155                 160

CTA GCA AAT CCC CAA TTC ATC TCC TAGAGACTTG A TTTGATCTC CTCATTCCCT          589
Leu Ala Asn Pro Gln Phe Ile Ser
                165

TCAGCACATG TAGAGGTGCC AGTGGGTGGA TTGGAGGGAG AAGATATTCA A TTTCTAGAG         649

TTTGTCTGTC TACAAAAATC AACACAAACA GAACTCCTCT GCACGTGAAT T TTCATCTAT         709

CATGCCTATC TGAAAGAGAC TCAGGGGAAA AGCCAAAGAC TTTTGGTTGG A TCTGCAGAG         769

ATACTTCATT AATCCATGAT AAAACAAATA TGGATGACAG AGGACATGTG C TTTTCAAAG         829

AATCTTTATC TAATTCTTGA ATTCATGAGT GGAAAAATGG AGTTCTATTC C CATGGAAGA         889

TTTACCTGGT ATGCAAAAAG GATCTGGGGC AGTAGCCTGG CTTTGTTCTC A TATTCTTGG         949

GCTGCTGTAA TTCATTCTTC TCATACTCCC ATCTTCTGAG ACCCTCCCAA T AAAAAGTAG        1009

ACTGATAGGA TGGCCACAGA TATGCCTACC ATACCCTACT TTAGATATGG T GGTGTTAGA        1069

AGATAAAGAA CAATCTGAGA ACTATTGGAA TAGAGGTACA AGTGGCATAA A ATGGAATGT        1129

ACGCTATCTG GAAATTTCTC TTGGTTTTAT CTTCCTCAGG ATGCAGGGTG C TTTAAAAAG        1189

CCTTATCAAA GGAGTCATTC CGAACCCTCA CGTAGAGCTT TGTGAGAACT T ACTGTTGGT        1249

GTGTGTGTCT AAACATTGCT AATTGTAAAG AAAGAGTAAC CATTAGTAAT C ATTAGGTTT        1309

AACCCCAGAA TGGTATTATC ATTACTGGAT TATGTCATGT AATGATTTAG T ATTTTTAGC        1369

TAGCTTTCCA CAGTTTGCAA AGTGCTTTCG TAAAACAGTT AGCAATTCTA T GAAGTTAAT        1429

TGGGCAGGCA TTTGGGGGAA AATTTTAGTG ATGAGAATGT GATAGCATAG C ATAGCCAAC        1489

TTTCCTCAAC TCATAGGACA AGTGACTACA AGAGGCAATG GGTAGTCCCC T GCATTGCAC        1549

TGTCTCAGCT TTAGAATTGT TATTTCTGCT ATCGTGTTAT AAGACTCTAA A ACTTAGCGA        1609

ATTCACTTTT CAGGAAGCAT ATTCCCCTTT AGCCCAAGGT GAGCAGAGTG A AGCTACAAC        1669

AGATCTTTCC TTTACCAGCA CACTTTTTTT TTTTTCCTGC CTGAATCAGG G AGATCCAGG        1729

ATGCTGTTCA GGCCTTATCC CAACCAAATT CCCCTCTTCA CTTTGCAGGG C CCATCTTAG        1789

TCAAATGTGC TAACTTCTAA AATAATAAAT AGCACTAATT CAAAAAAAAA A AAAAAAAA         1849
```

(2) INFORMATION FOR SEQ ID NO:2:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Leu Ser His Ser Arg Thr Gln Gly A la Gln Arg Ser Ser Trp
 1               5                  10                  15

Lys Leu Trp Leu Phe Cys Ser Ile Val Met L eu Leu Phe Leu Cys Ser
            20                  25                  30

Phe Ser Trp Leu Ile Phe Ile Phe Leu Gln L eu Glu Thr Ala Lys Glu
        35                  40                  45

Pro Cys Met Ala Lys Phe Gly Pro Leu Pro S er Lys Trp Gln Met Ala
    50                  55                  60

Ser Ser Glu Pro Pro Cys Val Asn Lys Val S er Asp Trp Lys Leu Glu
65                  70                  75                  80
```

Ile Leu Gln Asn Gly Leu Tyr Leu Ile Tyr Gly Gln Val Ala Pro Asn
                85                  90                  95

Ala Asn Tyr Asn Asp Val Ala Pro Phe Glu Val Arg Leu Tyr Lys Asn
                100                 105                 110

Lys Asp Met Ile Gln Thr Leu Thr Asn Lys Ser Lys Ile Gln Asn Val
                115                 120                 125

Gly Gly Thr Tyr Glu Leu His Val Gly Asp Thr Ile Asp Leu Ile Phe
                130                 135                 140

Asn Ser Glu His Gln Val Leu Lys Asn Asn Thr Tyr Trp Gly Ile Ile
145                 150                 155                 160

Leu Leu Ala Asn Pro Gln Phe Ile Ser
                165

(2) INFORMATION FOR SEQ ID NO:3:

(i) SEQUENCE CHARACTERISTICS:
        (A) LENGTH: 233 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
                35                  40                  45

Cys Leu Leu His Phe Gly Val Ile Gly Pro Gln Arg Glu Glu Ser Pro
                50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
                115                 120                 125

Glu Gly Leu Tyr Leu Ile Tyr Ser Gln Val Leu Phe Lys Gly Gln Gly
                130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
                210                 215                 220

Gln Val Tyr Phe Gly Ile Ile Ala Leu
225                 230

(2) INFORMATION FOR SEQ ID NO:4:

(i) SEQUENCE CHARACTERISTICS:
          (A) LENGTH: 205 amino acids
          (B) TYPE: amino acid
          (C) STRANDEDNESS: Not Relevant
          (D) TOPOLOGY: Not Relevant (ii) MOLECULE TYPE: protein (xi) SEQUENCE DESCRIPTION: SEQ ID NO:4:

Met Thr Pro Pro Glu Arg Leu Phe Leu Pro Arg Val Cys Gly Thr Thr
 1               5                  10                  15

Leu His Leu Leu Leu Leu Gly Leu Leu Leu Val Leu Leu Pro Gly Ala
             20                  25                  30

Gln Gly Leu Pro Gly Val Gly Leu Thr Pro Ser Ala Ala Gln Thr Ala
             35                  40                  45

Arg Gln His Pro Lys Met His Leu Ala His Ser Thr Leu Lys Pro Ala
         50                  55                  60

Ala His Leu Ile Gly Asp Pro Ser Lys Gln Asn Ser Leu Leu Trp Arg
 65                  70                  75                  80

Ala Asn Thr Asp Arg Ala Phe Leu Gln Asp Gly Phe Ser Leu Ser Asn
                 85                  90                  95

Asn Ser Leu Leu Val Pro Thr Ser Gly Ile Tyr Phe Val Tyr Ser Gln
                100                 105                 110

Val Val Phe Ser Gly Lys Ala Tyr Ser Pro Lys Ala Pro Ser Ser Pro
            115                 120                 125

Leu Tyr Leu Ala His Glu Val Gln Leu Phe Ser Ser Gln Tyr Pro Phe
        130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GCGCCATGGC TAAGTTTGGA CCAT                                      24

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCGAAGCTTT CAAGTCTCTA GGAGATG                                   27

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCGGATCCCG AGACTGCTAA GGAGCC                  26

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCGGATCCCT AGGAGATGAA TTGGGGATTT G             31

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GCGGGATCCG CCATCATGCC TTTAAGCCAT TC          32

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCGGATCCCT AGGAGATGAA TTGGGGATTT G             31

ANTIBODY TO HUMAN ENDOKINE ALPHA AND METHODS OF USE

CROSS-REFERENCE TO RELATED APPLICATIONS

This application claims the benefit of U.S. Provisional Application No. 60/136,788, filed May 28, 1999, which disclosure is herein incorporated by reference, and Ser. No. 60/122,099, filed Feb. 26, 1999, which disclosure is herein incorporated by reference; this application is also a continuation-in-part of U.S. application No. 09/345,790, filed Jul. 1, 1999, which disclosure is herein incorporated by reference; said Ser. No. 09/345,790 is a division of U.S. application Ser. No. 08/912,227, filed Aug. 15, 1997, U.S. Pat. No. 5,998,171, which disclosure is herein incorporated by reference; said Ser. No. 08/912,227 claims the benefit of U.S. Provisional application Ser. No. 60/024,058, filed Aug. 16, 1996, which disclosure is herein incorporated by reference.

BACKGROUND OF THE INVENTION

1. Field of the Invention

The present invention concerns a novel member of the tumor necrosis factor (TNF) family of cytokines. In particular, isolated nucleic acid molecules are provided encoding the endokine alpha protein. Endokine alpha polypeptides are also provided, as are vectors, host cells and recombinant methods for producing the same. Also provided are diagnostic and therapeutic methods concerning TNF family-related disorders.

2. Related Art

The cytokine known as tumor necrosis factor-α (TNFα; also termed cachectin) is a protein secreted primarily by monocytes and macrophages in response to endotoxin or other stimuli as a soluble homotrimer of 17 kD protein subunits (Smith, R. A. et al., *J. Biol. Chem.* 262:6951–6954 (1987)). A membrane-bound 26 kD precursor form of TNF has also been described (Kriegler, M. et al., *Cell* 53:45–53 (1988)).

Accumulating evidence indicates that TNF is a regulatory cytokine with pleiotropic biological activities. These activities include: inhibition of lipoprotein lipase synthesis ("cachectin" activity) (Beutler, B. et al., *Nature* 316:552 (1985)), activation of polymorphonuclear leukocytes (Klebanoff, S. J. et al., *J. Immunol.* 136:4220 (1986); Perussia, B., et al., *J. Immunol.* 138:765 (1987)), inhibition of cell growth or stimulation of cell growth (Vilcek, J. et al., *J. Exp. Med.* 163:632 (1986); Sugarman, B. J. et al., *Science* 230:943 (1985); Lachman, L. B. et al., *J. Immunol.* 138:2913 (1987)), cytotoxic action on certain transformed cell types (Lachman, L. B. et al., supra; Darzynkiewicz, Z. et al., *Canc. Res.* 44:83 (1984)), antiviral activity (Kohase, M. et al., *Cell* 45:659 (1986); Wong, G. H. W. et al., *Nature* 323:819 (1986)), stimulation of bone resorption (Bertolini, D. R. et al., *Nature* 319:516 (1986); Saklatvala, J., *Nature* 322:547 (1986)), stimulation of collagenase and prostaglandin E2 production (Dayer, J.-M. et al., *J. Exp. Med.* 162:2163 (1985)); and immunoregulatory actions, including activation of T cells (Yokota, S. et al., *J. Immunol.* 140:531 (1988)), B cells (Kehrl, J. H. et al., *J. Exp. Med.* 166:786 (1987)), monocytes (Philip, R. et al., *Nature* 323:86 (1986)), thymocytes (Ranges, G. E. et al., *J. Exp. Med.* 167:1472 (1988)), and stimulation of the cell-surface expression of major histocompatibility complex (MHC) class I and class II molecules (Collins, T. et al., *Proc. Natl. Acad. Sci. USA* 83:446 (1986); Pujol-Borrel, R. et al., *Nature* 326:304 (1987)).

TNF is noted for its pro-inflammatory actions which result in tissue injury, such as induction of procoagulant activity on vascular endothelial cells (Pober, J. S. et al., *J. Immunol.* 136:1680 (1986)), increased adherence of neutrophils and lymphocytes (Pober, J. S. etal., *J. Immunol.* 138:3319 (1987)), and stimulation of the release of platelet activating factor from macrophages, neutrophils and vascular endothelial cells (Camussi, G. et al., *J. Exp. Med.* 166:1390 (1987)).

Recent evidence implicates TNF in the pathogenesis of many infections (Cerami, A. et al., *Immunol. Today* 9:28 (1988)), immune disorders, neoplastic pathology, e.g., in cachexia accompanying some malignancies (Oliff, A. et al., *Cell* 50:555 (1987)), and in autoimmune pathologies and graft-versus host pathology (Piguet, P.-F. et al., *J. Exp. Med.* 166:1280 (1987)). The association of TNF with cancer and infectious pathologies is often related to the host's catabolic state. A major problem in cancer patients is weight loss, usually associated with anorexia. The extensive wasting which results is known as "cachexia" (Kern, K. A. et al. *J. Parent. Enter. Nutr.* 12:286–298 (1988)). Cachexia includes progressive weight loss, anorexia, and persistent erosion of body mass in response to a malignant growth. The cachectic state is thus associated with significant morbidity and is responsible for the majority of cancer mortality. A number of studies have suggested that TNF is an important mediator of the cachexia in cancer, infectious pathology, and in other catabolic states.

TNF is thought to play a central role in the pathophysiological consequences of Gram-negative sepsis and endotoxic shock (Michie, H. R. et al., *Br. J. Surg.* 76:670–671 (1989); Debets, J. M. H. et al., *Second Vienna Shock Forum*, p.463–466 (1989); Simpson, S. Q. et al., *Crit. Care Clin.* 5:27–47 (1989)), including fever, malaise, anorexia, and cachexia. Endotoxin is a potent monocyte/macrophage activator which stimulates production and secretion of TNF (Kombluth, S. K. et al., *J. Immunol.* 137:2585–2591 (1986)) and other cytokines. Because TNF could mimic many biological effects of endotoxin, it was concluded to be a central mediator responsible for the clinical manifestations of endotoxin-related illness. TNF and other monocyte-derived cytokines mediate the metabolic and neurohormonal responses to endotoxin (Michie, H. R. et al., *N. Eng. J. Med.* 318:1481–1486 (1988)). Endotoxin administration to human volunteers produces acute illness with flu-like symptoms including fever, tachycardia, increased metabolic rate and stress hormone release (Revhaug, A. et al., *Arch. Surg.* 123:162–170 (1988)). Elevated levels of circulating TNF have also been found in patients suffering from Gram-negative sepsis (Waage, A. et al., *Lancet* 1:355–357 (1987); Hammerle, A. F. et al., *Second Vienna Shock Forum* p. 715–718 (1989); Debets, J. M. H. et al., *Crit. Care Med.* 17:489–497 (1989); Calandra, T. et al., *J. Infec. Dis.* 161:982–987 (1990)).

Passive immunotherapy directed at neutralizing TNF may have a beneficial effect in Gram-negative sepsis and endotoxemia, based on the increased TNF production and elevated TNF levels in these pathology states, as discussed above.

Antibodies to a "modulator" material which was characterized as cachectin (later found to be identical to TNF) were disclosed by Cerami et al. (EPO Patent Publication 0,212, 489, Mar. 4, 1987). Such antibodies were said to be useful in diagnostic immunoassays and in therapy of shock in bacterial infections. Rubin et al. (EPO Patent Publication 0,218,868, Apr. 22, 1987) disclosed monoclonal antibodies to human TNF, the hybridomas secreting such antibodies, methods of producing such antibodies, and the use of such antibodies in immunoassay of TNF. Yone et al. (EPO Patent Publication 0,288,088, Oct. 26, 1988) disclosed anti-TNF antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, T., *Allergy* 16:178 (1967); Kawasaki, T., Shonica (*Pediatrics*) 26:935 (1985)) were said to contain elevated TNF levels which were related to progress of the pathology (Yone et al., supra).

Other investigators have described mAbs specific for recombinant human TNF which had neutralizing activity in vitro (Liang, C-M. et al. *Biochem. Biophys. Res. Comm.* 137:847–854 (1986); Meager, A. et al., *Hybridoma* 6:305–311 (1987); Fendly et al., *Hybridoma* 6:359–369 (1987); Bringman, T. S. et al., *Hybridoma* 6:489–507 (1987); Hirai, M. et al., *J. Immunol. Meth.* 96:57–62 (1987); Moller, A. et al. (*Cytokine* 2:162–169 (1990)). Some of these mAbs were used to map epitopes of human TNF and develop enzyme immunoassays (Fendly et al., supra; Hirai et al., supra; Moller et al., supra) and to assist in the purification of recombinant TNF (Bringman et al., supra). However, these studies do not provide a basis for producing TNF neutralizing antibodies that can be used for in vivo diagnostic or therapeutic uses in humans, due to immunogenicity, lack of specificity and/or pharmaceutical suitability.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems (Mathison, J. C. et al., *J. Clin. Invest.* 81:1925–1937 (1988); Beutler, B. et al., *Science* 229:869–871 (1985); Tracey, K. J. et al., *Nature* 330:662–664 (1987); Shimamoto, Y. et al., *Immunol. Lett.* 17:311–318 (1988); Silva, A. T. et al., *J. Infect. Dis.* 162:421–427 (1990); Opal, S. M. et al., *J. Infect. Dis.* 161:1148–1152 (1990); Hinshaw, L. B. et al., *Circ. Shock* 30:279–292 (1990)).

To date, experience with anti-TNF mAb therapy in humans has been limited but shows beneficial therapeutic results, e.g., in arthritis and sepsis. See, e.g., Elliott, M. J. et al., *Baillieres Clin. Rheumatol.* 9:633–52 (1995); Feldmann M, et al., *Ann. N.Y. Acad. Sci. USA* 766:272–8 (1995); van der Poll, T. et al., *Shock* 3:1–12 (1995); Wherry et al., *Crit. Care. Med.* 21:S436–40 (1993); Tracey K. J., et al., *Crit. Care Med.* 21:S415–22 (1993).

Sequence analysis of cytokine receptors has defined several subfamilies of membrane proteins (1) the Ig superfamily, (2) the hematopoietin (cytokine receptor superfamily and (3) the tumor necrosis factor (TNF)/nerve growth factor (NGF) receptor superfamily (for review of TNF superfamily see, Gruss and Dower, *Blood* 85(12):3378–3404 (1995) and Aggarwal and Natarajan, *Eur. Cytokine Netw.*, 7(2):93–124 (1996)). The TNF/NGF receptor superfamily contains at least 10 different proteins. Gruss and Dower, supra. Ligands for these receptors have been identified and belong to at least two cytokine superfamilies. Gruss and Dower, supra.

Accordingly, there is a need to provide cytokines similar to TNF that are involved in pathological conditions. Such novel cytokines could be used to make novel antibodies or other antagonists that bind these TNF-like cytokines for therapy of TNF-like disorders.

SUMMARY OF THE INVENTION

The present invention provides isolated nucleic acid molecules comprising a polynucleotide encoding a cytokine that is similar to TNF and is believed to have similar biological effects and activities. This cytokine is named endokine alpha, and includes endokine alpha polypeptides having at least a portion of the amino acid sequence in FIGS. 1A–1B (SEQ ID NO:2) or an amino acid sequence encoded by the cDNA clone deposited as ATCC Deposit Number 97640 on Jun. 27, 1996. The nucleotide sequence, which was determined by sequencing the deposited endokine alpha cDNA clone, contains an open reading frame encoding a polypeptide of about 169 amino acid residues including an N-terminal methionine, an intracellular domain of about 17 amino acid residues, a transmembrane domain of about 26 amino acids, an extracellular domain of about 126 amino acids, and a deduced molecular weight for the complete protein of about 19 kDa.

Thus, one aspect of the invention provides an isolated nucleic acid molecule comprising apolynucleotidehaving anucleotide sequence selected from the group consisting of: (a) a nucleotide sequence encoding the endokine alpha polypeptide having the complete amino acid sequence in SEQ ID NO:2; (b) a nucleotide sequence encoding the endokine alpha polypeptide having the complete amino acid sequence in SEQ ID NO:2 but minus the N-terminal methionine residue; (c) a nucleotide sequence encoding the endokine alpha polypeptide having the complete amino acid sequence encoded by the cDNA clone contained in ATCC Deposit No. 97640; and (d) a nucleotide sequence complementary to any of the nucleotide sequences in (a), (b) or (c) above.

Further embodiments of the invention include isolated nucleic acid molecules that comprise or, alternatively, consist of, a polynucleotide having a nucleotide sequence at least 80%, 85%, 90%, 92%, or 95% identical, and more preferably at least 96%, 97%, 98% or 99% identical, to any of the nucleotide sequences in (a), (b), (c), or (d), above, or a polynucleotide which hybridizes under stringent hybridization conditions to a polynucleotide in (a), (b), (c), or (d), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a endokine alpha polypeptide having an amino acid sequence in (a), (b), (c), or (d), above.

The invention is further directed to nucleic acid fragments of the nucleic acid molecules described herein. Preferred nucleic acid fragments include nucleic acid molecules which encode: a polypeptide comprising the endokine alpha intracellular domain (amino acid residues from about 1 to about 17 in FIGS. 1A–1B (SEQ ID NO:2)); a polypeptide comprising the endokine alpha transmembrane domain (amino acid residues from about 18 to about 43 in FIGS. 1A–1B (SEQ ID NO:2)); and a polypeptide comprising the endokine alpha extracellular domain (amino acid residues from about 44 to about 169 in FIGS. 1A–1B (SEQ ID NO:2)).

The present invention also relates to recombinant vectors, which include the isolated nucleic acid molecules of the present invention, and to host cells containing the recombinant vectors, as well as to methods of making such vectors and host cells and for using them for production of endokine alpha polypeptides or peptides by recombinant techniques.

The invention further provides an isolated endokine alpha polypeptide having an amino acid sequence selected from the group consisting of: (a) the complete 169 amino acid sequence in SEQ ID NO:2; (b) the complete 169 amino acid sequence in SEQ ID NO:2 but minus the N-terminal methionine residue; (c) the complete amino acid sequence encoded by the cDNA clone contained in ATCC Deposit No. 97640; and (d) the amino acid sequence of an epitope-bearing portion of any one of the polypeptides of (a), (b), or (c). The polypeptides of the present invention also include polypeptides having an amino acid sequence at least 80%, 85%, 90%, 92%, or 95% identical, more preferably at least 96%, 97%, 98% or 99% identical to those above.

Peptides or polypeptides having the amino acid sequence of an epitope-bearing portion of a endokine alpha polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to an endokine alpha polypeptide having an amino acid sequence described in (a), (b), (c), or (d) above.

Preferred polypeptide fragments according to the present invention include a polypeptide comprising: the endokine alpha intracellular domain, the endokine alpha transmembrane domain, and the endokine alpha extracellular domain.

The invention further provides methods for isolating antibodies that bind specifically to an endokine alpha polypeptide having an amino acid sequence as described above. Such antibodies may be useful diagnostically or therapeutically as antagonists in the treatment of endokine alpha- and/or TNF-related disorders. The invention also provides a diagnostic method for determining the presence of a TNF-related disorder.

BRIEF DESCRIPTION OF THE FIGURES

FIGS. 1A–1B shows the nucleotide (SEQ ID NO:1) and deduced amino acid (SEQ ID NO:2) sequences of the endokine alpha protein. Amino acids 1 to 17 represent the intracellular domain, amino acids 18 to 43 the transmembrane domain (the underlined sequence), and amino acids 44 to 169 the extracellular domain (the remaining sequence).

FIG. 2 shows the regions of similarity between the amino acid sequences of the endokine alpha protein (SEQ ID NO:2), tissue necrosis factor α (TNF-α) (SEQ ID NO:3), and TNF-β (SEQ ID NO:4). The *J. Hein method was used with PAM* 250 residue weight table. Shading with solid black indicates residues that match consensus exactly.

DETAILED DESCRIPTION OF THE INVENTION

Figure 3:
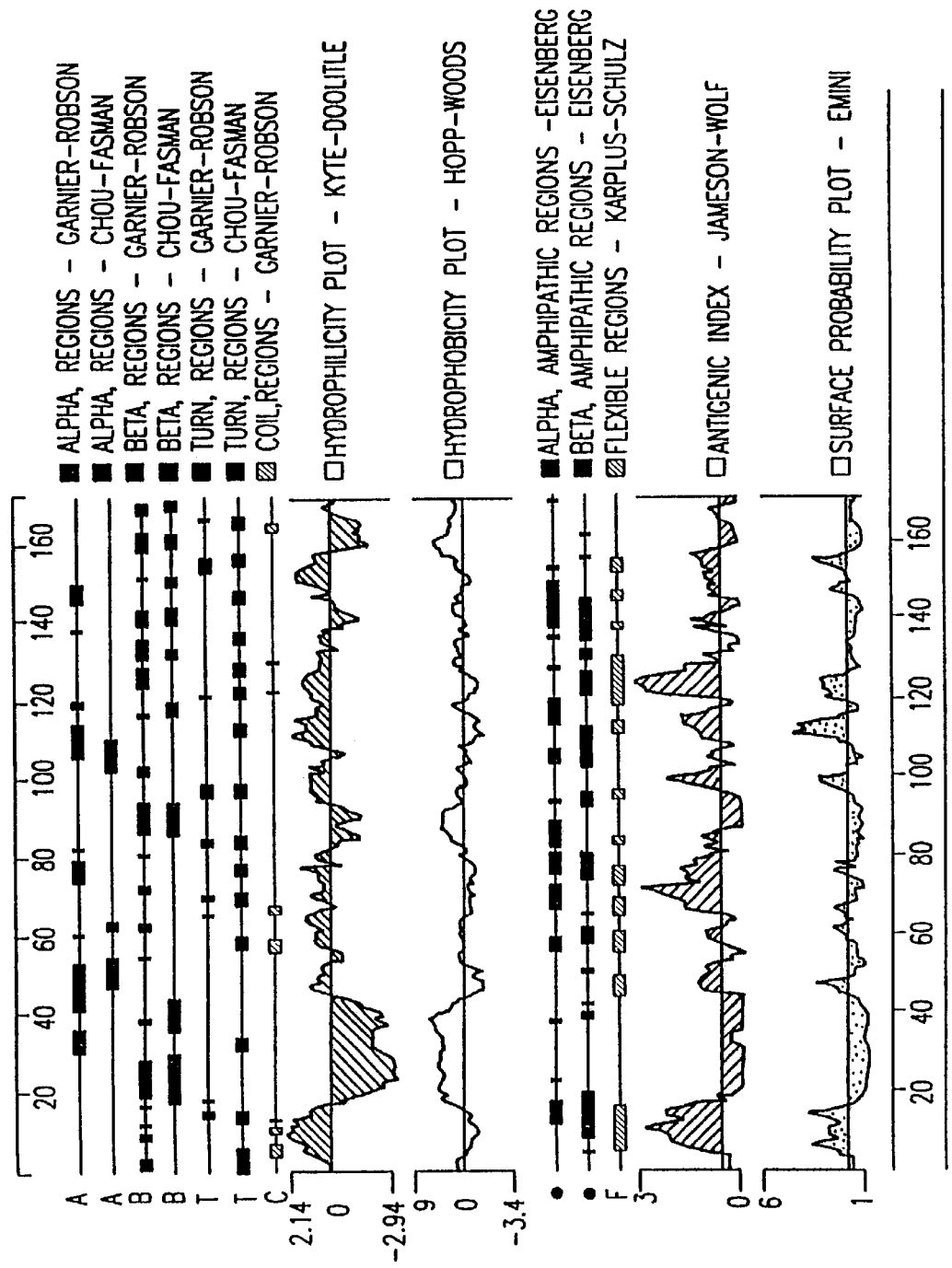
FIG. 3 provides an analysis of the endokine alpha amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 44–54, 57–68, 69–78, 94–105, 108–132 and 148–158 in FIGS. 1A–1B correspond to the shown highly antigenic regions of the endokine alpha protein.

The present invention provides isolated nucleic acid molecules comprising a polynucleotide encoding an endokine alpha protein having an amino acid sequence shown in FIGS. 1A–1B (SEQ ID NO:2), which was determined by sequencing a cloned cDNA. Endokine alpha is a novel member of the tumor necrosis factor (TNF) ligand family and shares sequence homology with human TNFα and related TNF family members (FIG. 2). The nucleotide sequence shown in FIGS. 1A–1B (SEQ ID NO:1) was obtained by sequencing a cDNA clone, which was deposited on Jun. 27, 1996, at the American Type Culture Collection, Patent Depository, 10801 University Boulevard, Manassas, Va. 20110-2209, and given accession number 97640. The deposited clone is contained in the pBluescript SK(-) plasmid (Stratagene, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.99% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the expected amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G , C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of FIGS. 1A–1B (SEQ ID NO:1) set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

Using the information provided herein, such as the nucleotide sequence in FIGS. 1A–1B, a nucleic acid molecule of the present invention encoding an endokine alpha polypeptide can be obtained using standard cloning and screening procedures, such as those for cloning cDNAs using mRNA as starting material. Illustrative of the invention, the nucleic acid molecule described in FIGS. 1A–1B (SEQ ID NO:1) was discovered in a cDNA library derived from human brain striatum. Expressed sequence tags corresponding to a portion of the endokine alpha cDNA were also found in several endothelial libraries and a fetal liver library.

The endokine alpha gene contains an open reading frame encoding a protein of about 169 amino acid residues, an intracellular domain of about 17 amino acids (amino acid residues from about 1 to about 17 in FIGS. 1A–1B (SEQ ID NO:2)), a transmembrane domain of about 26 amino acids (amino acid residues from about 18 to about 43 in FIGS. 1A–1B (SEQ ID NO:2)), an extracellular domain of about 126 amino acids (amino acid residues from about 44 to about 169 in FIGS. 1A–1B (SEQ ID NO:2)); and a deduced molecular weight of about 19 kDa. The endokine alpha protein shown in FIGS. 1A–1B (SEQ ID NO: 2) is about 30% similar and about 22% identical to human TNF-α, which can be accessed on GenBank as Accession No. U42764.

As one of ordinary skill would appreciate, due to the possibilities of sequencing errors discussed above the actual endokine alpha polypeptide encoded by the deposited cDNA comprises about 169 amino acids, but can be anywhere in the range of about 154–184 amino acids. It will also be appreciated by reasonable persons of skill in the art that, depending on the criteria used, the exact 'address' of the above-described endokine alpha protein domains may differ. Thus, for example, the exact location of the endokine alpha intracellular, transmembrane and extracellular domains shown in FIGS. 1A–1B (SEQ ID NO:2) may vary slightly (e.g., the exact address may differ by about 1 to about 5 residues compared to that shown in FIGS. 1A–1B) depending on the criteria used to define the domain.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA can be the coding strand, also known as the sense strand, or it can be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread," as in a karyotype), is not "isolated" for the purposes of the invention. As discussed further herein, isolated nucleic acid molecules according to the present invention may be produced naturally, recombinantly, or synthetically.

Isolated nucleic acid molecules of the present invention include DNA molecules comprising the open reading frame (ORF) shown in FIGS. 1A–1B (SEQ ID NO:1) and further include nucleic acid molecules substantially different than all or part of the ORF sequence shown in FIGS. 1A–1B (SEQ ID NO:1) but which, due to the degeneracy of the genetic code, still encode the endokine alpha protein or a fragment thereof. Of course, the genetic code is well known in the art. Thus, it would be routine for one skilled in the art to generate the degenerate variants described above.

In another aspect, the invention provides isolated nucleic acid molecules encoding the endokine alpha polypeptide having an amino acid sequence encoded by the cDNA of the clone deposited as ATCC Deposit No. 97640 on Jun. 27, 1996. The invention further provides an isolated nucleic acid molecule having the nucleotide sequence shown in FIGS. 1A–1B (SEQ ID NO:1) or the nucleotide sequence of the endokine alpha cDNA contained in the above-described deposited clone, or a nucleic acid molecule having a sequence complementary to one of the above sequences. Such isolated molecules, particularly DNA molecules, are useful as probes for gene mapping by in situ hybridization with chromosomes and for detecting expression of the endokine alpha gene in human tissue, for instance, by Northern blot analysis. As described in detail below, detecting altered endokine alpha gene expression in certain tissues or bodily fluids is indicative of certain disorders.

The present invention is further directed to fragments of the isolated nucleic acid molecules described herein. By a fragment of an isolated nucleic acid molecule having the nucleotide sequence of the deposited cDNA or the nucleotide sequence shown in FIGS. 1A–1B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, 250, 300, 350, 400, 450, and 500 nt in length are also useful according to the present invention as are fragments corresponding to most, if not all, of the nucleotide sequence of the deposited cDNA or as shown in FIGS. 1A–1B (SEQ ID NO:1). In this context, "about" includes the particularly recited value and values larger or smaller by several (5, 4, 3, 2 or 1) nucleotides. By a fragment at least 20 nt in length, for example, is intended fragments which include 20 or more contiguous bases from the nucleotide sequence of the deposited cDNA or the nucleotide sequence as shown in FIGS. 1A–1B (SEQ ID NO:1). Since the gene has been deposited and the nucleotide sequence shown in FIGS. 1A–1B (SEQ ID NO 1) is provided, generating such DNA fragments would be routine to the skilled artisan. For example, restriction endonuclease cleavage or shearing by sonication could easily be used to generate fragments of various sizes. Alternatively, such fragments could be generated synthetically.

In addition, the present inventors have also identified the following related cDNA clone: HEMCG04R (SEQ ID NO:11), which, by BLAST analysis has 94% identity to nucleotides 26 to 482 of SEQ ID NO:1.

Preferred nucleic acid fragments of the present invention include nucleic acid molecules encoding: a polypeptide comprising or, alternatively, consisting of, the endokine alpha intracellular domain (amino acid residues from about 1 to about 17 in FIGS. 1A–1B (SEQ ID NO 2), or as encoded by the cDNA clone contained in ATCC Deposit No. 97640); a polypeptide comprising or, alternatively, consisting of, the endokine alpha transmembrane domain (amino acid residues from about 18 to about 43 in FIGS. 1A–1B (SEQ ID NO 2), or as encoded by the cDNA clone contained in ATCC Deposit No. 97640); and a polypeptide comprising or, alternatively, consisting of, the endokine alpha extracellular domain (amino acid residues from about 44 to about 169 in FIGS. 1A–1B (SEQ ID NO:2), or as encoded by the cDNA clone contained in ATCC Deposit No. 97640).

Further preferred nucleic acid fragments of the present invention include nucleic acid molecules encoding epitope-bearing portions of the endokine alpha protein. In particular, such nucleic acid fragments of the present invention include nucleic acid molecules encoding a polypeptide comprising or, alternatively, consisting of one, two, three or more of any of the following amino acid sequences and polynucleotides encoding these polypeptides: amino acid residues from about 44 to about 158 in FIGS. 1A–1B (SEQ ID NO:2); amino acid residues from about 44 to about 54 in FIGS. 1A–1B (SEQ ID NO:2); amino acid residues from about 57 to about 68 in FIGS. 1A–1B (SEQ ID NO:2); amino acid residues from about 69 to about 78 in FIGS. 1A–1B (SEQ ID NO:2); amino acid residues from about 94 to about 105 in FIGS. 1A–1B (SEQ ID NO:2); amino acid residues from about 108 to about 132 in FIGS. 1A–1B (SEQ ID NO:2); and amino acid residues from about 148 to about 158 in FIGS. 1A–1B (SEQ ID NO:2). The inventors have determined that the above polypeptide fragments are antigenic regions of the endokine alpha protein. Methods for determining other such epitope-bearing portions of the endokine alpha protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the complement of an endokine alpha polynucleotide fragment described herein, or the cDNA clone contained in ATCC Deposit 97640 made on Jun. 27, 1996. By "stringent hybridization conditions" is intended overnight incubation at 42° C. in a solution comprising: 50% formamide, 5×SSC (750 mM NaCl, 75 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–500 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIGS. 1A–1B (SEQ ID NO:1). By a portion of a polynucleotide of "at least 20 nt in length," for example, is intended 20 or more contiguous nucleotides from the nucleotide sequence of the reference polynucleotide, (e.g., the deposited cDNA or the nucleotide sequence as shown in FIGS. 1A–1B (SEQ ID NO:1)). As indicated, such portions are useful diagnostically either as a probe according to conventional DNA hybridization techniques or as primers for amplification of a target sequence by the polymerase chain reaction (PCR), as described, for instance, in Sambrook, J. et al., eds., *Molecular Cloning, A Laboratory Manual*, 2nd. edition, Cold Spring Harbor Laboratory Press, Cold Spring Harbor, N.Y. (1989), the entire disclosure of which is hereby incorporated herein by reference.

Since an endokine alpha cDNA clone has been deposited and its nucleotide sequence is provided in FIGS. 1A–1B (SEQ ID NO:1), generating polynucleotides which hybridize to a portion of the endokine alpha cDNA molecule would be routine to the skilled artisan. For example, restriction endonuclease cleavage or shearing by sonication of the endokine alpha cDNA clone could easily be used to generate DNA portions of various sizes which are polynucleotides that hybridize to a portion of the endokine alpha cDNA molecule. Alternatively, the hybridizing polynucleotides of the present invention could be generated synthetically according to known techniques.

Of course, a polynucleotide which hybridizes only to a poly A sequence (such as the 3' terminal poly(A) tract of the endokine alpha cDNA shown in FIGS. 1A–1B (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention that encode an endokine alpha protein may include, but are not limited to, those encoding the amino acid sequence of the polypeptide, by itself; the coding sequence for the polypeptide and additional sequences, such as a pre-, or pro- or prepro-protein sequence; the coding sequence of the polypeptide, with or without the aforementioned additional coding sequences, together with additional, non-coding sequences, including for example, but not limited to, introns and non-coding 5' and 3' sequences, such as the transcribed, non-translated sequences that play a role in transcription, mRNA processing—including splicing and polyadenylation signals, e.g., ribosome binding and stability of mRNA; an additional coding sequence which codes for additional amino acids, such as those which provide additional functionalities. Thus, for instance, the sequence encoding the polypeptide can be fused to a marker sequence, such as a sequence encoding a peptide which facilitates purification of the fused polypeptide. In certain preferred embodiments ofthis aspect of the invention, the marker amino acid sequence is a hexa-histidine peptide, such as the tag provided in a pQE vector (Qiagen, Inc.), among others, many of which are publicly and/or commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin (HA) protein, which has been described by Wilson et al., *Cell* 37:767 (1984). Other such fusion proteins include the endokine alpha protein fused to Fc at the N- or C-terminus.

The present invention further relates to variants of the nucleic acid molecules of the present invention, which encode portions, analogs or derivatives of the endokine alpha protein. Variants can occur naturally, such as a natural allelic variant. By an "allelic variant" is intended one of several alternate forms of a gene occupying a given locus on a chromosome of an organism. Non-naturally occurring variants can be produced, e.g. using art-known mutagenesis techniques.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Such variants include those produced by nucleotide substitutions, deletions or additions. The substitutions, deletions or additions may involve one or more nucleotides. The variants can be altered in coding or non-coding regions or both. Alterations in the coding regions can produce conservative or non-conservative amino acid substitutions, deletions or additions. Especially preferred among these are silent substitutions, additions and deletions, which do not alter the properties and activities of the endokine alpha protein or portions thereof. Also especially preferred in this regard are conservative substitutions. Most highly preferred are nucleic acid molecules encoding the endokine alpha protein having the amino acid sequence shown in FIGS. 1A–1B (SEQ ID NO:2) or the endokine alpha amino acid sequence encoded by the deposited cDNA clone.

Further embodiments of the invention include isolated nucleic acid molecules comprising or, alternatively, consisting of, a polynucleotide having a nucleotide sequence at least 80%, 85%, 90%, 92% or 95% identical, and more preferably at least 96%, 97%, 98%, or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence encoded by the cDNA clone contained in ATCC Deposit No. 97640; or (d) a nucleotide sequence complementary to any of the nucleotide sequences in (a), (b), or (c).

By a polynucleotide having a nucleotide sequence at least, for example, 95% "identical" to a reference nucleotide sequence encoding an endokine alpha polypeptide is intended that the nucleotide sequence of the polynucleotide is identical to the reference sequence except that the polynucleotide sequence may include up to five point mutations per each 100 nucleotides of the reference nucleotide sequence encoding the endokine alpha polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

The reference (query) sequence may be the entire endokine alpha encoding nucleotide sequence shown in FIGS. 1A–1B (SEQ ID NO:1) or any endokine alpha polynucleotide fragment as described herein.

As a practical matter, whether any particular nucleic acid molecule is at least 80%, 85%, 90%, 92%, 95%, 96%, 97%, 98%, or 99% identical to, for instance, the nucleotide sequence shown in FIGS. 1A–1B or to the nucleotide sequence of the deposited cDNA clone can be determined conventionally using known computer programs such as the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, *Adv. Appl. Math.* 2:482–489 (1981), to find the best segment of homology between two sequences. When using BESTFIT or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, CutoffScore=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a match/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to such nucleic acid molecules which are at least 80%, 85%, 90%, 92%, 95%, 96%, 97%, 98%, or 99% identical to a nucleic acid sequence described above irrespective of whether they encode a polypeptide having endokine alpha protein activity. This is because, even where a particular nucleic acid molecule does not encode a polypeptide having endokine alpha activity, one of skill in the art would still know how to use the nucleic acid molecule, for instance, as a hybridization probe or a polymerase chain reaction (PCR) primer. Uses of the nucleic acid molecules of the present invention that do not encode a polypeptide having endokine alpha activity include, inter alia, (1) isolating the endokine alpha gene or allelic variants thereof from a cDNA library; (2) in situ hybridization (FISH) to metaphase chromosomal spreads to provide precise chromosomal location of the endokine alpha gene as described in Verma et al., *Human Chromosomes: a Manual of Basic Techniques*, Pergamon Press, New York (1988); and (3) Northern Blot analysis for detecting endokine alpha mRNA expression in specific tissues.

Preferred, however, are such nucleic acid molecules having sequences at least 80%, 85%, 90%, 92%, 95%, 96%, 97%, 98%, or 99% identical to a nucleic acid sequence described above which do, in fact, encode a polypeptide having endokine alpha protein activity. By "a polypeptide having endokine alpha activity" is intended polypeptides exhibiting similar, but not necessarily identical, activity as compared to the endokine alpha protein as measured in a particular biological assay. Endokine alpha activity can be assayed according to known methods. For example, a cytotoxicity assay or cell proliferation assay can be used where endokine alpha polypeptides are added to cells in culture and the effect of the endokine on the cells is determined by measuring the decrease or increase in cell numbers.

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98%, or 99% identical to a nucleic acid sequence described above will encode a polypeptide "having endokine alpha protein activity." In fact, since degenerate variants all encode the same polypeptide, this will be clear to the skilled artisan even without performing the above described comparison assay. It will be further recognized in the art that, for such nucleic acid molecules that are not degenerate variants, a reasonable number will also encode a polypeptide having endokine alpha protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., supra, and the references cited therein.

By "a polypeptide having endokine alpha functional activity" is intended polypeptides exhibiting activity similar, but not necessarily identical, to an activity of the endokine alpha receptors of the present invention (either the full-length polypeptide, or the splice variants), as measured, for example, in a particular immunoassay or biological assay. For example, endokine alpha activity can be measured by determining the ability of an endokine alpha polypeptide to bind an endokine alpha ligand (e.g., TR11 (GITR, AITR)). Endokine alpha activity may also be measured by determining the ability of a polypeptide, such as cognate ligand which is free or expressed on a cell surface, to stimulate proliferation, differentiation or activation, or to stimulate TNF-α production, and/or to inhibit IL-12 production in cells expressing the polypeptide, for example, B cells, T cells and monocytes.

The present invention is further directed to fragments of the isolated nucleic acid molecules (i.e. polynucleotides) described herein. By a fragment of an isolated nucleic acid molecule having, for example, the nucleotide sequence of the deposited cDNA (clone 97640), a nucleotide sequence encoding the polypeptide sequence encoded by the deposited cDNA, a nucleotide sequence encoding the polypeptide sequence depicted in FIGS. 1A–1B (SEQ ID NO:2), the nucleotide sequence shown in FIGS. 1A–1B (SEQ ID NO:1), or the complementary strand thereto, is intended fragments at least 15 nucleotides, and more preferably at least about20 nucleotides, still more preferably at least 30 nucleotides, and even more preferably, at least about 40, 50, 100, 150, 200, 250, 300, 325, 350, 375, 400, 450, 500, 550, or 600 nucleotides in length. In this context, "about" includes the particularly recited value and values larger or smaller by several (5, 4, 3, 2 or 1) nucleotides. These fragments have numerous uses which include, but are not limited to, diagnostic probes and primers as discussed herein. Of course, larger fragments, such as those of 501–1500 nucleotides in length are also useful according to the present invention as are fragments corresponding to most, if not all, of the nucleotide sequences of the deposited cDNA (clone 97640) or as shown in FIGS. 1A–1B (SEQ ID NO:1). By a fragment at least 20 nucleotides in length, for example, is intended fragments which include 20 or more contiguous bases from, for example, the nucleotide sequence of the deposited cDNA, or the nucleotide sequence as shown in FIGS. 1A–1B (SEQ ID NO:1).

Representative examples of endokine alpha polynucleotide fragments of the invention include, for example, fragments. that comprise, or alternatively, consist of, a sequence from about nucleotide 1 to 50, 51 to 100, 101 to 150, 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 801 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, and/or 1801 to 1840 of SEQ ID NO:1, or the complementary strand thereto, or the cDNA contained in the deposited clone. In this context "about" includes the particularly recited ranges, larger or smaller by several (5, 4, 3, 2, or 1) nucleotides, at either terminus or at both termini.

In specific embodiments, the polynucleotide fragments of the invention comprise, or alternatively, consist of, a sequence from nucleotide 961 to 1000, 1730 to 1770, 1770 to 1800, and/or 1800 to 1840, of SEQ ID NO:1, or the complementary strand thereto. Polynucleotides that hybridize to these polynucleotide fragments are also encompassed by the invention.

Preferably, the polynucleotide fragments of the invention encode a polypeptide which demonstrates an endokine alpha functional activity. By a polypeptide demonstrating "functional activity" is meant, a polypeptide capable of displaying one or more known fimctional activities associated with a full-length endokine alpha polypeptide. Such functional activities include, but are not limited to, biological activity (e.g., stimulation of B cell proliferation, differentiation or activation; stimulation of T cell proliferation, differentiation or activation; stimulation of TNF-α production in monocytes; and/or inhibition of IL-12 production in monocytes), antigenicity (ability to bind (or compete with an endokine alpha polypeptide for binding) to an anti-endokine alpha antibody), immunogenicity (ability to generate antibody which binds to a endokine alpha polypeptide), ability to multimerize with native endokine alpha and ability to bind to a receptor or ligand for a endokine alpha polypeptide (e.g., TR11; see U.S. patent application Ser. No. 09/176, 200).

The functional activity of endokine alpha polypeptides, and fragments, variants, derivatives, and analogs thereof, can be assayed by various methods. For example, in one embodiment where one is assaying for the ability to bind or compete with full-length endokine alpha polypeptide for binding to anti-endokine alpha antibody, various immunoassays known in the art can be used, including, but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where an endokine alpha ligand is identified (e.g., TR11), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94–123 (1995). In another embodiment, physiological correlates (signal transduction) of endokine alpha binding to its substrates can be assayed.

In addition, assays described herein (see Examples 5–8) and methods otherwise known in the art may routinely be applied to measure the ability of endokine alpha polypeptides and fragments, variants, derivatives and analogs thereof to elicit endokine alpha related biological activity (e.g., stimulation of B cell proliferation, differentiation or activation; stimulation of T cell proliferation, differentiation or activation; stimulation of TNF-α production in monocytes; and/or inhibition of IL-12 production in monocytes in vitro or in vivo). Other methods will be known to the skilled artisan and are within the scope of the invention.

Vectors and Host Cells

The present invention also relates to vectors which include the isolated DNA molecules of the present invention, host cells which are genetically engineered with the recombinant vectors, and the production of endokine alpha polypeptides or portions thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate transacting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids. See, e.g., Ausubel, infra; Sambrook, infra.

The DNA insert should be operatively linked to an appropriate promoter, such as the phage lambda PL promoter, the *E. coli*: lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture media and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. In a further example, a region of additional amino acids, particularly charged amino acids, may be added to the N-terminus of the polypeptide to improve stability and persistence in the host cell, during purification or during subsequent handling and storage. Also, as indicated, a region (s) also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize receptors. For example, EP A 0,464,533 (also, Canadian counterpart 2,045,869) discloses fusion proteins comprising various portions of constant region of immunoglobin molecules together with another human protein or part thereof. In many cases, the Fc part in the fusion protein is thoroughly advantageous for use in therapy and diagnosis and thus results, for example, in improved pharmacokinetic properties (EP A 0,232,262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists (for example, hIL-5). See, D. Bennett et al., *Journal of Molecular Recognition* 8:52–58 (1995) and K. Johanson et al., *The Journal of Biological Chemistry* 270(16):9459–9471 (1995).

The endokine alpha protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., endokine alpha coding sequence), and/or to include genetic material (e.g., heterologous polynucleotide sequences) that is operably associated with endokine alpha polynucleotides of the invention, and which activates, alters, and/or amplifies endogenous endokine alpha polynucleotides. For example, techniques known in the art may be used to operably associate heterologous control regions (e.g., promoter and/or enhancer) and endogenous endokine alpha polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

Endokine Alpha Polypeptides and Peptides

The invention further provides an isolated endokine alpha polypeptide having the amino acid sequence encoded by the deposited cDNA, or the amino acid sequence in FIGS. 1A–1B (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

By "isolated" polypeptide or protein is intended a polypeptide or protein removed from its native environment.

For example, recombinantly produced polypeptides and proteins expressed in recombinant host cells are considered isolated for purposes of the invention as are native or recombinant polypeptides and proteins which have been substantially purified by any suitable technique such as, for example, the one-step method described in Smith and Johnson, *Gene* 67:31–40 (1988).

It will be recognized in the art that some amino acid sequence of the endokine alpha polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the endokine alpha polypeptide which show substantial endokine alpha polypeptide activity or which include regions of endokine alpha protein such as the protein fragments discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the endokine alpha protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the endokine alpha of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given endokine alpha polypeptide will not be more than 50, 40, 30, 20, 10, 5, or 3, depending on the objective.

Amino acids in the endokine alpha protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the endokine alpha polypeptide can be substantially purified by the one-step method described in Smith and Johnson, *Gene* 67:31–40 (1988).

The polypeptides of the present invention include the polypeptides comprising or, alternatively, consisting of: (a) the complete amino acid sequence as shown in FIGS. 1A–1B (SEQ ID NO:2); (b) the complete amino acid sequence as shown in FIGS. 1A–1B (SEQ ID NO:2), but minus the N-terminal methionine residue; (c) the amino acid sequence of the endokine alpha polypeptide having the amino acid sequence encoded by the cDNA clone contained in ATCC Deposit No. 97640; and (d) the amino acid sequence of an epitope-bearing portion of any one of the polypeptides of (a), (b), or (c), as well as polypeptides which are at least 80%, 85%, 90%, 92% or 95% identical, more preferably at least 96%, 97%, 98% or 99% identical to a polypeptide described herein, and also include portions of such polypeptides with at least 30 amino acids and more preferably at least 50 amino acids.

By a polypeptide having an amino acid sequence at least, for example, 95% "identical" to a reference amino acid sequence of an endokine alpha polypeptide is intended that the amino acid sequence of the polypeptide is identical to the reference sequence except that the polypeptide sequence may include up to five amino acid alterations per each 100 amino acids of the reference amino acid sequence of the endokine alpha polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide comprises or, alternatively, consists of, a sequence at least 80%, 85%, 90%, 92%, 95%, 96%, 97%, 98% or 99% identical to, for instance, the amino acid sequence shown in FIGS. 1A–1B (SEQ ID NO:2) or to the amino acid sequence encoded by deposited cDNA clone can be determined conventionally using known computer programs such the BESTFIT program (Wisconsin Sequence Analysis Package, Version 8 for Unix, Genetics Computer Group, University Research Park, 575 Science Drive, Madison, Wis. 53711. When using BESTFIT or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present inventors have discovered that the endokine alpha protein is a 169 residue protein exhibiting three main structural domains. The intracellular domain was identified within residues from about 1 to about 17 in FIGS. 1A–1B (SEQ ID NO:2). The transmembrane domain was identified within residues from about 18 to about 43 in FIGS. 1A–1B (SEQ ID NO:2). The extracellular domain was identified within residues from about 44 to about 169 in FIGS. 1A–1B (SEQ ID NO:2). Thus, the invention further provides preferred endokine alpha protein fragments comprising a polypeptide selected from: the endokine alpha intracellular domain, the transmembrane domain and the endokine alpha extracellular domain.

The extracellular domain of the endokine alpha protein can be combined with parts of the constant domain of immunoglobulins (IgG), resulting in chimeric polypeptides. These fusion proteins show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing the ligands than the monomeric extracellular domains alone (Fountoulakis et al., J. Biochem. 270:3958–3964 (1995)).

Polypeptide fragments of the present invention include polypeptides comprising or alternatively, consisting of, an amino acid sequence contained in SEQ ID NO:2, encoded by the cDNA contained in the deposited clone, or encoded by nucleic acids which hybridize (e.g., under stringent hybridization conditions) to the nucleotide sequence contained in the deposited clone, or shown in FIGS. 1A–1B (SEQ ID NO:1) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues: 1 to 50, 51 to 100, 101 to 150 and/or 151 to 169 of SEQ ID NO:2. In this context, "about" includes the particularly recited ranges and ranges larger or smaller by several (5, 4, 3, 2, or 1) amino acids, at either terminus or both termini. Moreover, polypeptide fragments can be at least 10, 20, 30, 40, 50, 60, 70, 80, 90, 100, 110, 120, 130, 140, 150 or 168 amino acids in length. Polynucleotides encoding these polypeptides are also encompassed by the invention. Polynucleotides that hybridize to the complement of these encoding polynucleotides are also encompassed by the invention, as are the polypeptides encoded by these hybridizing polynucleotides.

Among the especially preferred fragments of the invention are fragments characterized by structural or functional attributes of endokine alpha. Such fragments include amino acid residues that comprise alpha-helix and alpha-helix-forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of full-length endokine alpha (SEQ ID NO:2). Certain preferred regions are those set out in FIG. 3 and include, but are not limited to, regions of the aforementioned types identified by analysis of the amino acid sequence depicted in FIGS. 1A–1B (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

The data representing the structural or functional attributes of endokine alpha set forth in FIG. 3 and/or Table 2, as described above, was generated using the various modules and algorithms of the DNA*STAR set on default parameters. In a preferred embodiment, the data presented in columns VIII, IX, XIII, and XIV of Table 2 can be used to determine regions of endokine alpha which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table 2, be represented or identified by using tabular representations of the data presented in FIG. 3. The DNA*STAR computer algorithm used to generate FIG. 3 (set on the original default parameters) was used to present the data in FIG. 3 in a tabular format (See Table 2). The tabular format of the data in FIG. 3 may be used to easily determine specific boundaries of a preferred region.

The above-mentioned preferred regions set out in FIG. 3 and in Table 2 include, but are not limited to, regions of the aforementioned types identified by analysis of the amino acid sequence set out in FIG. 3. As set out in FIG. 3 and in Table 2, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE 2

| Res | Position | I | II | III | IV | V | VI | VII | VIII | IX | X | XI | XII | XIII | XIV |
|-----|----------|---|----|----|----|---|----|----|------|-----|---|----|-----|------|-----|
| Met | 1 | — | — | B | — | — | T | — | −0.01 | 0.40 | — | — | — | −0.20 | 0.63 |
| Pro | 2 | — | — | B | — | — | T | — | 0.08 | 0.47 | — | — | — | −0.20 | 0.67 |
| Leu | 3 | — | — | B | — | — | T | — | 0.58 | 0.43 | — | — | — | −0.20 | 0.71 |
| Ser | 4 | — | — | — | — | — | T | C | 0.66 | 0.00 | — | — | — | 0.45 | 1.40 |
| His | 5 | — | — | — | — | — | T | C | 1.04 | −0.13 | — | * | — | 1.05 | 1.31 |
| Ser | 6 | — | — | — | — | — | T | C | 1.30 | −0.16 | — | — | F | 1.46 | 2.74 |
| Arg | 7 | — | — | — | — | — | T | C | 0.92 | −0.41 | — | — | F | 1.72 | 2.03 |
| Thr | 8 | — | — | B | — | — | T | — | 1.73 | −0.30 | — | * | F | 1.78 | 1.50 |
| Gln | 9 | — | — | B | — | — | — | — | 2.14 | −0.40 | — | * | F | 1.84 | 1.94 |
| Gly | 10 | — | — | — | — | — | — | C | 1.88 | −0.79 | — | * | F | 2.60 | 1.94 |
| Ala | 11 | — | — | — | — | — | — | C | 1.88 | −0.40 | — | * | F | 2.04 | 1.80 |
| Gln | 12 | — | — | B | — | — | — | — | 1.48 | −0.50 | * | * | F | 1.71 | 1.40 |
| Arg | 13 | — | — | — | — | — | T | C | 1.83 | 0.01 | * | * | F | 1.38 | 1.48 |
| Ser | 14 | — | — | — | — | T | T | — | 1.02 | −0.41 | * | * | F | 2.05 | 2.94 |
| Ser | 15 | — | — | — | — | T | T | — | 1.08 | −0.23 | * | * | F | 1.92 | 1.40 |
| Trp | 16 | — | — | — | — | T | T | — | 0.86 | 0.29 | * | * | F | 1.30 | 0.75 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 17 | — | — | B | B | — | — | — | 0.16 | 0.97 | * | * | — | -0.08 | 0.46 |
| Leu | 18 | — | — | — | B | T | — | — | -0.62 | 1.37 | * | * | — | 0.19 | 0.30 |
| Trp | 19 | — | — | B | B | — | — | — | -0.62 | 1.56 | — | * | — | -0.34 | 0.15 |
| Leu | 20 | — | — | B | B | — | — | — | -1.21 | 1.03 | — | * | — | -0.47 | 0.10 |
| Phe | 21 | — | — | B | B | — | — | — | -1.78 | 1.71 | — | * | — | -0.60 | 0.09 |
| Cys | 22 | — | — | B | B | — | — | — | -2.42 | 1.67 | — | — | — | -0.60 | 0.06 |
| Ser | 23 | — | — | B | B | — | — | — | -2.42 | 1.37 | * | — | — | -0.60 | 0.07 |
| Ile | 24 | — | — | B | B | — | — | — | -2.94 | 1.37 | — | — | — | -0.60 | 0.07 |
| Val | 25 | — | — | B | B | — | — | — | -2.83 | 1.27 | — | — | — | -0.60 | 0.11 |
| Met | 26 | — | — | B | B | — | — | — | -2.94 | 1.49 | — | — | — | -0.60 | 0.07 |
| Leu | 27 | — | — | B | B | — | — | — | -2.94 | 1.79 | — | — | — | -0.60 | 0.08 |
| Leu | 28 | — | — | B | B | — | — | — | -2.94 | 1.67 | — | — | — | -0.60 | 0.06 |
| Phe | 29 | — | — | B | B | — | — | — | -2.76 | 1.41 | — | — | — | -0.60 | 0.08 |
| Leu | 30 | A | — | — | B | — | — | — | -2.20 | 1.59 | — | — | — | -0.60 | 0.08 |
| Cys | 31 | A | — | — | — | — | T | — | -1.89 | 1.29 | — | — | — | -0.20 | 0.14 |
| Ser | 32 | A | — | — | — | — | T | — | -1.89 | 1.51 | — | — | — | -0.20 | 0.17 |
| Phe | 33 | A | — | — | — | — | T | — | -1.97 | 1.41 | — | — | — | -0.20 | 0.17 |
| Ser | 34 | A | — | — | — | — | T | — | -1.97 | 1.41 | — | — | — | -0.20 | 0.22 |
| Trp | 35 | A | — | — | B | — | — | — | -2.04 | 1.63 | — | — | — | -0.60 | 0.14 |
| Leu | 36 | A | — | — | B | — | — | — | -2.08 | 1.93 | — | — | — | -0.60 | 0.11 |
| Ile | 37 | — | — | B | B | — | — | — | -2.59 | 1.93 | * | — | — | -0.60 | 0.07 |
| Phe | 38 | — | — | B | B | — | — | — | -1.89 | 2.23 | * | * | — | -0.60 | 0.06 |
| Ile | 39 | — | — | B | B | — | — | — | -2.40 | 1.71 | — | * | — | -0.60 | 0.12 |
| Phe | 40 | A | — | — | B | — | — | — | -2.11 | 1.71 | — | * | — | -0.60 | 0.14 |
| Leu | 41 | A | — | — | B | — | — | — | -1.61 | 1.03 | — | — | — | -0.60 | 0.28 |
| Gln | 42 | A | — | — | B | — | — | — | -1.31 | 0.73 | — | * | — | -0.60 | 0.58 |
| Leu | 43 | A | — | — | B | — | — | — | -0.57 | 0.54 | — | — | — | -0.60 | 0.68 |
| Glu | 44 | A | — | — | B | — | — | — | 0.32 | -0.24 | — | — | F | 0.60 | 1.65 |
| Thr | 45 | A | A | — | — | — | — | — | 0.81 | -0.93 | — | — | F | 0.90 | 1.65 |
| Ala | 46 | A | A | — | — | — | — | — | 0.96 | -0.90 | — | — | F | 0.90 | 3.10 |
| Lys | 47 | A | A | — | — | — | — | — | 0.36 | -1.01 | — | — | F | 0.75 | 0.96 |
| Glu | 48 | A | A | — | — | — | — | — | 0.58 | -0.40 | — | — | F | 0.45 | 0.66 |
| Pro | 49 | A | A | — | — | — | — | — | 0.62 | -0.39 | — | * | F | 0.45 | 0.66 |
| Cys | 50 | A | A | — | — | — | — | — | 0.23 | -0.89 | — | * | — | 0.60 | 0.66 |
| Met | 51 | A | A | — | — | — | — | — | 0.48 | -0.10 | — | * | — | 0.30 | 0.33 |
| Ala | 52 | A | A | — | — | — | — | — | 0.22 | 0.33 | — | — | — | -0.30 | 0.21 |
| Lys | 53 | A | A | — | — | — | — | — | -0.59 | 0.33 | — | — | — | -0.30 | 0.61 |
| Phe | 54 | — | A | B | — | — | — | — | -0.59 | 0.44 | — | — | — | -0.60 | 0.51 |
| Gly | 55 | — | A | — | — | — | — | C | -0.22 | 0.26 | * | — | F | 0.05 | 0.77 |
| Pro | 56 | — | — | — | — | — | — | C | 0.42 | 0.14 | * | — | F | 0.25 | 0.52 |
| Leu | 57 | — | — | — | — | — | T | C | 0.72 | 0.14 | * | * | F | 0.60 | 1.20 |
| Pro | 58 | — | — | — | — | — | T | C | 0.68 | 0.27 | * | * | F | 0.60 | 1.27 |
| Ser | 59 | — | — | — | — | — | T | C | 0.78 | 0.24 | * | * | F | 0.60 | 1.43 |
| Lys | 60 | A | — | — | — | — | T | — | 0.53 | 0.43 | — | * | F | 0.10 | 1.71 |
| Trp | 61 | — | A | B | — | — | — | — | 0.44 | 0.24 | — | * | — | -0.15 | 1.12 |
| Gln | 62 | — | A | B | — | — | — | — | 0.96 | 0.20 | — | * | — | -0.15 | 1.12 |
| Met | 63 | — | A | B | — | — | — | — | 1.17 | 0.20 | — | — | — | -0.30 | 0.75 |
| Ala | 64 | — | A | B | — | — | — | — | 1.26 | 0.20 | — | — | — | -0.15 | 1.23 |
| Ser | 65 | — | — | — | — | T | — | — | 1.00 | -0.29 | — | * | F | 1.20 | 1.10 |
| Ser | 66 | — | — | — | — | — | — | C | 0.62 | -0.26 | * | — | F | 1.28 | 1.72 |
| Glu | 67 | — | — | — | — | — | — | C | -0.23 | -0.30 | * | — | F | 1.41 | 0.91 |
| Pro | 68 | — | — | — | — | — | T | C | 0.37 | -0.16 | * | — | F | 1.89 | 0.51 |
| Pro | 69 | — | — | — | — | T | T | — | 1.00 | -0.14 | * | — | F | 2.37 | 0.61 |
| Cys | 70 | — | — | — | — | T | T | — | 0.44 | -0.53 | * | — | — | 2.80 | 0.70 |
| Val | 71 | — | — | B | — | — | T | — | 0.44 | 0.11 | * | — | — | 1.22 | 0.34 |
| Asn | 72 | — | — | B | — | — | — | — | 0.44 | 0.07 | * | — | — | 0.74 | 0.29 |
| Lys | 73 | — | — | B | — | — | — | — | 0.37 | -0.36 | * | — | F | 1.21 | 0.91 |
| Val | 74 | A | — | — | — | — | — | — | 0.62 | -0.01 | — | * | F | 1.08 | 1.29 |
| Ser | 75 | A | — | — | — | — | T | — | 0.48 | -0.66 | * | * | F | 1.30 | 1.60 |
| Asp | 76 | A | — | — | — | — | T | — | 1.33 | -0.37 | * | * | F | 0.85 | 0.66 |
| Trp | 77 | A | — | — | — | — | T | — | 0.44 | -0.37 | * | * | F | 1.00 | 1.54 |
| Lys | 78 | A | — | — | — | — | T | — | -0.41 | -0.33 | * | * | — | 0.70 | 0.81 |
| Leu | 79 | A | — | — | — | — | — | — | 0.44 | -0.03 | * | * | — | 0.50 | 0.40 |
| Glu | 80 | A | — | — | — | — | — | — | 0.74 | 0.37 | * | * | — | -0.10 | 0.66 |
| Ile | 81 | — | — | B | — | — | — | — | 0.40 | -0.14 | * | * | — | 0.50 | 0.53 |
| Leu | 82 | A | — | — | — | — | T | — | -0.12 | 0.29 | — | * | — | 0.10 | 0.63 |
| Gln | 83 | — | — | — | — | T | T | — | -0.41 | 0.29 | — | * | F | 0.65 | 0.30 |
| Asn | 84 | — | — | — | — | T | T | — | -0.41 | 1.04 | * | — | F | 0.35 | 0.67 |
| Gly | 85 | — | — | — | — | T | T | — | -1.30 | 1.04 | * | — | F | 0.35 | 0.67 |
| Leu | 86 | — | — | B | B | — | — | — | -0.66 | 1.04 | * | — | — | -0.60 | 0.27 |
| Tyr | 87 | — | — | B | B | — | — | — | -0.19 | 1.40 | * | — | — | -0.60 | 0.27 |
| Leu | 88 | — | — | B | B | — | — | — | -0.19 | 1.43 | * | — | — | -0.60 | 0.27 |
| Ile | 89 | — | — | B | B | — | — | — | -1.04 | 1.40 | * | — | — | -0.60 | 0.56 |
| Tyr | 90 | — | — | B | B | — | — | — | -1.29 | 1.36 | — | — | — | -0.60 | 0.26 |
| Gly | 91 | — | — | B | B | — | — | — | -0.69 | 1.10 | — | — | — | -0.60 | 0.32 |
| Gln | 92 | — | — | B | B | — | — | — | -0.44 | 0.84 | — | * | — | 0.60 | 0.71 |
| Val | 93 | — | — | B | B | — | — | — | -0.22 | 0.56 | — | * | — | -0.60 | 0.73 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 94 | — | — | B | B | — | — | — | 0.67 | 0.30 | * | * | — | -0.30 | 0.75 |
| Pro | 95 | — | — | B | B | — | — | — | 0.67 | 0.27 | * | * | F | -0.20 | 0.69 |
| Asn | 96 | — | — | — | — | T | T | — | 1.01 | 0.63 | — | * | F | 0.76 | 1.47 |
| Ala | 97 | — | — | — | — | T | T | — | 1.01 | 0.39 | — | * | F | 1.19 | 2.33 |
| Asn | 98 | — | — | — | — | T | T | — | 1.01 | -0.11 | — | — | — | 1.77 | 2.52 |
| Tyr | 99 | — | — | — | — | T | T | — | 1.01 | 0.10 | — | — | — | 1.30 | 1.16 |
| Asn | 100 | — | — | B | — | — | — | — | 1.01 | 0.20 | — | — | — | 0.57 | 1.16 |
| Asp | 101 | — | — | B | — | — | — | — | 0.31 | 0.13 | — | — | — | 0.44 | 1.12 |
| Val | 102 | — | A | B | — | — | — | — | 0.90 | 0.51 | — | — | — | -0.34 | 0.62 |
| Ala | 103 | — | A | B | — | — | — | — | 0.04 | -0.24 | * | * | — | 0.43 | 0.67 |
| Pro | 104 | — | A | B | — | — | — | — | 0.40 | 0.00 | * | * | — | -0.30 | 0.30 |
| Phe | 105 | A | A | — | — | — | — | — | -0.41 | 0.00 | * | * | — | -0.30 | 0.78 |
| Glu | 106 | A | A | — | — | — | — | — | -0.66 | 0.04 | * | * | — | -0.30 | 0.64 |
| Val | 107 | A | A | — | — | — | — | — | 0.24 | 0.30 | * | * | — | -0.30 | 0.65 |
| Arg | 108 | A | A | — | — | — | — | — | 0.83 | -0.13 | * | * | — | 0.45 | 1.49 |
| Leu | 109 | A | A | — | — | — | — | — | 1.09 | -0.51 | — | * | — | 0.75 | 1.38 |
| Tyr | 110 | A | A | — | — | — | — | — | 1.79 | -0.51 | * | * | — | 0.75 | 3.73 |
| Lys | 111 | A | A | — | — | — | — | — | 1.19 | -1.16 | — | * | F | 0.90 | 3.18 |
| Asn | 112 | A | — | — | — | — | T | — | 1.16 | -0.54 | — | * | F | 1.30 | 3.82 |
| Lys | 113 | A | — | — | — | — | T | — | 1.04 | -0.54 | * | * | F | 1.30 | 1.71 |
| Asp | 114 | A | — | — | — | — | T | — | 1.54 | -0.90 | * | — | F | 1.30 | 1.48 |
| Met | 115 | — | — | B | — | — | T | — | 0.98 | -0.41 | * | — | — | 0.85 | 1.33 |
| Ile | 116 | — | — | B | B | — | — | — | 0.62 | -0.13 | * | — | — | 0.30 | 0.55 |
| Gln | 117 | — | — | B | B | — | — | — | 0.62 | 0.36 | * | — | — | -0.30 | 0.47 |
| Thr | 118 | A | — | — | B | — | — | — | 0.62 | 0.76 | * | — | F | -0.45 | 0.77 |
| Leu | 119 | A | — | — | B | — | — | — | 0.32 | 0.14 | * | — | F | 0.30 | 2.19 |
| Thr | 120 | A | — | — | B | — | — | — | 0.97 | -0.16 | * | * | F | 1.20 | 1.70 |
| Asn | 121 | — | — | — | — | T | T | — | 0.97 | -0.56 | — | * | F | 2.60 | 2.35 |
| Lys | 122 | — | — | — | — | T | T | — | 0.97 | -0.36 | — | * | F | 2.60 | 2.00 |
| Ser | 123 | — | — | — | — | T | — | C | 1.28 | -0.64 | — | * | F | 3.00 | 2.40 |
| Lys | 124 | — | — | B | — | — | T | — | 1.23 | -0.73 | — | * | F | 2.50 | 2.40 |
| Ile | 125 | — | — | B | — | — | — | — | 1.20 | -0.49 | — | * | F | 1.55 | 0.89 |
| Gln | 126 | — | — | B | — | — | — | — | 0.86 | -0.06 | — | — | F | 1.25 | 0.66 |
| Asn | 127 | — | — | B | — | — | T | — | 0.50 | -0.01 | * | * | F | 1.15 | 0.33 |
| Val | 128 | — | — | B | — | — | T | — | 0.56 | 0.47 | * | — | F | -0.05 | 0.67 |
| Gly | 129 | — | — | — | — | — | T | C | 0.51 | 0.54 | — | * | F | 0.15 | 0.61 |
| Gly | 130 | — | — | — | — | — | T | C | 0.59 | 0.14 | — | * | F | 0.45 | 0.65 |
| Thr | 131 | — | — | B | B | — | — | — | 0.56 | 0.43 | — | * | F | -0.45 | 0.73 |
| Tyr | 132 | — | — | B | B | — | — | — | -0.30 | 0.29 | — | * | — | -0.30 | 1.00 |
| Glu | 133 | — | — | B | B | — | — | — | 0.21 | 0.50 | — | * | — | -0.60 | 0.75 |
| Leu | 134 | — | — | B | B | — | — | — | 0.56 | 0.50 | — | — | — | -0.60 | 0.51 |
| His | 135 | — | — | B | — | — | T | — | 0.59 | 0.0.1 | * | * | — | 0.10 | 0.55 |
| Val | 136 | — | — | B | — | — | T | — | 0.01 | -0.26 | * | * | — | 0.70 | 0.46 |
| Gly | 137 | — | — | B | — | — | T | — | 0.26 | 0.43 | * | * | — | -0.20 | 0.39 |
| Asp | 138 | A | — | — | — | — | T | — | -0.56 | -0.26 | * | * | F | 0.85 | 0.48 |
| Thr | 139 | — | — | B | B | — | — | — | -0.63 | -0.07 | * | * | F | 0.45 | 0.53 |
| Ile | 140 | — | — | B | B | — | — | — | -1.30 | -0.03 | * | * | — | 0.30 | 0.37 |
| Asp | 141 | — | — | B | B | — | — | — | -0.44 | 0.33 | * | * | — | -0.30 | 0.19 |
| Leu | 142 | — | — | B | B | — | — | — | -0.40 | 0.73 | * | * | — | -0.60 | 0.22 |
| Ile | 143 | — | — | B | B | — | — | — | -0.40 | 0.63 | * | * | — | -0.60 | 0.41 |
| Phe | 144 | A | — | — | B | — | — | — | -0.12 | -0.06 | * | — | — | 0.30 | 0.43 |
| Asn | 145 | A | — | — | — | — | T | — | 0.77 | 0.44 | * | * | F | -0.05 | 0.71 |
| Ser | 146 | A | — | — | — | — | T | — | -0.09 | 0.16 | * | * | F | 0.40 | 1.75 |
| Glu | 147 | A | — | — | — | — | T | — | -0.09 | 0.11 | * | — | F | 0.40 | 1.50 |
| His | 148 | A | — | — | — | — | T | — | 0.84 | 0.01 | * | — | — | 0.10 | 0.77 |
| Gln | 149 | A | — | — | B | — | — | — | 1.54 | -0.39 | * | — | — | 0.45 | 1.15 |
| Val | 150 | A | — | — | B | — | — | — | 1.54 | -0.37 | * | — | — | 0.45 | 1.06 |
| Leu | 151 | — | — | B | B | — | — | — | 1.53 | 0.03 | — | — | — | -0.15 | 1.26 |
| Lys | 152 | — | — | B | B | — | T | — | 1.29 | 0.01 | * | — | F | 0.40 | 1.05 |
| Asn | 153 | — | — | — | — | T | — | — | 1.03 | 0.37 | * | — | F | 0.60 | 2.21 |
| Asn | 154 | — | — | — | — | T | T | — | 0.69 | 0.64 | * | — | F | 0.50 | 2.82 |
| Thr | 155 | — | — | — | — | T | T | — | 0.66 | 0.39 | — | — | F | 0.80 | 1.39 |
| Tyr | 156 | — | — | — | — | T | T | — | 0.58 | 1.07 | — | * | — | 0.20 | 0.61 |
| Trp | 157 | — | — | B | — | — | T | — | -0.28 | 1.36 | — | — | — | -0.20 | 0.27 |
| Gly | 158 | — | — | B | B | — | — | — | -1.09 | 1.64 | — | — | — | -0.60 | 0.15 |
| Ile | 159 | — | — | B | B | — | — | — | -1.68 | 1.84 | — | — | — | -0.60 | 0.08 |
| Ile | 160 | — | — | B | B | — | — | — | -1.37 | 1.59 | — | — | — | -0.60 | 0.08 |
| Leu | 161 | — | — | B | B | — | — | — | -1.33 | 1.07 | — | — | — | -0.60 | 0.12 |
| Leu | 162 | — | — | B | B | — | — | — | -1.04 | 1.07 | — | * | — | -0.60 | 0.27 |
| Ala | 163 | — | — | B | B | — | — | C | -1.40 | 0.79 | — | — | — | -0.40 | 0.68 |
| Asn | 164 | — | — | — | — | — | T | C | -1.40 | 0.89 | — | — | — | 0.00 | 0.71 |
| Pro | 165 | — | — | — | — | — | T | C | -0.81 | 0.89 | — | — | — | 0.00 | 0.61 |
| Gln | 166 | — | — | — | — | T | T | — | -0.39 | 0.59 | — | — | — | 0.20 | 0.80 |
| Phe | 167 | — | — | B | — | — | T | — | 0.03 | 0.51 | — | — | — | -0.20 | 0.64 |
| Ile | 168 | — | — | B | — | — | — | — | 0.23 | 0.54 | — | — | — | -0.40 | 0.53 |
| Ser | 169 | — | — | B | — | — | — | — | -0.16 | 0.54 | — | — | — | -0.40 | 0.39 |

Amino and Carboxy Terminal Deletions. As mentioned above, even if deletion of one or more amino acids from the N-terminus of a protein results in modification or loss of one or more biological functions of the protein, other biological activities may still be retained. Thus, the ability of shortened endokine alpha Madonnas to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an endokine alpha mutein with a large number of deleted N-terminal amino acid residues may retain some biological or immunogenic activities. In fact, peptides composed of as few as six endokine alpha amino acid residues may often evoke an immune response.

Accordingly, the present invention further provides polypeptides having one or more residues deleted from the amino terminus of the endokine alpha amino acid sequence shown in FIGS. 1A–1B (i.e., SEQ ID NO:2), up to the asparagine residue at position number 164 and polynucleotides encoding such polypeptides. In particular, the present invention provides polypeptides comprising the amino acid sequence of residues n-169 of FIGS. 1A–1B (SEQ ID NO:2), where n is an integer in the range of 2 to 164, and 165 is the position of the first residue from the N-terminus of the complete endokine alpha polypeptide believed to be required for at least immunogenic activity of the endokine alpha polypeptide.

More in particular, the invention provides polynucleotides encoding polypeptides comprising, or alternatively consisting of, the amino acid sequence of a member selected from the group consisting of: residues P-2 to S-169; L-3 to S-169; S-4 to S-169; H-5 to S-169; S-6 to S-169; R-7 to S-169; T-8 to S-169; Q-9 to S-169; G-10 to S-169; A-11 to S-169; Q-12 to S-169; R-13 to S-169; S-14 to S-169; S-15 to S-169; W-16 to S-169; K-17 to S-169; L-18 to S-169; W-19 to S-169; L-20 to S-169; F-21 to S-169; C-22 to S-169; S-23 to S-169; I-24 to S-169; V-25 to S-169; M-26 to S-169; L-27 to S-169; L-28 to S-169; F-29 to S-169; L-30 to S-169; C-31 to S-169; S-32 to S-169; F-33 to S-169; S-34 to S-169; W-35 to S-169; L-36 to S-169; I-37 to S-169; F-38 to S-169; I-39 to S-169; F-40 to S-169; L-41 to S-169; Q-42 to S-169; L-43 to S-169; E-44 to S-169; T-45 to S-169; A-46 to S-169; K-47 to S-169; E-48 to S-169; P-49 to S-169; C-50 to S-169; M-51 to S-169; A-52 to S-169; K-53 to S-169; F-54 to S-169; G-55 to S-169; P-56 to S-169; L-57 to S-169; P-58 to S-169; S-59 to S-169; K-60 to S-169; W-61 to S-169; Q-62 to S-169; M-63 to S-169; A-64 to S-169; S-65 to S-169; S-66 to S-169; E-67 to S-169; P-68 to S-169; P-69 to S-169; C-70 to S-169; V-71 to S-169; N-72 to S-169; K-73 to S-169; V-74 to S-169; S-75 to S-169; D-76 to S-169; W-77 to S-169; K-78 to S-169; L-79 to S-169; E-80 to S-169; I-81 to S-169; L-82 to S-169; Q-83 to S-169; N-84 to S-169; G-85 to S-169; L-86 to S-169; Y-87 to S-169; L-88 to S-169; I-89 to S-169; Y-90 to S-169; G-91 to S-169; Q-92 to S-169; V-93 to S-169; A-94 to S-169; P-95 to S-169; N-96 to S-169; A-97 to S-169; N-98 to S-169; Y-99 to S-169; N-100 to S-169; D-101 to S-169; V-102 to S-169; A-103to S-169; P-104 to S-169; F-105 to S-169; E-106 to S-169; V-107 to S-169; R-108 to S-169; L-109 to S-169; Y-110 to S-169; K-111 to S-169; N-112 to S-169; K-113 to S-169; D-114 to S-169; M-115 to S-169; I-116 to S-169; Q-117 to S-169; T-118 to S-169; L-119 to S-169; T-120 to S-169; N-121 to S-169; K-122 to S-169; S-123 to S-169; K-124 to S-169; I-125 to S-169; Q-126 to S-169; N-127 to S-169; V-128 to S-169; G-129 to S-169; G-130 to S-169; T-131 to S-169; Y-132 to S-169; E-133 to S-169; L-134 to S-169; H-135 to S-169; V-136 to S-169; G-137 to S-169; D-138 to S-169; T-139 to S-169; I-140 to S-169; D-141 to S-169; L-142 to S-169; I-143 to S-169; F-144 to S-169; N-145 to S-169; S-146 to S-169; E-147 to S-169; H-148 to S-169; Q-149 to S-169; V-150 to S-169; L-151 to S-169; K-152 to S-169; N-153 to S-169; N-154 to S-169; T-155 to S-169; Y-156 to S-169; W-157 to S-169; G-158 to S-169; I-159 to S-169; I-160 to S-169; L-161 to S-169; L-162 to S-169; A-163 to S-169; and N-164 to S-169 of the endokine alpha sequence shown in FIGS. 1A–1B. The present invention is also directed to nucleic acid molecules comprising or, alternatively, consisting of, a polynucleotide sequence at least 80%, 85%, 90%, 92%, 95%, 96%, 97%, 98% or 99% identical to the polynucleotide sequences encoding the endokine alpha polypeptides described above. The present invention also encompasses the above polynucleotide sequences fused to a heterologous polynucleotide sequence. Polypeptides encoded by these polynucleotide sequences are also encompassed by the invention.

Also as mentioned above, even if deletion of one or more amino acids from the C-terminus of a protein results in modification or loss of one or more biological functions of the protein, other biological activities may still be retained. Thus, the ability of the shortened endokine alpha mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an endokine alpha mutein with a large number of deleted C-terminal amino acid residues may retain some biological or immunogenic activities. In fact, peptides composed of as few as six endokine alpha amino acid residues may often evoke an immune response.

Accordingly, the present invention further provides polypeptides having one or more residues deleted from the carboxy terminus of the amino acid sequence of the endokine alpha polypeptide shown in FIGS. 1A–1B (SEQ ID NO:2), up to the serine residue at position number 6, and polynucleotides encoding such polypeptides. In particular, the present invention provides polypeptides comprising the amino acid sequence of residues 1-m of FIGS. 1A–1B (i.e., SEQ ID NO:2), where m is an integer in the range of 6 to 169, and 6 is the position of the first residue from the C-terminus of the complete endokine alpha polypeptide believed to be required for at least immunogenic activity of the endokine alpha polypeptide.

More in particular, the invention provides polynucleotides encoding polypeptides comprising, or alternatively consisting of, the amino acid sequence of a member selected from the group consisting of: residues M-1 to I-168; M-1 to F-167; M-1 to Q-166; M-1 to P-165; M-1 to N-164; M-1 to A-163; M-1 to L-162; M-1 to L-161; M-1 to I-160; M-1 to I-159; M-1 to G-158; M-1 to W-157; M-1 to Y-156; M-1 to T-155; M-1 to N-154; M-1 to N-153; M-1 to K-152; M-1 to L-151; M-1 to V-150; M-1 to Q-149; M-1 to H-148; M-1 to E-147; M-1 to S-146; M-1 to N-145; M-1 to F-144; M-1 to I-143; M-1 to L-142; M-1 to D-141; M-1 to I-140; M-1 to T-139; M-1 to D-138; M-1 to G-137; M-1 to V-136; M-1 to H-135; M-1 to L-134; M-1 to E-133; M-1 to Y-132; M-1 to T-131; M-1 to G-130; M-1 to G-129; M-1 to V-128; M-1 to N-127; M-1 to Q-126; M-1 to I-125; M-1 to K-124; M-1 to S-123; M-1 to K-122; M-1 to N-121; M-1 to T-120; M-1 to L-119; M-1 to T-118; M-1 to Q-117; M-1 to I-116; M-1 to M-115; M-1 to D-114; M-1 to K-113; M-1 to N-112; M-1 to K-111; M-1 to Y-110; M-1 to L-109; M-1 to R-108; M-1 to V-107; M-1 to E-106; M-1 to F-105; M-1 to P-104; M-1 to A-103; M-1 to V-102; M-1 to D-101; M-1 to N-100; M-1 to Y-99; M-1 to N-98; M-1 to A-97; M-1 to N-96; M-1 to P-95; M-1 to A-94; M-1 to V-93; M-1 to Q-92; M-1 to G-91; M-1 to Y-90; M-1 to I-89; M-1 to L-88; M-1 to Y-87; M-1 to L-86; M-1 to G-85; M-1 to N-84; M-1 to Q-83; M-1 to L-82; M-1 to I-81; M-1 to E-80; M-1 to L-79; M-1 to K-78; M-1 to W-77; M-1 to D-76; M-1 to S-75; M-1 to V-74; M-1 to K-73; M-1 to N-72; M-1 to V-71; M-1 to C-70; M-1 to P-69; M-1 to P-68; M-1 to E-67; M-1 to S-66; M-1 to S-65; M-1 to A-64; M-1 to M-63; M-1 to Q-62; M-1 to W-61; M-1 to K-60; M-1 to S-59; M-1 to P-58; M-1 to L-57; M-1 to P-56; M-1 to G-55; M-1 to F-54; M-1 to K-53; M-1 to A-52; M-1 to M-51; M-1 to C-50; M-1 to P-49; M-1 to E-48; M-1 to K-47; M-1 to A-46; M-1 to T-45; M-1 to E-44; M-1 to L-43; M-1 to Q-42; M-1 to L-41; M-1 to F-40; M-1 to I-39; M-1 to F-38; M-1 to I-37; M-1 to L-36; M-1 to W-35; M-1 to S-34; M-1 to F-33; M-1 to S-32; M-1 to C-31; M-1 to L-30; M-1 to F-29; M-1 to L-28; M-1 to L-27; M-1 to M-26; M-1 to V-25; M-1 to I-24; M-1 to S-23; M-1 to C-22; M-1 to F-21; M-1 to L-20; M-1 to W-19; M-1 to L-18; M-1 to K-17; M-1 to W-16; M-1 to S-15; M-1 to S-14; M-1 to R-13; M-1 to Q-12; M-1 to A-11; M-1 to G-10; M-1 to Q-9; M-1 to T-8; M-1 to R-7; and M-1 to S-6 of the sequence of the endokine alpha sequence shown in FIGS. 1A–1B. The present invention is also directed to nucleic acid molecules comprising or, alternatively, consisting of, a polynucleotide sequence at least 80%, 85%, 90%, 92%, 95%, 96%, 97%, 98% or 99% identical to the polynucleotide sequences encoding the endokine alpha polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of an endokine alpha polypeptide, which may be described generally as having residues n–m of FIGS. 1A–1B (i.e., SEQ ID NO:2), where n and m are integers as described above.

The endokine alpha polypeptides of the invention may be in monomers or multimers (i.e., dimers, trimers, tetramers and higher multimers). Accordingly, the present invention relates to monomers and multimers of the endokine alpha polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only endokine alpha polypeptides of the invention (including endokine alpha fragments, variants, and fusion proteins, as described herein). These homomers may contain endokine alpha polypeptides having identical or different amino acid sequences. In a specific embodiment, a homomer of the invention is a multimer containing only endokine alpha polypeptides having an identical amino acid sequence. In another specific embodiment, a homomer of the invention is a multimer containing endokine alpha polypeptides having different amino acid sequences. In specific embodiments, the multimer of the invention is a homodimer (e.g., containing endokine alpha polypeptides having identical or different amino acid sequences) or a homotrimer (e.g., containing endokine alpha polypeptides having identical or different amino acid sequences). In additional embodiments, the homomeric multimer of the invention is at least a homodimer, at least a homotrimer, or at least a homotetramer.

As used herein, the term heteromer refers to a multimer containing heterologous polypeptides (i.e., polypeptides of a different protein) in addition to the endokine alpha fragments and endokine alpha polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the endokine alpha polypeptides of the invention. Such covalent associations may involve one or more amino acid residues contained in the polypeptide sequence (e.g., that recited in SEQ ID NO:2, or contained in the polypeptide encoded by the clone 97640). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in an endokine alpha fusion protein. In one example, covalent associations are between the heterologous sequence contained in a fusion protein of the invention (see, e.g., U.S. Pat. No. 5,478,925). In a specific example, the covalent associations are between the heterologous sequence contained in a endokine alpha-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in its entirety).

In another embodiment, two or more endokine alpha polypeptides of the invention are joined through peptide linkers. Examples include those peptide linkers described in U.S. Pat. No. 5,073,627 (hereby incorporated by reference). Proteins comprising multiple endokine alpha polypeptides separated by peptide linkers may be produced using conventional recombinant DNA technology.

Another method for preparing multimer endokine alpha polypeptides of the invention involves use of endokine alpha polypeptides fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric endokine alpha proteins are those described in PCT application WO 94/10308, hereby incorporated by reference. Recombinant fusion proteins comprising a soluble endokine alpha polypeptide fused to a peptide that dimerizes or trimerizes in solution are expressed in suitable host cells, and the resulting soluble multimeric endokine alpha is recovered from the culture supernatant using techniques known in the art.

Certain members of the TNF family of proteins are believed to exist in trimeric form (Beutler and Huffel, *Science* 264:667, 1994; Banner et al., *Cell* 73:431, 1993). Thus, trimeric endokine alpha may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, hereby incorporated by reference. Other peptides derived from naturally occurring trimeric proteins may be employed in preparing trimeric endokine alpha.

In another example, proteins of the invention are associated by interactions between Flag® polypeptide sequence contained in Flag®-endokine alpha fusion proteins of the invention. In a further embodiment, associations proteins of the invention are associated by interactions between a heterologous polypeptide sequence contained in Flag®-endokine alpha fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In addition, polypeptides of the invention can be chemically synthesized using techniques known in the art (e.g., see Creighton, 1983, Proteins: Structures and Molecular Principles, W. H. Freeman & Co., N.Y., and Hunkapiller, M., et al., 1984, Nature 310:105–111). For example, a peptide corresponding to a fragment of the endokine alpha polypeptides of the invention can be synthesized by use of a peptide synthesizer. Furthermore, if desired, nonclassical amino acids or chemical amino acid analogs can be introduced as a substitution or addition into the endokine alpha polynucleotide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses endokine alpha polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of endokine alpha which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the present invention have uses which include, but are not limited to, as sources for generating antibodies that bind the polypeptides of the invention, and as molecular weight markers on SDS-PAGE gels or on molecular sieve gel filtration columns using methods well known to those of skill in the art.

Protein Modification

In addition, proteins of the invention can be chemically synthesized using techniques known in the art (see, e.g., Creighton, Proteins: Structures and Molecular Principles, W. H. Freeman & Co., N.Y. (1983), and Hunkapiller, M., et al., Nature 310:105–111 (1984)). For example, a peptide corresponding to a fragment of the endokine-alpha polypeptides of the invention can be synthesized by use of a peptide synthesizer. Furthermore, if desired, nonclassical amino acids or chemical amino acid analogs can be introduced as a substitution or addition into the endokine-alpha polypeptide sequence. Non-classical amino acids include, but are not limited to, to the D-isomers of the common amino acids, 2,4-diaminobutyric acid, alpha-amino isobutyric acid, 4-aminobutyric acid, Abu, 2-amino butyric acid, alpha-Abu, alpha-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alpha-alanine, fluoroamino acids, designer amino acids such as alpha-methyl amino acids, Ca-methyl amino acids, Na-methyl amino acids, and amino acid analogs in general. Furthermore, the amino acids can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., Nucl. Acids Res. 13:4331 (1986); and Zoller et al., Nucl. Acids Res. 10:6487 (1982)), cassette mutagenesis (see, e.g., Wells et al., Gene 34:315 (1985)), and restriction selection mutagenesis (see, e.g., Wells et al., Philos. Trans. R. Soc. London SerA 317:415 (1986)).

The invention additionally, encompasses endokine-alpha polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of endokine alpha which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on the functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

Antibodies and Epitopes

As described in detail below, the polypeptides of the present invention can be used to raise polyclonal and monoclonal antibodies, which are useful in diagnostic assays for detecting endokine alpha protein expression as described below or as agonists and antagonists capable of inhibiting endokine alpha protein function. Further, such polypeptides can be used in the yeast two-hybrid system to "capture" endokine alpha protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., *Proc. Natl. Acad. Sci. USA* 81:3998–4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 30 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes posttranslational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A. et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides that can be used to generate endokine-specific polyclonal and monoclonal antibodies include a polypeptide comprising or, alternatively, consisting of one, two, three or more of any of the following amino acid sequences and polynucleotides encoding these polypeptides: amino acid residues from about 44 to about 158 in FIGS. 1A–1B (SEQ ID NO:2); amino acid residues from about 44 to about 54 in FIGS. 1A–1B (SEQ ID NO:2); amino acid residues from about 57 to about 68 in FIGS. 1A–1B (SEQ ID NO:2); amino acid residues from about 69 to about 78 in FIGS. 1A–1B (SEQ ID NO:2); amino acid residues from about 94 to about 105 in FIGS. 1A–1B (SEQ ID NO:2); amino acid residues from about 108 to about 132 in FIGS. 1A–1B (SEQ ID NO:2); and amino acid residues from about 148 to about 158 in FIGS. 1A–1B (SEQ ID NO:2). As indicated above, the inventors have determined that the above polypeptide fragments are antigenic regions of the endokine alpha protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. See, Houghten, R. A., *Proc. Natl. Acad Sci. USA* 82:5131–5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemocyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde.

Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al. (1984), supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art.

For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention which include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes monoclonal, polyclonal, chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g, WO 93/17715; WO 92/08802; WO 91/00360; WO 92/05793; Tutt, A. et al. (1991) *J. Immunol.* 147:60–69; U.S. Pat. Nos. 5,573,920, 4,474,893, 5,601,819, 4,714,681, 4,925,648; Kostelny, S. A. et al. (1992) *J. Immunol.* 148:1547–1553.

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies: A Laboratory Manual*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; and WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "monoclonal antibody" refers to an antibody that is derived from a single clone, including any eukaryotic, prokaryotic, or phage clone, and not to the method by which it is produced. Monoclonal antibodies can be prepared using a wide variety of techniques known in the art including the use of hybridoma, recombinant and phage display technology.

Hybridoma techniques include those known in the art and taught in Harlow et al., *Antibodies: A Laboratory Manual* (Cold Spring Harbor Laboratory Press, 2nd ed. 1988); Hammerling, et al., in: *Monoclonal Antibodies and T-cell Hybridomas*, pp. 563–681 (Elsevier, N.Y., 1981) (said references incorporated by reference in their entireties).

Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41–50; Ames, R. S. et al. (1995) J. Immunol. Methods 184:177–186; Kettleborough, C. A. et al. (1994) Eur. J. Immunol. 24:952–958; Persic, L. et al. (1997) Gene 187 9–18; Burton, D. R. et al. (1994) Advances in Immunology 57:191–280; PCT/GB91/01134; WO 90/02809; WO 91/10737; WO 92/01047; WO 92/18619; WO 93/11236; WO 95/15982; and WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al., *BioTechniques* 12(6):864–869 (1992); and Sawai, H. et al., *AJRI* 34:26–34 (1995); and Better, M. et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu, L. et al., *PNAS* 90:7995–7999 (1993); and Skerra, A. et al., *Science* 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, *Science* 229:1202 (1985); Oi et al., *BioTechniques* 4:214 (1986); Gillies, S. D. et al., *J. Immunol. Methods* 125:191–202 (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., *Molecular Immunology* 28(4/5):489–498 (1991); Studnicka G. M. et al., *Protein Engineering* 7(6):805–814 (1994); Roguska M. A. et al., *PNAS* 91:969–973 (1994)), and chain shuffling (U.S. Pat. No. 5,565,332). Human antibodies can be made by a variety of methods known in the art including phage display methods described above. See also U.S. Pat. Nos. 4,444,887, 4,716,111, 5,545, 806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al., *Immunol. Lett.* 39:91–99 (1994); U.S. Pat. No. 5,474,981; Gillies, S. O. et al., *PNAS* 89:1428–1432 (1992); Fell, H. P. et al., *J. Immunol.* 146:2446–2452(1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al., *PNAS* 88:10535–10539 (1991); Zheng, X. X. et al., *J. Immunol.* 154:5590–5600 (1994); and Vil, H. et al., *PNAS* 89:11337–11341 (1992) (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al., *Blood* 92(6) :1981–1988 (1998); Chen, Z. et al., *Cancer Res.* 58(16) :3668–3678 (1998); Harrop, J. A. et al., *J. Immunol.* 161(4) :1786–1794 (1998); Zhu, Z. et al., *Cancer Res.* 58(15) :3209–3214 (1998); Yoon, D. Y. et al., *J. Immunol.* 160(7) :3170–3179(1998); Prat, M. et al., *J. Cell. Sci.* 111(Pt2) :237–247 (1998); Pitard, V. et al., *J. Immunol. Methods* 205(2):177–190 (1997); Liautard, J. et al, *Cytokine* 9(4) :233–241 (1997); Carlson, N. G. et al., *J. Biol. Chem.* 272(17):11295–11301 (1997); Taryman, R. E. et al., *Neuron* 14(4):755–762 (1995); Muller, Y. A. et al., *Structure* 6(9) :1153–1167 (1998); Bartunek, P. et al., *Cytokine* 8(1):14–20 (1996)(said references incorporated by reference in their entireties).

The entire disclosure of each document cited in this section on "Polypeptides and Peptides" is hereby incorporated herein by reference.

Epitopes

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in deposited clone [Deposit information] or encoded by a polynucleotide that hybridizes to the complement of the sequence of SEQ ID NO:1 or contained in the clone deposited as ATCC Deposit Number 97640 on Jun. 27, 1996 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., *Proc. Natl. Acad. Sci. USA* 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding, but does not necessarily exclude cross-reactivity with other antigens. Antigenic epitopes need not necessarily be immunogenic.

Fragments that function as epitopes may be produced by any conventional means. (See, e.g., Houghten, *Proc. Natl. Acad. Sci. USA* 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, e.g., Wilson et al., *Cell* 37:767–778 (1984); Sutcliffe et al., *Science* 219:660–666 (1983)).

Similarly, immunogenic epitopes can be used, for example, to induce antibodies according to methods well known in the art. (See, e.g., Sutcliffe et al., supra; Wilson et al., supra; Chow et al., *Proc. Natl. Acad. Sci USA* 82:910–914; and Bittle et al., *J. Gen. Virol.* 66:2347–2354 (1985). A preferred immunogenic epitope includes the secreted protein. The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.* 66:2347–2354(1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected by, for example, ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, and IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature* 331:84–86 (1988). IgG fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., *J. Biochem.* 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., *Proc. Natl. Acad. Sci. USA* 88:8972–897 (1991)). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., *Curr. Opinion Biotechnol.* 8:724–33 (1997); Harayama, *Trends Biotechnol.* 16(2):76–82 (1998); Hansson, et al., *J. Mol. Biol.* 287:265–76 (1999); and Lorenzo and Blasco, *Biotechniques* 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; and WO 92/05793; Tutt, et al., *J. Immunol.* 147:60–69 (1991); U.S. Pat. Nos. 4,474,893; 4,714,681; 4,925,648; 5,573,920; and 5,601,819; Kostelny et al., *J. Immunol.* 148:1547–1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$M, $10^{-2}$M, $5 \times 10^{-3}$M, $10^{-3}$M, $5 \times 10^{-4}$M, $10^{-4}$M, $5 \times 10^{-5}$M, $10^{-5}$M, $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding, but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., *Blood* 92(6):1981–1988 (1998); Chen, et al., *Cancer Res.* 58(16):3668–3678 (1998); Harrop et al., *J. Immunol.* 161(4):1786–1794 (1998); Zhu et al., *Cancer Res.* 58(15):3209–3214 (1998); Yoon, et al., *J. Immunol.* 160(7):3170–3179 (1998); Prat et al., *J. Cell. Sci.* 111(Pt2):237–247 (1998); Pitard et al., *J. Immunol. Methods* 205(2):177–190 (1997); Liautard et al., *Cytokine* 9(4):233–241 (1997); Carlson et al., *J. Biol. Chem.* 272(17)

:11295–11301 (1997); Taryman et al., *Neuron* 14(4) :755–762 (1995); Muller et al., *Structure* 6(9):1153–1167 (1998); Bartunek et al., *Cytokine* 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies: A Laboratory Manual* (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; and WO 89/12624; U.S. Pat. No. 5,314,995; and EP 396,387.

The antibodies of the invention include derivatives that are modified, e.g., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual* (Cold Spring Harbor Laboratory Press, 2nd ed. 1988); Hammerling, et al., in: *Monoclonal Antibodies and T-Cell Hybridomas* 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well-known in the art and are discussed in detail in Example 3. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface ofphage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41–50 (1995); Ames et al., *J. Immunol. Methods* 184:177–186 (1995); Kettleborough et al., *Eur. J. Immunol.* 24:952–958 (1994); Persic et al., *Gene* 187:9–18 (1997); Burton et al., *Advances in Immunology* 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426;

5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864–869 (1992); and Sawai et al., *AJRI* 34:26–34 (1995); and Better et al., *Science* 240:1041 –1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986); Gillies et al., *J. Immunol. Methods* 125:191–202(1989); U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, *Molecular Immunology* 28(4/5):489–498 (1991); Studnicka et al., *Protein Engineering* 7(6):805–814 (1994); Roguska. et al., *PNAS* 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (*Int. Rev. Immunol.* 13:65–93 (1995)). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7(5):437–444 (1989) and Nissinoff, *J. Immunol.* 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated therefrom, or nucleic acid, preferably poly A+RNA, isolated therefrom, or any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (See, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.* 278:457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851–855 (1984); Neuberger et al., *Nature* 312:604–608 (1984); Takeda et al., *Nature* 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423–42; Huston et al., *Proc. Natl. Acad. Sci. USA* 85:5879–5883 (1988); and Ward et al., *Nature* 334:544–54(1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., *Science* 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter.

Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the E. coli expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (*Clinical Pharmacy* 12:488–505; Wu and Wu, *Biotherapy* 3:87–95 (1991); Tolstoshev, *Ann. Rev. Pharmacol. Toxicol.* 32:573–596 (1993); Mulligan, *Science* 260:926–932 (1993); and Morgan and Anderson, *Ann. Rev. Biochem.* 62:191–217 (1993); *TIB TECH* 11(5):155–215 (May 1993)); and hygro, which confers resistance to hygromycin (Santerre et al., 1984, Gene 30:147). Methods commonly known in the art of recombinant DNA technology which can be used are described in Ausubel et al., eds., *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al., eds, *Current Protocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells," in *DNA Cloning*, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., *Nature* 331:84–86(1988)). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., *J. Biochem.* 270:3958–3964(1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., *J. Molecular Recognition* 8:52–58 (1995); K. Johanson et al., *J. Biol. Chem.* 270:9459–9471 (1995).

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 3 7:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. eds., pp. 243–56 (Alan R. Liss, Inc. 1985); Hellstrom et al., "Antibodies For Drug Delivery", in *Controlled Drug Delivery* (2nd Ed.), Robinson et al. (eds.), pp. 623–53 (Marcel Dekker, Inc. 1987); Thorpe, "Antibody Carriers Of Cytotoxic Agents In Cancer Therapy: A Review", in *Monoclonal Antibodies '84: BiologicalAnd Clinical Applications*, Pinchera et al. eds., pp. 475–506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. eds., pp. 303–16 (Academic Press 1985), and Thorpe et al., "The Preparation And Cytotoxic Properties Of Antibody-Toxin Conjugates", *Immunol. Rev.* 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays For Antibody Binding

The antibodies of the invention may be assayed for immunospecific binding by any method known in the art.

The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, *Current Protocols in Molecular Biology*, Vol. 1, John Wiley & Sons, Inc., New York (1994), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel (et al., eds, *Current Protocols in Molecular Biology*, Vol. 1, John Wiley & Sons, Inc., New York (19914) at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel, et al., eds, *Current Protocols in Molecular Biology*, Vol. 1, John Wiley & Sons, Inc., New York (1994) at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel, et al., eds, *Current Protocols in Molecular Biology*, Vol. 1, John Wiley & Sons, Inc., New York (1994) at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., 3H or 125I) in the presence of increasing amounts of an unlabeled second antibody.

Endokine Alpha Related Disorder Diagnosis

Endokine alpha is a new member of the TNF family of cytokines. For endokine alpha related disorders, it is believed that substantially altered (increased or decreased) levels of endokine alpha gene expression can be detected in tissue or other cells or bodily fluids (e.g., sera, plasma, urine, synovial fluid or spinal fluid) taken from an individual having such a disorder, relative to a "standard" endokine alpha gene expression level, that is, the endokine alpha expression level in tissue or bodily fluids from an individual not having the disorder. Thus, the invention provides a diagnostic method useful during diagnosis of an endokine alpha-related disorder, which involves measuring the expression level of the gene encoding the endokine alpha protein in tissue or other cells or body fluid from an individual and comparing the measured gene expression level with a standard endokine alpha gene expression level, whereby an increase or decrease in the gene expression level compared to the standard is indicative of an endokine alpha related disorder.

By individual is intended mammalian individuals, preferably humans. By "measuring the expression level of the gene encoding the endokine alpha protein" is intended qualitatively or quantitatively measuring or estimating the level of the endokine alpha protein or the level of the mRNA encoding the endokine alpha protein in a first biological sample either directly (e.g., by determining or estimating absolute protein level or mRNA level) or relatively (e.g., by comparing to the endokine alpha protein level or mRNA level in a second biological sample). Preferably, the endokine alpha protein level or mRNA level in the first biological sample is measured or estimated and compared to a standard endokine alpha protein level or mRNA level, the standard being taken from a second biological sample obtained from an individual not having the disorder or being determined by averaging levels from a population of individuals not having a disorder involving endokine alpha. As will be appreciated in the art, once a standard endokine alpha protein level or mRNA level is known, it can be used repeatedly as a standard for comparison.

By "biological sample" is intended any biological sample obtained from an individual, body fluid, cell line, tissue culture, or other source which contains endokine alpha protein or mRNA. As indicated, biological samples include body fluids (such as sera, plasma, urine, synovial fluid and spinal fluid) which contain secreted mature endokine alpha protein, or tissue sources found to express endokine alpha. Methods for obtaining tissue biopsies and body fluids from mammals are well known in the art. Where the biological sample is to include mRNA, a tissue biopsy is the preferred source.

The present invention is useful for diagnosis of various endokine alpha related disorders in mammals, preferably humans, as similar to TNF-like disorders known in the art or as presented herein. These include disorders associated with immunomodulation and inflammation, cell proliferation, angiogenesis, tumor metastases, apoptosis, sepsis and endotoxemia.

Total cellular RNA can be isolated from a biological sample using any suitable technique such as the single-step-guanidinium-thiocyanate-phenol-chloroform method described in Chomczynski and Sacchi, *Anal. Biochem.* 162:156–159(1987). Levels of mRNA encoding an endokine alphapolypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Endokine alpha protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the endokine alpha protein). Northern blot analysis can be performed as described above.

Preferably, levels of mRNA encoding the endokine alpha protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the endokine alpha protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying endokine alpha protein levels in a biological sample can occur using any art-known method. Preferred for assaying endokine alphaprotein levels in a biological sample are antibody-based techniques. For example, endokine alpha protein expression in tissues can be studied with classical immunohistological methods. In these, the specific recognition is provided by the primary antibody (polyclonal or monoclonal), but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of endokine alpha protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of endokine alpha protein can be accomplished using isolated endokine alpha protein as a standard. This technique can also be applied to body fluids. With these samples, a molar concentration of endokine alpha protein will aid to set standard values of endokine alpha protein content for different body fluids, like serum, plasma, urine, synovial fluid, spinal fluid, etc. The normal appearance of endokine alpha protein amounts can then be set using values from healthy individuals, which can be compared to those obtained from a test subject.

Other antibody-based methods useful for detecting endokine alpha protein levels include immunoassays, such as the enzyme linked immunosorbent assay (ELISA) and the radioimmunoassay (RIA). For example, endokine alpha protein-specific monoclonal antibodies can be used both as an immunoadsorbent and as an enzyme-labeled probe to detect and quantify the endokine alpha protein. The amount of endokine alpha protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect endokine alpha protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting endokine alpha protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides. enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying endokine alpha protein levels in a biological sample obtained from an individual, endokine alpha protein can also be detected in vivo by imaging. Antibody labels or markers for in vivo imaging of endokine alpha protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A endokine alpha protein-specific antibody or antibody portion which has been labeled with an appropriate detectable imaging moiety, such as a radioisotope (for example, $^{131}$I, $^{111}$In, $^{99m}$Tc), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}$Tc. The labeled antibody or antibody portion will then preferentially accumulate at the location of cells which contain endokine alpha protein. In vivo tumor imaging is described in S. W. Burchiel et al., "Immunopharmacokinetics of Radiolabeled Antibodies and Their Portions" (Chapter 13 in *Tumor Imaging: The Radiochemical Detection of Cancer*, Burchiel, S. W. and Rhodes, B. A. eds., Masson Publishing Inc. (1982)).

Endokine alpha-protein specific antibodies for use in the present invention can be raised against the intact endokine alpha protein or an antigenic polypeptide portion thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody portions (such as, for example, Fab and F(ab')$_2$ portions) which are capable of specifically binding to endokine alpha protein. Fab and F(ab')$_2$ portions lack the Fc portion of intact antibody, clear more rapidly from the circulation, and may have less non-specific tissue binding of an intact antibody (Wahl et al., *J. Nucl. Med.* 24:316–325 (1983)). Thus, these portions are preferred.

The antibodies of the present invention may be prepared by any of a variety of methods. For example, cells expressing the endokine alpha protein or an antigenic portion thereof can be administered to an animal in order to induce the production of sera containing polyclonal antibodies. In a preferred method, a preparation of endokine alpha protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies (or endokine alpha protein binding portions thereof). Such monoclonal antibodies can be prepared using hybridoma technology (see, e.g., Colligan, *Current Protocols in Immunology*, Wiley Interscience, New York (1990–1996); Harlow & Lane, *Antibodies: A Laboratory Manual*, Chs. 6–9, Cold Spring Harbor Press, Cold Spring Harbor, N.Y. (1988); Ausubel, infra, at Chapter 11, these references entirely incorporated herein by reference).

In general, such procedures involve immunizing an animal (preferably a mouse) with an endokine alpha polypeptide antigen or with an endokine alpha polypeptide-expressing cell. Suitable cells can be recognized by their capacity to bind anti-endokine alpha protein antibody. Such cells may be cultured in any suitable tissue culture medium (e.g., Earle's modified Eagle's medium supplemented with 10% fetal bovine serum (inactivated at about 56° C.), supplemented with about 10 μg/l of nonessential amino acids, about 1,000 U/ml of penicillin, and about 100 μg/ml of streptomycin). The splenocytes of such mice are extracted and fused with a suitable myeloma cell line. Any suitable myeloma cell line may be employed in accordance with the present invention (e.g., parent myeloma cell line (SP$_2$O), available from the American Type Culture Collection (ATCC) (Manassas, Va., USA)). After fusion, the resulting hybridoma cells are selectively maintained in HAT medium, and then cloned by limiting dilution as described by Wands et al., *Gastroenterology* 80:225–232 (1981); Harlow & Lane, infra, Chapter 7. The hybridoma cells obtained through such a selection are then assayed to identify clones which secrete antibodies capable of binding the endokine alpha antigen.

Alternatively, additional antibodies capable of binding to the endokine alpha protein antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, endokine alpha protein specific antibodies are used to immunize an animal, preferably a mouse. The splenocytes of such an animal are then used to produce hybridoma cells, and the hybridoma cells are screened to identify clones which produce an antibody whose ability to bind to the endokine alpha protein-specific antibody can be blocked by the endokine alpha protein antigen. Such antibodies comprise anti-idiotypic antibodies to the endokine alpha protein-specific antibody and can be used to immunize an animal to induce formation of further endokine alpha protein-specific antibodies.

It will be appreciated that Fab and F(ab')$_2$ and other portions of the antibodies of the present invention may be used according to the methods disclosed herein. Such portions are typically produced by proteolytic cleavage, using enzymes such as papain (to produce Fab portions) or pepsin (to produce F(ab')$_2$ portions). Alternatively, endokine alpha protein-binding portions can be produced through the application of recombinant DNA technology or through synthetic chemistry.

Where in vivo imaging is used to detect enhanced levels of endokine alpha protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al, Nature 312:643 (1984); Neuberger et al., Nature 314:268 (1985).

Further suitable labels for the endokine alpha protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In and $^{99m}$Tc are preferred isotopes where in vivo imaging is used since they avoid the problem of dehalogenation of the $^{125}$I or $^{131}$I-labeled monoclonal antibody by the liver. In addition, these radionucleotides have a more favorable gamma emission energy for imaging (Perkins et al., Eur. J. Nucl. Med. 10:296–301 (1985); Carasquillo et al., J. Nucl. Med. 28:281–287 (1987)). For example, $^{111}$In coupled to monoclonal antibodies with 1-(p-isothiocyanatobenzyl)-DPTA has shown little uptake in non-tumorous tissues, particularly the liver, and therefore enhances specificity of tumor localization (Esteban et al., J. Nucl. Med. 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al. (Clin. Chim. Acta 70:1–31 (1976)), and Schurs et al. (Clin. Chim. Acta 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, IgM, and IgY. As used herein, the term "antibody" (Ab) is meant to include whole antibodies, including single-chain whole antibodies, and antigen-binding fragments thereof Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al., J. Immunol. 147:60–69 (1991); U.S. Pat. Nos. 5,573,920, 4,474,893, 5,601,819, 4,714,681, 4,925,648; Kostelny, S. A. et al., J. Immunol. 148:1547–1553 (1992). Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies: A Laboratory Manual*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. Monoclonal antibodies can be prepared using a wide of techniques known in the art including the use of hybridoma and recombinant technology. See, e.g., Harlow et al., *Antibodies: A Laboratory Manual*, (Cold Spring Harbor Laboratory Press, 2nd ed. 1988); Hammerling, et al., in: *Monoclonal Antibodies and T-cell Hybridomas*, pp. 563–681 (Elsevier, N.Y., 1981) (said references incorporated by reference in their entireties).

Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al., *J. Immunol. Methods* 182:41–50 (1995); Ames, R. S. et al., *J. Immunol. Methods* 184:177–186 (1995); Kettleborough, C. A. et al., *Eur. J. Immunol.* 24:952–958 (1994); Persic, L. et al., *Gene* 187:9–18 (1997); Burton, D. R. et al., *Advances in Immunology* 57:191–280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al., *BioTechniques* 12(6):864–869 (1992); and Sawai, H. et al., *AJRI* 34:26–34 (1995); and Better, M. et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46–88; Shu, L. et al., *PNAS* 90:7995–7999 (1993); and Skerra, A. et al., *Science* 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, *Science* 229:1202 (1985); Oi et al., *BioTechniques* 4:214 (1986); Gillies, S. D. et al., *J. Immunol. Methods* 125:191–202 (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585, 089), veneering or resurfacing (EP 0 592 106; EP 0 519 596; Padlan E. A., *Molecular Immunology* 28(4/5):489–498 (1991); Studnicka G. M. et al., *Protein Engineering* 7(6):805–814 (1994); Roguska M. A. et al., *PNAS* 91:969–973) (1994), and chain shuffling (U.S. Pat. No. 5,565,332). Human antibodies can be made by a variety of methods known in the art including phage display methods described above. See also, U.S. Pat. Nos. 4,444,887, 4,716, 111, 5,545,806, and 5,814,318; and WO 98/46645 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al., *Immunol. Lett.* 39:91–99 (1994); U.S. Pat. No. 5,474, 981; Gillies, S. O. et al., *PNAS* 89:1428–1432 (1992); Fell, H. P. et al., *J. Immunol.* 146:2446–2452 (1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al., *PNAS* 88:10535–10539 (1991); Zheng, X. X. et al., *J. Immunol.* 154:5590–5600 (1995); and Vil, H. et al., *PNAS* 89:11337–11341 (1992) (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding, but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. see e.g., WO 96/40281; U.S. Pat. No. 5,811,097; Deng, B. et al., *Blood* 92(6):1981–1988 (1998); Chen, Z. et al., *Cancer Res.* 58(16):3668–3678 (1998); Harrop, J. A. et al., *J. Immunol.* 161(4):1786–1794 (1998); Zhu, Z. et al., *Cancer Res.* 58(15):3209–3214 (1998); Yoon, D. Y. et al., *J. Immunol.* 160(7):3170–3179 (1998); Prat, M. et al., *J. Cell. Sci.* 111(Pt2):237–247 (1998); Pitard, V. et al., *J. Immunol. Methods* 205(2):177–190 (1997); Liautard, J. et al., *Cytokinde* 9(4):233–241 (1997); Carlson, N. G. et al., *J. Biol. Chem.* 272(17):11295–11301 (1997); Taryman, R. E. et al., *Neuron* 14(4):755–762 (1995); Muller, Y. A. et al., *Structure* 6(9):1153–1167 (1998); Bartunek, P. et al., *Cytokine* 8(1):14–20 (1996) (said references incorporated by reference in their entireties).

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology* (NY) 11:1263–1270 (1993); Wright et al., *Biotechnology* (NY) 9:830–834(1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, *Intl. Rev. Cytol.* 115:171–229 (1989), which is incorporated by reference herein in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature 385:810–813* (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu el al. (Gu et al., *Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product. Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of endokine alpha polypeptides, studying conditions and/or disorders associated with aberrant endokine alpha expression, and in screening for compounds effective in ameliorating such conditions and/or disorders.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety. See also U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Antagonists

In specific embodiments, antagonists according to the present invention are nucleic acids corresponding to the sequences contained in SEQ ID NO:1, or the complementary strand thereof, and/or to nucleotide sequences contained in the deposited clone 97640. In one embodiment, antisense sequence is generated internally by the organism, in another embodiment, the antisense sequence is separately administered (see, for example, O'Connor, J., *Neurochem.* 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., *Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the endokine alpha antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the endokine alpha antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding endokine alpha, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304–310(1981), the promoter contained in the 3' long terminal repeat of Rous sarcoma virus (Yamamoto et al., *Cell* 22:787–797 (1980), the herpes thymidine promoter (Wagner et al., *Proc. Natl. Acad. Sci. U.S.A.* 78:1441–1445 (1981), the regulatory sequences of the metallothionein gene (Brinster, et al., *Nature* 296:39–42 (1982)), etc.

The antisense nucleic acids of the invention comprise a sequence complementary to at least a portion of an RNA transcript of an endokine alpha gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded endokine alpha antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with an endokine alpha RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of the nucleotide sequence shown in FIGS. 1A–1B could be used in an antisense approach to inhibit translation of endogenous endokine alpha mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of endokine alpha mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci. 84:648–652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (see, e.g., Krol et al., BioTechniques 6:958–976 (1988)) or intercalating agents. (see, e.g., Zon, Pharm. Res. 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, a-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids Res. 15:6625–6641 (1987)). The oligonucleotide is a 2'-O-methylribonucleotide (Inoue et al., Nucl. Acids Res. 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., Nucl. Acids Res. 16:3209 (1988), methylphosphonate oligonucleotides can be prepared by use of controlled pore glass polymer supports (Sarin et al., Proc. Natl. Acad. Sci. U.S.A. 85:7448–7451 (1988)), etc.

While antisense nucleotides complementary to the endokine alpha coding region sequence could be used, those complementary to the transcribed untranslated region are most preferred.

Potential antagonists according to the invention also include catalytic RNA, or a ribozyme (see, e.g., PCT International Publication WO 90/11364, published Oct. 4, 1990; Sarver et al, Science 247:1222–1225 (1990). While ribozymes that cleave mRNA at site specific recognition sequences can be used to destroy endokine alpha mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of endokine alpha (FIGS. 1A–1B). Preferably, the ribozyme is engineered so that the cleavage recognition site is located near the 5' end of the endokine alpha mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express endokine alpha in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous endokine alpha messages and inhibit translation. Since ribozymes unlike antisense molecules, are catalytic, a lower intracellular concentration is required for efficiency.

Endogenous gene expression can also be reduced by inactivating or "knocking out" the endokine alpha gene and/or its promoter using targeted homologous recombination. (e.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of endokine alpha (e.g., fragments of the endokine alpha polypeptide shown in FIGS. 1A–1B that include the ligand binding domain from the extracellular region of the full length receptor). Such soluble forms of endokine alpha, which may be naturally occurring or synthetic, antagonize endokine alpha mediated signaling by competing with the cell surface bound forms of the receptor for binding to TNF-family ligands. Antagonists of the present invention also include antibodies specific for TNF-family ligands and endokine alpha-Fc fusion proteins.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-a, lymphotoxin-a (LT-a, also known as TNF-b), LT-b (found in complex heterotrimer LT-a2-b), FasL, CD40L, CD27L, CD30L, 4-1BBL, OX40L and nerve growth factor (NGF).

TNF-α has been shown to protect mice from infection with herpes simplex virus type 1 (HSV-1). Rossol-Voth et al., J. Gen. Virol. 72:143–147 (1991). The mechanism of the protective effect of TNF-α is unknown but appears to involve neither interferons nor NK cell killing. One member of the TNFR family has been shown to mediate HSV-1 entry into cells. Montgomery et al., Eur. Cytokine Newt. 7:159 (1996). Further, antibodies specific for the extracellular domain of this TNFR block HSV-1 entry into cells. Thus, endokine alpha antagonists of the present invention include both endokine alpha amino acid sequences and antibodies capable of preventing TNFR mediated viral entry into cells. Such sequences and antibodies can function by either competing with cell surface localized TNFR for binding to virus or by directly blocking binding of virus to cell surface receptors.

Antibodies according to the present invention may be prepared by any of a variety of standard methods using endokine alpha receptor immunogens of the present invention. Such endokine alpha receptor immunogens include the endokine alpha receptor protein shown in FIGS. 1A–1B (SEQ ID NO:2) (which may or may not include a leader sequence) and polypeptide fragments of the receptor comprising the ligand binding, extracellular, transmembrane, the intracellular domains of the endokine alpha receptors, or any combination thereof.

Polyclonal and monoclonal antibody agonists or antagonists according to the present invention can be raised according to the methods disclosed herein and/or known in the art, such as, for example, those methods described in Tartaglia and Goeddel, J. Biol. Chem. 267(7):4304–4307(1992)); Tartaglia et al., Cell 73:213–216 (1993)), and PCT Application WO 94/09137 (the contents of each of these three applications are herein incorporated by reference in their entireties), and are preferably specific to polypeptides of the invention having the amino acid sequence of SEQ ID NO:2.

As one of skill in the art will appreciate, endokine alpha polypeptides of the present invention and the epitope-bearing fragments thereof described above can be combined with heterologous polypeptide sequences. For example, the polypeptides of the present invention may be fused with the constant domain of immunoglobulins (IgA, IgE, IgG, and IgM) or portions thereof(CH1, CH2, CH3, and any combination thereof, including both entire domains and portions thereof), resulting in chimeric polypeptides. These fusion proteins facilitate purification and show an increased half-life.

The techniques of gene-shuffling, motif-shuffling, exon-shuffling, and/or codon-shuffling (collectively referred to as "DNA shuffling") may be employed to modulate the activities of endokine alpha thereby effectively generating agonists and antagonists of endokine alpha. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of endokine alpha polynucleotides and corresponding polypeptides may be achieved by DNA shuffling. DNA shuffling involves the assembly of two or more DNA segments into a desired endokine alpha molecule by homologous, or site-specific, recombination. In another embodiment, endokine alpha polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of endokine alpha may be recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6): 1185–1190), endokine-alpha (International Publication Nos. WO 98/07880 and WO 98/18921), OPG, OX40, nerve growth factor (NGF), and soluble forms of Fas, CD30, CD27, CD40 and 4-IBB, DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), TR12, and TNF-R1, TRAMP/DR3/APO-3/WSL/LARD, TRAIL-R1/DR4/APO-2, TRAIL-R2/DR5, DcR1/TRAIL-R3/TRID/LIT, DcR2/TRAIL-R4, CAD, TRAIL, TRAMP, and v-FLIP.

In further preferred embodiments, the heterologous molecules are any member of the TNF family.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an endokine alpha protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Endokine Alpha Uses

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," *Symp. Quant. Biol.* 51:597–609 (1986), Cold Spring Harbor; Beutler, B., and Cerami, A., *Annu. Rev. Biochem.* 57:505–518 (1988); Old, L. J., *Sci. Am.* 258:59–75 (1988); Fiers, W., *FEBS Lett.* 285:199–224 (1991)). The TNF-family ligands induce such various cellular responses by binding to TNF-family receptors.

Endokine alpha polynucleotides, polypeptides, agonists or antagonists of the invention may be used in developing treatments for any disorder mediated (directly or indirectly) by defective, or insufficient amounts of endokine alpha. Endokine alpha polypeptides, agonists or antagonists may be administered to a patient (e.g., mammal, preferably human) afflicted with such a disorder. Alternatively, a gene therapy approach may be applied to treat such disorders. Disclosure herein of endokine alpha nucleotide sequences permits the detection of defective endokine alpha genes, and the replacement thereof with normal endokine alpha-encoding genes. Defective genes may be detected in in vitro diagnostic assays, and by comparision of the endokine alpha nucleotide sequence disclosed herein with that of a endokine alpha gene derived from a patient suspected of harboring a defect in this gene.

In another embodiment, the polypeptides of the present invention are used as a research tool for studying the biological effects that result from inhibiting TR11/endokine alpha interactions on different cell types. endokine alpha polypeptides also may be employed in in vitro assays for detecting TR11 or endokine alpha or the interactions thereof.

As indicated above, TNF is noted for its pro-inflammatory actions which result in tissue injury, such as induction of procoagulant activity on vascular endothelial cells (Pober, J. S. et al., *J. Immunol.* 136:1680 (1986)), increased adherence of neutrophils and lymphocytes (Pober, J. S. et al., *J. Immunol.* 138:3319 (1987)), and stimulation of the release of platelet activating factor from macrophages, neutrophils and vascular endothelial cells (Camussi, G. et al., *J. Exp. Med.* 166:1390 (1987)). Recent evidence implicates TNF in the pathogenesis of many infections (Cerami, A. et al., *Immunol. Today* 9:28 (1988)), immune disorders, neoplastic pathology, e.g., in cachexia accompanying some malignancies (Oliff, A. et al., *Cell* 50:555 (1987)), and in autoimmune pathologies and graft-versus host pathology (Piguet, P.-F. et al., *J. Exp. Med.* 166:1280 (1987)). A number of studies have suggested that TNF is an important mediator of the cachexia in cancer, infectious pathology, and in other catabolic states.

Thus, the endokine alpha protein of the present invention can be used for tumor targeting, preferably, after conjugation with radioisotopes or cytostatic drugs (Gruss and Dower, *Blood* 85(12):3378–3404 (1995)). Endokine alpha can be used in patients with melanoma and sarcoma for tumor regression and extension of patient life span through a local injection or used in isolated limb perfusion (Aggarwal and Natarajan, *Eur. Cytokine Netw.* 7(2):92–124 (1996)).

The endokine alpha of the present invention can also have a therapeutic role in specific situations, for example, activity against viral, bacterial, yeast, fungal, and other infections (including toxoplasma gondii, schistosoma mansoni, listeria monocytogens and BCG). These effects of endokine alpha can be indirect and thus preferably, mediated through activation of macrophages, eosinophils, fibroblasts, or neutrophils.

TNF is also thought to play a central role in the pathophysiological consequences of Gram-negative sepsis and endotoxic shock (Michie, H. R. et al., *Br. J. Surg.* 76:670–671 (1989); Debets, J. M. H. et al., *Second Vienna Shock Forum*, p.463–466 (1989); Simpson, S. Q. et al., *Crit. Care Clin.* 5:27–47 (1989)), including fever, malaise, anorexia, and cachexia. Endotoxin is a potent monocyte/macrophage activator which stimulates production and secretion of TNF (Kornbluth, S. K. et al., *J. Immunol.* 137:2585–2591 (1986)) and other cytokines. Elevated levels of circulating TNF have also been found in patients suffering from Gram-negative sepsis (Waage, A. et al., *Lancet* 1:355–357 (1987);

Hammerle, A. F. et al., *Second Vienna Shock Forum* p. 715–718 (1989); Debets, J. M. H. et al., *Crit. Care Med.* 17:489–497 (1989); Calandra, T. et al., *J. Infec. Dis.* 161:982–987 (1990)).

Neutralizing antisera or mAbs to TNF have been shown in mammals other than man to abrogate adverse phaysiological changes and prevent death after lethal challenge in experimental endotoxemia and bacteremia. This effect has been demonstrated, e.g., in rodent lethality assays and in primate pathology model systems (Mathison, J. C. et al., *J. Clin. Invest.* 81:1925–1937 (1988); Beutler, B. et al., *Science* 229:869–871 (1985); Tracey, K. J. et al., *Nature* 330:662–664 (1987); Shimamoto, Y. et al., *Immunol. Lett.* 17:311–318 (1988); Silva, A. T. et al., *J. Infect. Dis.* 162:421–427 (1990); Opal, S. M. et al., *J. Infect. Dis.* 161:1148–1152 (1990); Hinshaw, L. B. et al., *Circ. Shock* 30:279–292 (1990)). To date, experience with anti-TNF mAb therapy in humans has been limited but shows beneficial therapeutic results, e.g., in arthritis and sepsis. See, e.g., Elliott, M. J. et al., *Baillieres Clin. Rheumatol.* 9:633–52 (1995); Feldmann M, et al., *Ann. N. Y. Acad. Sci. USA* 766:272–8 (1995); van der Poll, T. et al., *Shock* 3:1–12 (1995); Wherry et al., *Crit. Care. Med.* 21:S436–40 (1993); Tracey K. J., et al., *Crit. Care Med.* 21:S415–22 (1993).

As endokine alpha is believed to exhibit many of the biological effects of TNF, the present invention is further directed to antibody-based therapies which involve administering an anti-endokine alpha antibody to a mammalian, preferably human, patient for treating one or more of the above-described disorders. Methods for producing anti-endokine alpha polyclonal and monoclonal antibodies are described in detail above. Such antibodies may be provided in pharmaceutically acceptable compositions as known in the art or as described herein.

Polynucleotides and/or polypeptides of the invention, and/or agonists and/or antagonists thereof, are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, gliobalstoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy and lymphomas (e.g., EBVinduced lymphoproliferations and Hodgkin's disease), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, myasthenia gravis, rheumatoid arthritis, systemic lupus erythematosus, immune complex glomerulonephritis, autoimmune diabetes, autoimmmune thrombocytopenic purpura, Grave's disease, Hashimoto's thyroiditis, inflammatory autoimmune diseases, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures), and regulating bone formation and treating osteoporosis.

Polynucleotides and/or polypeptides of the invention and/or agonists and/or antagonists thereof are also useful as an adjuvant to enhance immune responsiveness to specific antigen and/or anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders or in the prevention of transplant rejection. In specific embodiments, polynucleotides and/or polypeptides of the invention are used to treat or prevent chronic inflammatory, allergic or autoimmune conditions, such as those described herein or are otherwise known in the art.

A summary of the ways in which the antibodies of the present invention may be used therapeutically includes binding endokine alpha locally or systemically in the body or by direct cytotoxicity of the antibody, e.g., as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The pharmaceutical compositions of the present invention may be administered by any means that achieve their intended purpose. Amounts and regimens for the administration of antibodies, their fragments or derivatives can be determined readily by those with ordinary skill in the clinical art of treating TNF-related disease.

For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent (see below), the patient and his clinical status, and can vary from about 10 μg/kg body weight to about 5000 mg/kg body weight. The preferred dosages comprise 0.1 to 500 mg/kg body wt.

In addition to the pharmacologically active compounds, the new pharmaceutical compositions may contain suitable pharmaceutically acceptable carriers comprising excipients and auxiliaries which facilitate processing of the active compounds into preparations which can be used pharmaceutically. Preferably, the preparations contain from about 0.01 to 99 percent, preferably from about 20 to 75 percent of active compound(s), together with the excipient.

Similarly, preparations of an endokine alpha antibody or fragment of the present invention for parenteral administration, such as in detectably labeled form for imaging or in a free or conjugated form for therapy, include sterile aqueous or non-aqueous solutions, suspensions, and emulsions. Examples of non-aqueous solvents are propylene glycol, polyethylene glycol, vegetable oil such as olive oil, and injectable organic esters such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, antioxidants, chelating agents, and inert gases and the like. See, generally, *Remington's Pharmaceutical Science*, 16th ed., Mack Publishing Co., Easton, Pa., 1980.

In particular, the antibodies, fragments and derivatives of the present invention are useful for treating a subject having or developing endokine alpha related disorders as described herein. Such treatment comprises parenterally administering single or multiple doses of the antibody, a fragment or derivative, or a conjugate thereof.

The antibodies of this invention may be advantageously utilized in combination with other monoclonal or chimeric antibodies, or with lymphokines or hemopoietic growth factors, etc., which serve to increase the number or activity of effector cells which interact with the antibodies.

Since circulating concentrations of endokine alpha (like TNF) tend to be extremely low, in the range of about 10 pg/ml in non-septic individuals, and reaching about 50 pg/ml in septic patients and above 100 pg/ml in the sepsis syndrome for TNF (Hammerle, A. F. et al., 1989, supra) or may be only be detectable at sites of endokine alpha-related disorders, it is preferred to use high affinity and/or potent in vivo endokine alpha-inhibiting and/or neutralizing antibodies, fragments or regions thereof, for both endokine alpha immunoassays and therapy of endokine related disorders. Such antibodies, fragments, or regions, will preferably have an affinity for human endokine alpha, expressed as Ka, of at least $10^8$ $M^{-1}$, more preferably, at least $10^9$ $M^{-1}$, such as $5 \times 10^8$ $M^{-1}$, $8 \times 10^8$ $M^{-1}$, $2 \times 10^9$ $M^{-1}$, $4 \times 10^9$ $M^{-1}$, $6 \times 10^9$ $M^{-1}$, $8 \times 10^9$ $M^{-1}$.

Preferred for human therapeutic use are high affinity murine and murine/human or human/human chimeric antibodies, and fragments, regions and derivatives having potent in vivo endokine-inhibiting and/or neutralizing activity, according to the present invention, e.g., that block endokine-induced IL-1, IL-6 or TNF secretion, procoagulant activity, expression of cell adhesion molecules such as ELAM-1 and ICAM-1 and mitogenic activity, in vivo, in situ, and in vitro.

Additional preferred embodiments of the invention include, but are not limited to, the use of endokine-α polypeptides and functional agonists in the following applications:

A vaccine adjuvant that enhances immune responsiveness to specific antigen.

An adjuvant to enhance tumor-specific immune responses.

An adjuvant to enhance anti-viral immune responses.

As a stimulator of B cell responsiveness to pathogens.

As a activator of T cells.

As an agent that elevates the immune status of a individual prior to their receipt of immunosuppressive therapies.

As an agent to accelerate recovery of immunocompromised individuals; As an agent to boost immunoresponsiveness among aged populations; As an immune system enhancer following bone marrow transplant.

As an agent to direct an individuals immune system towards development of a humoral response (i.e. TH2) and/or a TH1 cellular response.

As a means to induce tumor proliferation and thus make it more susceptible to anti-neoplastic agents. For example multiple myeloma is a slowly dividing disease and is thus refractory to virtually all anti-neoplastic regimens. If these cells were forced to proliferate more rapidly their susceptibility profile would likely change.

As a B cell and other ligand expressing cell (e.g., endothelial cells) specific binding protein to which specific activators or inhibitors of cell growth may be attached. The result would be to focus the activity of such activators or inhibitors onto normal, diseased, or neoplastic B cell populations.

As a means of detecting B-lineage cells and/or ligand expressing cells (e.g., endothelial cells) by virtue of its specificity. This application may require labeling the protein with biotin or other agents to afford a means of detection.

As a stimulator of B cell production in pathologies such as AIDS, chronic lymphocyte disorder and/or Common Variable Immunodificiency;

As part of a B cell selection device the function of which is to isolate B cells as well as other ligand expressing cells (e.g., endothelial cells) from a heterogenous mixture of cell types. Endokine alpha could be coupled to a solid support to which B cells would then specifically bind. Unbound cells would be washed out and the bound cells subsequently eluted. This technique would allow purging of tumor cells from, for example, bone marrow or peripheral blood prior to transplant.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance endokine alpha mediated responses.

As a means of activating monocytes/macrophages to defend against parasitic diseases that effect monocytes such as Leshmania.

As pretreatment of bone marrow samples prior to transplant. Such treatment would increase B cell representation and thus accelerate recovery.

As a means of regulating secreted cytokines that are elicited by endokine alpha.

Inhibition of unwanted TH1 responses. There is strong evidence to demonstrate that IL-12 is an important cytokine in directing TH1 differentiation. Endokine alpha-induced inhibition of IL-12 production might be helpful in controlling TH1-associated conditions, such as autoimmune diseases, inflammation, acute allograft rejection, fetal reabsorption.

Reduction of inflammatory response. It was shown that induction of IL-10 and MCP-1 ameliorate experimental fecal peritonitis.

Enhanced resistance to pathogens. Products of the oxidative burst, such as $H_2O_2$, are used by monocytes for the killing of phagocytosed pathogens or for the extracellular destruction of cells.

All of the above described applications as they may apply to veterinary medicine.

Antagonists of endokine alpha include binding and/or inhibitory antibodies, antisense nucleic acids, ribozymes or soluble forms of the endokine alpha receptor(s). These would be expected to reverse many of the activities of the ligand described above as well as find clinical or practical application as:

A means of blocking various aspects of immune responses to foreign agents or self. Examples include autoimmune disorders such as lupus, and arthritis, as well as immuno-responsiveness to skin allergies, inflammation, bowel disease, injury and pathogens. Although our current data speaks directly to the potential role of endokine alpha in B cell, T cell and monocyte related pathologies, it remains possible that other cell types may gain expression or responsiveness to endokine alpha. Thus, endokine alpha may, like CD40 and its ligand, be regulated by the status of the immune system and the microenvironment in which the cell is located.

A therapy for preventing the B and/or T cell proliferation and Ig secretion associated with autoimmune diseases such as idiopathic thrombocytopenic purpura, systemic lupus erythramatosus and MS.

An inhibitor of B and or T cell migration in endothelial cells, This activity disrupts tissue architecture or cognate responses and is useful, for example, in disrupting immune responses, and blocking sepsis.

An inhibitor of graft versus host disease or transplant rejection.

A therapy for B cell and/or T cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, and related idiopathic monoclonalgammopathies.

A means of decreasing the involvement of B cells and Ig associated with Chronic Myelogenous Leukemia.

An immunosuppressive agent(s).

An inhibitor of signaling pathways involving ERK1, COX2 and Cyclin D2 which have been associated with endokine alpha induced B cell activation.

The agonists and antagonists may be employed in a composition with a pharmaceutically acceptable carrier, e.g., as described above.

The antagonists may be employed for instance to inhibit endokine alpha chemotaxis and activation of macrophages and their precursors, and of neutrophils, basophils, B lymphocytes and some T-cell subsets, e.g., activated and CD8 cytotoxic T cells and natural killer cells, in certain autoimmune and chronic inflammatory and infective diseases. Examples of auto-immune diseases include multiple sclerosis, and insulin-dependent diabetes.

The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the endokine alpha polypeptides of the present invention. The antagonists may also be employed for treating atherosclerosis, by preventing monocyte infiltration in the artery wall.

The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated.

The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by endokine alpha. The antagonists may also be employed to treat cases of bone marrow failure, for example, aplastic anemia and myelodysplastic syndrome. The antagonists may also be employed to treat asthma and allergy by preventing eosinophil accumulation in the lung. The antagonists may also be employed to treat subepithelial basement membrane fibrosis which is a prominent feature of the asthmatic lung.

Antibodies against endokine alpha may be employed to bind to and endokine alpha activity to treat ARDS, by preventing infiltration of neutrophils into the lung after injury. The antagonists and antagonists of the instant may be employed in a composition with a pharmaceutically acceptable carrier, e.g., as described hereinafter.

Agonists and antagonists of the invention also have uses in stimulating wound and tissue repair, stimulating angiogenesis, stimulating the repair of vascular or lymphatic diseases or disorders. Additionally, agonists and antagonists of the invention may be used to stimulate the regeneration of mucosal surfaces.

The compositions of the invention may be administered alone or in combination with other therapeutic agents. Therapeutic agents that may be administered in combination with the compositions of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergulin, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angiogenic proteins. Angiogenic proteins that may be administered with the compositions of the invention include, but are not limited to,. Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (P1GF), as disclosed in International Publication Number WO 92/06194; Placental Growth Factor-2 (P1GF-2), as disclosed in Hauser et al., *Growth Factors*, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference.

In an additional embodiment, the compositions of the invention are administered in combination with Fibroblast Growth Factors. Fibroblast Growth Factors tha may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Endokine alpha compositions of the invention are also suitably administered by sustained-release systems. Suitable examples of sustained-release compositions include suitable polymeric materials (such as, for example, semi-permeable polymer matrices in the form of shaped articles, e.g., films, or mirocapules), suitable hydrophobic materials (for example, as an emulsion in an acceptable oil) or ion exchange resins, and sparingly soluble derivatives (such as, for example, a sparingly soluble salt).

Sustained-release matrices include polylactides (U.S. Pat. No. 3,773,919, and EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988).

Sustained-release compositions also include liposomally entrapped compositions of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing Endokine alpha polypeptide may be prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544, 545; and EP 102,324. Ordinarily, the liposomes are of the small (about 200–800 Angstroms) unilamellar type in which the lipid content is greater than about 30 mol. percent cholesterol, the selected proportion being adjusted for the Endokine alpha polypeptide therapy.

In another embodiment systained release compositions of the invention include crystal formulations known in the art.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al, N. Engl. J. Med. 321:574 (1989)). Other controlled release systems are discussed in the review by Langer (*Science* 249:1527–1533 (1990)).

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, monophosphoryl lipid immunomodulator, AdjuVax 100a, QS-21, QS-18, CRL1005, aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, *Haemophilus influenzae* B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately, but simultaneously or concurrently; or sequentially. This includes presentations in which the combined agents are administered together as a therapeutic mixture, and also procedures in which the combined agents are administered separately, but simultaneously, e.g., as through separate intravenous lines into the same individual. Administration "in combination" further includes the separate administration of one of the compounds or agents given first, followed by the second.

In another specific embodiment, compositions of the invention are used in combination with PNEUMOVAX-23™ to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus Enterococcus and/or the genus Streptococcus. In another embodiment, compositions of the invention are used in any combination with PNEUMOVAX-23™ to treat, prevent, and/or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/ or condition associated with *Streptococcus pneumoniae*.

The compositions of the invention may be administered alone or in combination with other therapeutic agents, including, but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately, but simultaneously or concurrently; or sequentially. This includes presentations in which the combined agents are administered together as a therapeutic mixture, and also procedures in which the combined agents are administered separately, but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911 and WO 98/18921), APRIL (J. Exp. Med. 188(6):1185–1190), endokine-alpha (International Publication No. WO 98/07880), TR6 (International Publication No. WO 98/30694), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12.

In a preferred embodiment, the compositions of the invention are administered alone or in combination with CD40 ligand (CD40L), a soluble form of CD40L (e.g., AVREND), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEP™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/ NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants-may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In a preferred embodiment, the compositions of the invention are administered in combination with one, two, three, four, five or more of the following drugs: methotrexate, sulfasalazine, sodium aurothiomalate, auranofin, cyclosporine, penicillarnine, azathioprine, an antimalarial drug (e.g., as described herein), cyclophosphamide, chlorambucil, gold, ENBREL™ (Etanercept), anti-TNF antibody, and prednisolone.

In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but are not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination of the components of CHOP.

In an additional embodiment, the compositions of the invention are administered in combination with cytokines. Cytokines that may be administered with the compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In another embodiment, compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the compositions of the invention are administered in combination with IL4 and IL10.

In an additional embodiment, the compositions of the invention are administered with a chemokine. In another embodiment, the compositions of the invention are administered with chemokine beta-8, chemokine beta-1, and/or macrophage inflammatory protein-4. In a preferred embodiment, the compositions of the invention are administered with chemokine beta-8.

In an additional embodiment, the compositions of the invention are administered in combination with an IL-4 antagonist. IL-4 antagonists that may be administered with the compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the compositions of the invention are administered in combination with hematopoietic growth factors. Hematopoietic growth factors that may be administered with the compositions of the invention include, but are not limited to, LEUKINE™ (SARGRAMOSTIM™) and NEUPOGEN™ (FILGRASTIM™).

In an additional embodiment, the compositions of the invention are administered in combination with fibroblast growth factors. Fibroblast growth factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Additionally, the compositions of the invention may be administered alone or in combination with other therapeutic regimens, including, but not limited to, radiation therapy. Such combinatorial therapy may be administered sequentially and/or concomitantly.

Therapeutic Uses

The present invention is further directed to antibody-based therapies which involve administering antibodies of the invention to an animal, preferably a mammal, and most preferably a human, patient for treating one or more of the described disorders. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein such as, for example autoimmune diseases, disorders, or conditions associated with such diseases or disorders (including, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye, autoimmune thyroiditis, hypothyroidism (i.e., Hashimoto's thyroiditis), systemic lupus erhythematosus, Goodpasture's syndrome, Pemphigus, Receptor autoimmunities such as, for example, Graves' Disease, Myasthenia Gravis, and insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders, and immunodeficiencies or conditions associated with such diseases or disorders, including, but not limited to, graft versus host disease and graft rejection.

In a specific embodiment, antibodies of the invention are be used to treat, inhibit, prognose, diagnose or prevent rheumatoid arthritis.

In another specific embodiment, antibodies of the invention are used to treat, inhibit, prognose, diagnose or prevent systemic lupus erythematosis.

The treatment and/or prevention of diseases and disorders associated with aberrant expression and/or activity of a polypeptide of the invention includes, but is not limited to, alleviating symptoms associated with those diseases and disorders. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-8}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

In one embodiment, the invention provides a method of delivering compositions containing the polypeptides of the invention (e.g., compositions containing Endokine alpha polypeptides or anti-Endokine alpha antibodies associated with heterologous polypeptides, heterologous nucleic acids, toxins, or prodrugs) to targeted cells, expressing the membrane-bound form of Endokine alpha on their surface, or alternativley, an Endokine alpha receptor (e.g., TR11) on their surface. Endokine alpha polypeptides or anti-Endokine alpha antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., Endokine alpha or anti-Endokine alpha antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., Endokine alpha polypeptides or anti-Endokine alpha antibodies) in association with toxins or cytotoxic prodrugs.

In a specific embodiment, the invention provides a method for the specific destruction of cells expressing TR11 on their surface (e.g., activated T cells, and/or T cell and/or B cell related leukemias or lymphomas) by administering Endokine alpha polypeptides in association with toxins or cytotoxic prodrugs.

In another specific embodiment, the invention provides a method for the specific destruction of cells expressing the membrane-bound form of Endokine alpha on their surface (e.g., endothelial cells) by administering anti-Endokine alpha antibodies in association with toxins or cytotoxic prodrugs.

By "toxin" is meant compounds that bind and activate endogenous cytotoxic effector systems, radioisotopes, holotoxins, modified toxins, catalytic subunits oftoxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label proteins (including antibodies) of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

The compositions of the invention may be administered to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO 98/24893, WO 96/34096, WO 96/33735, and WO 91/10741). Compositions of the invention include, but are not limited to, endokine-alpha polypeptides and polynucleotides and agonists and antagonists thereof, antibodies, anti-antibodies, etc.

The compositions described herein may be used as a vaccine adjuvant that enhances immune responsiveness to specific antigen. In a specific embodiment, the vaccine adjuvant is an endokine alpha polypeptide described herein. In another specific embodiment, the vaccine adjuvant is an endokine alpha polynucleotide described herein (i.e., the endokine alpha polynucleotide is a genetic vaccine adjuvant). As discussed herein, endokine alpha polynucleotides may be administered using techniques known in the art, including but not limited to, liposomal delivery, recombinant vector delivery, injection of naked DNA, and gene gun delivery.

The compositions described herein may also be an adjuvant used to enhance tumor-specific immune responses.

Anti-viral immune responses that may be enhanced using the compositions of the invention as an adjuvant, include, but are not limited to, virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

Anti-bacterial or anti-fungal immune responses that may be enhanced using the compositions of the invention as an adjuvant, include bacteria or fingus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B streptococcus, Shigella spp., Enterotoxigenic *Escherichia coli*, Enterohemorrhagic *E. coli, Borrelia burgdorferi*, and Plasmodium (malaria).

Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria).

The compositions of the invention may be used as a stimulator of B or T cell responsiveness to pathogens.

The compositions of the invention may be used as an agent that elevates the immune status of an individual prior to their receipt of immunosuppressive therapies; as an agent to induce higher affinity antibodies; as an agent to increase serum immunoglobulin concentrations; as an agent to accelerate recovery of immunocompromised individuals; as an agent to boost immunoresponsiveness among aged populations; and as an immune system enhancer prior to, during, or after bone marrow transplant and/or other transplants (e.g., allogeneic or xenogeneic organ transplantation).

With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

The compositions of the invention may be used as an agent to boost immunoresponsiveness among B cell and/or T cell immunodeficient individuals, such as, for example, an individual who has undergone a partial or complete splenectomy. B cell immunodeficiencies that may be ameliorated or treated by administering the endokine alpha polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency. T cell immunodeficiencies that may be ameliorated or treated by administering the endokine alpha polypeptides or polynucleotides of the invention, or agonists thereof, include, but are not limited to, DiGeorge anomaly, thymic hypoplasia, chronic mucocutaneous candidiasis, natural killer cell deficiency, idiopathic CD4+ T-lymphocytopenia, and immunodeficiency with predominant T-cell defect, graft versus host disease, graft rejections and inflammation associated with an immuno-deficiency.

Additional conditions resulting in an acquired loss of B or T cell function that may be ameliorated or treated by administering the endokine alpha polypeptides or polynucleotides of the invention, or agonists thereof, include, but are not limited to, HIV Infection, AIDS, bone marrow transplant, and B cell chronic lymphocytic leukemia (CLL).

Compositions of the invention may also be used as an agent to boost immunoresponsiveness among individuals having a temporary immune deficiency. Conditions resulting in a temporary immune deficiency that may be ameliorated or treated by administering the endokine alpha polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, and recovery from surgery.

In a preferred embodiment, endokine alpha polynucleotides, polypeptides, and/or agonists and/or antagonists thereof are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidermoid tumor, mucoepithelial dysplasia, mucoid adenocarcinoma, mucoid degeneration, myxoid degeneration, myxomatous degeneration, myxomatosis, mucoid medial degeneration (for example, cystic medial necrosis), mucolipidosis (including, for example, mucolipidosis I, mucolipidosis II, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e., mucopolysaccharidosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, endokine alpha polynucleotides, polypeptides, and/or agonists and/or antagonists thereof are used to treat, prevent, and/or diagnose mucositis, especially as associated with chemotherapy.

Endokine alpha polynucleotides or polypeptides of the invention, or agonists or antagonists thereof, may be used to diagnose, prognose, treat or prevent one or more of the following diseases or disorders, or conditions associated therewith: primary immuodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, Endokine alpha polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19), patients with stable mutliple myeloma who are at high risk for infection (e.g., recurrent infection), autoimmune hemolytic anemia (e.g., warm-type autoimmune hemolytic anemia), thrombocytopenia (e.g., neonatal thrombocytopenia), and immune-mediated neutropenia, transplantation (e.g., cytamegalovirus (CMV)-negative recipients of CMV-positive organs), hypogammaglobulinemia (e.g., hypogammaglobulinemic neonates with risk factor for infection or morbidity), epilepsy (e.g., intractable epilepsy), systemic vasculitic syndromes, myasthenia gravis (e.g., decompensation in myasthenia gravis), dermatomyositis, and polymyositis.

Endokine alpha polynucleotides or polypeptides of the invention and/or agonists and/or antagonists thereof, may be used to treat, prevent, and/or diagnose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of endokine alpha polynucleotides or polypeptides of the invention and/or agonists and/or antagonists thereof that can inhibit an immune response, particularly the proliferation of B cells and/or the production of immunoglobulins, may be an effective therapy in treating and/or preventing autoimmune disorders. Thus, in preferred embodiments, endokine alpha antagonists of the invention (e.g., polypeptide fragments of endokine alpha and anti-endokine alpha antibodies) are used to treat, prevent, and/or diagnose an autoimmune disorder.

Autoimmune disorders and conditions associated with these disorders that may be treated, prevented, and/or diagnosed with the endokine alpha polynucleotides, polypeptides, and/or antagonists of the invention (e.g., anti-endokine alpha antibodies), include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye disease.

Additional autoimmune disorders (that are highly probable) that may be treated, prevented, and/or diagnosed with the compositions of the invention include, but are not limited to, autoimmune thyroiditis, hypothyroidism (i.e., Hashimoto's thyroiditis) (often characterized, e.g., by cell-mediated and humoral thyroid cytotoxicity), systemic lupus erhythematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, Graves' Disease (often characterized, e.g., by TSH receptor antibodies), Myasthenia Gravis (often characterized, e.g., by acetylcholine receptor antibodies), and insulin resistance (often characterized, e.g., by insulin receptor antibodies), autoimmune hemolytic anemia (often characterized, e.g., by phagocytosis of antibody-sensitized RBCs), and autoimmune thrombocytopenic purpura (often characterized, e.g., by phagocytosis of antibody-sensitized platelets.

Additional autoimmune disorders that may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by anti-spermatozoal antibodies), glomerulonephritis (often characterized, e.g.,by glomerularbasement membrane antibodies or immune complexes) such as primary glomerulonephritis and IgA nephropathy, bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), inflammatory myopathies, and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-endokine alpha antibodies.

In a specific preferred embodiment, rheumatoid arthritis is treated, prevented, and/or diagnosed using anti-endokine alpha antibodies and/or other antagonist of the invention.

In a specific preferred embodiment, lupus is treated, prevented, and/or diagnosed using anti-endokine alpha antibodies and/or other antagonist of the invention.

In a specific preferred embodiment, nephritis associated with lupus is treated, prevented, and/or diagnosed using anti-endokine alpha antibodies and/or other antagonist of the invention.

In a specific embodiment, endokine alpha polynucleotides or polypeptides, or antagonists thereof (e.g., anti-endokine alpha antibodies) are used to treat or prevent systemic lupus erythematosus and/or diseases, disorders or conditions associated therewith. Lupus-associated diseases, disorders, or conditions that may be treated or prevented with endokine alpha polynucleotides or polypeptides, or antagonists of the invention, include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleuricy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, the endokine alpha polynucleotides or polypeptides, or antagonists thereof (e.g., anti-endokine alpha antibodies) are used to treat or prevent renal disorders associated with systemic lupus erythematosus. In a most preferred embodiment, Endokine alpha polynucleotides or polypeptides, or antagonists thereof (e.g., anti-endokine alpha antibodies) are used to treat or prevent nephritis associated with systemic lupus erythematosus.

In certain embodiments, soluble endokine alpha polypeptides of the invention, or agonists thereof, are administered, to treat, prevent, prognose and/or diagnose an immunodeficiency (e.g., severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndromecombined immunodeficiency with Igs, purine nucleoside phosphorylase deficiency (PNP), MHC Class II deficiency (Bare Lymphocyte Syndrome) and severe combined immunodeficiency, DiGeorge anomaly, thymic hypoplasia, chronic mucocutaneous candidiasis, natural killer cell deficiency, idiopathic CD4+T-lymphocytopenia, and immunodeficiency with predominant T-cell defect or conditions associated with an immunodeficiency.

In a specific embodiment, endokine alpha polypeptides or polynucleotides of the invention, or agonists thereof, is administered to treat, prevent, prognose and/or diagnose common variable immunodeficiency.

In a specific embodiment, endokine alpha polypeptides or polynucleotides of the invention, or agonists thereof, is administered to treat, prevent, prognose and/or diagnose X-linked agammaglobulinemia.

In another specific embodiment, endokine alpha polypeptides or polynucleotides of the invention, or agonists thereof, is administered to treat, prevent, prognose and/or diagnose severe combined immunodeficiency (SCID).

In another specific embodiment, endokine alpha polypeptides or polynucleotides of the invention, or agonists thereof, is administered to treat, prevent, prognose and/or diagnose Wiskott-Aldrich syndrome.

In another specific embodiment, endokine alpha polypeptides or polynucleotides of the invention, or agonists thereof, is administered to treat, prevent, prognose and/or diagnose X-linked Ig deficiency with hyper IgM.

In another specific embodiment, endokine alpha polypeptides or polynucleotides of the invention, or agonists thereof, is administered to treat, prevent, prognose and/or diagnose DiGeorge anomaly.

In another specific embodiment, the combination of IL-10 and endokine alpha polypeptides or polynucleotides can advantageously be used in the suppression of pathology, associated with T cell responses, in particular, autoimmune diseases, graft-versus-host disease (GVHD) and tissue graft rejection. The invention can be used to suppress cell-mediated reactions such as allograft rejection and GVHD. Moreover, considering the diverse biological activities of IL-10, the concurrent use of IL-10 and endokine alpha polypeptides or polynucleotides may support GVL (graft-versus-leukemia) in allogeneic bone marrow transplants.

In another specific embodiment, the compositions of the invention may be used to prevent the rejection or prolong the survival of allogeneic transplants of skin, bone, neuronal tissue, synovium, heart, kidney, pancreas, bone marrow, small intestine, lung, combined heart-lung, corneal tissue, liver, etc. The transplanted tissue itself is typically human in origin, but may also be from another species such as a rhesus monkey, baboon or pig. As used herein, the term "tissue" includes individual cells, such as blood cells, including progenitors and precursors thereof, and pancreatic cells, as well as solid organs and the like. The term solid organ means a heart, skin, a liver, a lung, a cornea, a kidney, a pancreas, an intestine, endocrine glands, a bladder, skeletal muscles, etc.

In another specific embodiment, the compositions of the invention may be used to treat a large category of diseases, prior to and/or after onset thereof, such diseases including, but not being limited to, autoimmune diseases, including, but not limited to, inflammatory conditions with an etiology including an autoimmune component such as arthritis (for example rheumatoid arthritis, arthritis chronica progrediente and arthritis deformans) and rheumatic diseases.

Autoimmune diseases may be divided into two general types, namely systemic autoimmune diseases (exemplified by arthritis, lupus and scleroderma), and organ specific (exemplified by multiple sclerosis, diabetes and atherosclerosis, in which latter case the vasculature is regarded as a specific organ). Specific autoimmune diseases for which the compositions of the invention may be employed include, but, are not limited to, autoimmune hematological disorders (including, e.g., hemolytic anemia, aplastic anemia, pernicious anemia, pure red cell anemia and idiopathic thrombocytopenia), systemic lupus erythematosus, polychondritis, scleroderma, Wegener granulomatosis, dermatomyositis, chronic active hepatitis, myasthenia gravis, psoriasis, Steven-Johnson syndrome, idiopathic sprue, autoimmune inflammatory bowel disease (including, e.g., ulcerative colitis and Crohn's disease), autoimmune thyroiditis, idiopathic Addison's disease, vitilogo, gluten-sensitive enteropathy, autoimmune neutropenias, pemphigus vulgaris, Goodpasture's disease, bullous pemphigoid, discoid lupus, dense deposit disease, endocrine ophthalmopathy, IBD, asthma, Graves disease, sarcoidosis, multiple sclerosis, cirrhosis including primary biliary cirrhosis, juvenile diabetes (diabetes mellitus type 1), insulin dependent diabetes mellitus (i.e., IDDM, or autoimmune diabetes), uveitis (anterior and posterior), autoimmune gastritis, lymphopenias, polyarteritis nodosa, Sjogren's syndrome, Bechet's disease, Hashimoto's disease, primary myxedema, polymyositis, mixed connective tissue disease, keratoconjunctivitis sicca and vernal keratoconjunctivitis, interstitial lung fibrosis, psoriatic arthritis, glomerulonephritis (with and without nephrotic syndrome, e.g., including idiopathic nephrotic syndrome or minimal change nephropathy), juvenile dermatomyositis, hepatitis including chronic active hepatitis, organ rejection, and other afflictions. Other diseases and conditions include, but are not limited to, autoimmune thyroiditis, autoimmune hemolytic anemia, and contact sensitivity disease, which may, for example, be caused by plant matter, such as poison ivy. Other diseases and conditions include, but are not limited to, suppressing chronic and acute monophasic EAE, HIV-related conditions, AIDS, SCIDS, adjuvant arthritis, a lymphatic malignancy or immune disorder, and neurodegenerative diseases such as amyotrophic lateral sclerosis, Alzheimer's disease, Parkinson's disease and primary lateral sclerosis. Further, the inventive compositions can be used to promote wound healing and to treat infectious diseases.

The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis. Other conditions include immune system-related miscarriage and inflammatory disorders. The discoveries of the present invention may also be applied to treat autoimmune diseases which manifest as infertility, including endometriosis.

Further, it is becoming increasingly apparent that many vascular disorders, including atherosclerotic forms of such disorders, have an autoimmune component, and a number of patients with vascular disease have circulating auto antibodies.

In general, the compositions of the invention are useful in immunomodulation, especially immunosuppression, and in the treatment of leukemias characterized by overproliferation of T-lymphocytes, including virally-induced leukemias, e.g., HTLV-1-induced leukemia. An improvement or amelioration in immune ftmction can be assessed by observation ofpartial or total restoration of the ability to mount an immune response. In the case of autoimmune disease, an improvement or amelioration can best be assessed by a significant reduction or disappearance of a clinical symptom associated with inflammation caused by the autoimmune disease, for example, joint pain or swelling or stiffness in rheumatoid arthritis; number of major attacks in chronic-relapsing multiple sclerosis; stabilization or improvement of motor function in chronic progressive multiple sclerosis; intestinal inflammation in the case of Chron's disease; and serological measurements (such as antibody to double-stranded DNA, complement components and circulating immune complexes), and number and severity of skin flare-ups or myalgras, arthralgia, leukopenia, or thrombocytopenia for systemic lupus erythematosus. The symptoms which can be used to monitor efficacy of a regimen in autoimmune disease are generally well-known in the art.

The compositions of the invention can be applied to induce T cell tolerance to a variety of antigens. For example, T cell tolerance can be induced to a soluble antigen (e.g., a soluble protein). T cells can be tolerized to antigens involved in autoimmune diseases or disorders associated with abnormal immune responses. For example, in one embodiment, the antigen is an autoantigen. In another embodiment, the antigen is an allergan. Alternatively, T cells can be tolerized to antigens expressed on foreign cells. Accordingly, in yet other embodiments, the antigen is an alloantigen or xenoantigen. Induction of T cell tolerance to alloantigens and xenoantigens is of particular use in transplantation, for example to inhibit rejection by a transplant recipient of a donor graft, e.g., a tissue or organ graft or bone marrow transplant. Additionally, tolerization of donor T cells within a bone marrow graft is useful for inhibiting graft versus host disease.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217(1993); TIBTECH 11(5):155–215 (May 1993)). Methods commonly known in the art of recombinant DNA technology which can be used are described in Ausubel et al., eds., Current Protocols in Molecular Biology, John Wiley & Sons, N.Y. (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, Proc. Natl. Acad. Sci. USA 86:8932–8935 (1989); Zijlstra et al., Nature 342:435–438 (1989)). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where they are expressed to produce the encoded product. This can be accomplished by any of numerous methods known in the art, e.g., by constructing them as part of an appropriate nucleic acid expression vector and administering them so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/ 20316 dated Nov. 26, 1992 (Findeis et al.); WO93/14188 dated Jul. 22, 1993 (Clarke et al.); and WO 93/20221 dated Oct. 14, 1993 (Young)). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contain nucleic acid sequences encoding an antibody of the invention are used. For example, a retroviral vector can be used (see Miller et al., *Meth. Enzymol.* 217:581–599 (1993)). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., *Biotherapy* 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al, *J. Clin. Invest.* 93:644–651 (1994); Kiem et al., *Blood* 83:1467–1473 (1994); Salmons and Gunzberg, *Human Gene Therapy* 4:129–141 (1993); and Grossman and Wilson, *Curr. Opin. in Genetics and Devel.* 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499–503 (1993) present a review of adenovirus-based gene therapy. Bout et al., *Human Gene Therapy* 5:3–10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431–434 (1991); Rosenfeld et al., *Cell* 68:143–155 (1992); Mastrangeli et al., *J. Clin. Invest.* 91:225–234 (1993); PCT Publication WO94/12649; and Wang, et al., *Gene Therapy* 2:775–783 (1995). In a preferred embodiment, adenovirus vectors are used.

Adeno-associated virus (AAV) has also been proposed for use in gene therapy (Walsh et al., *Proc. Soc. Exp. Biol. Med.* 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method oftransfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.* 217:599–618 (1993); Cohen et al., *Meth. Enzymol.* 217:618–644 (1993); Cline, *Pharmac. Ther.* 29:69–92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cells used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, *Cell* 71:973–985 (1992); Rheinwald, *Meth. Cell Bio.* 21A:229 (1980); and Pittelkow and Scott, *Mayo Clinic Proc.* 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, *J. Biol. Chem.* 262:4429–4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in avesicle, in particulara liposome (see Langer, *Science* 249:1527–1533 (1990); Treat et al., in *Liposomes in the Therapy of Infectious Disease and Cancer*, Lopez-Berestein and Fidler, eds., Liss, New York, pp. 353–365 (1989); Lopez-Berestein, ibid., pp. 317–327).

In yet another embodiment, the compound or composition can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise, eds., CRC Pres., Boca Raton, Fla. (1974); *Controlled Drug Bioavailability, Drug Product Design and Performance*, Smolen and Ball, eds., Wiley, New York (1984); Ranger and Peppas, J., *Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115–138 (1984)).

Other controlled release systems are discussed in the review by Langer (*Science* 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad Sci. USA* 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M., et al., *J. Cell. Biol.* 101:976–985 (1985); Jalkanen, M., et al., *J. Cell. Biol.* 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. in vivo tumor imaging is described in S. W. Burchiel et al., "Immunopharmacokinetics of Radiolabeled Antibodies and Their Fragments." (Chapter 13 in *Tumor Imaging. The Radiochemical Detection of Cancer*, S. W. Burchiel and B. A. Rhodes, eds., Masson Publishing Inc. (1982)).

Depending on several variables, including the type of label used and the mode of administration, the time interval following the administration for permitting the labeled molecule to preferentially concentrate atsites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Having generally described the invention, the same will be more readily understood by reference to the following examples, which are provided by way of illustration and are not intended as limiting.

EXAMPLES

Example 1

Expression and Purification of Endokine Alpha in *E. coli*

The DNA sequence encoding the endokine alpha protein in the deposited cDNA clone is amplified using PCR oligonucleotide primers specific to the amino terminal sequences of the endokine alpha protein. Additional nucleotides containing restriction sites to facilitate cloning are added to the 5' and 3' sequences, respectively.

The 5' oligonucleotide primer has the sequence GCG <u>CCA TGG</u> CTA AGT TTG GAC CAT (SEQ ID NO:5) containing the underlined Nco I restriction site.

The 3' primer has the sequence GCG <u>AAG CTT</u> TCA AGT CTC TAG GAG ATG (SEQ ID NO:6) containing the underlined HindIII restriction site.

The restriction sites are convenient to restriction enzyme sites in the bacterial expression vector pQE60, which is used for bacterial expression in M15/rep4 host cells in these examples. (Qiagen, Inc., Chatsworth, Calif., 91311). pQE60 encodes ampicillin antibiotic resistance ("Amp<sup>r</sup>") and contains a bacterial origin of replication ("ori"), an IPTG inducible promoter, a ribosome binding site ("RBS"), a 6-His tag and restriction enzyme sites.

The amplified endokine alpha protein DNA and the vector pQE60 both are digested with NcoI and HindIII and the digested DNAs are then ligated together. Insertion of the endokine alpha protein DNA into the restricted pQE60 vector places the endokine alpha protein coding region downstream of and operably linked to the vector's IPTG-inducible promoter and in-frame with an initiating ATG appropriately positioned for translation of endokine alpha protein.

The ligation mixture is transformed into competent *E. coli* cells using standard procedures. Such procedures are described in Sambrook et al., *Molecular Cloning: A Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan<sup>r</sup>"), is used in carrying out the illustrative example described here. This strain, which is only one of many that are suitable for expressing endokine alpha protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 NM ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2x phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS.

Example 2

Cloning and Expression of Endokine Alpha in a Baculovirus Expression System

The cDNA sequence encoding the endokine alpha protein in the deposited clone is amplified using PCR oligonucleotide primers corresponding to 5' and 3' regions of the gene.

The 5' primer has the sequence GC GGA TCC <u>GGA TCC</u>CGA GAC TGC TAA GGA GCC (SEQ ID NO:7) containing the underlined BamHI restriction enzyme site and containing nucleotides encoding a portion of the endokine alpha protein in FIGS. 1A–1B.

The 3' primer has the sequence GC <u>GGA TCC</u>CTA GGA GAT GAA TTG GGG ATT TG (SEQ ID NO:8) containing the underlined BamHI restriction site and containing a sequence complementary to that encoding a portion of the endokine alpha protein in FIG. 1.

The amplified fragment is isolated from a 1% agarose gel using a commercially available kit ("Geneclean," BIO 101 Inc., La Jolla, Calif.). The fragment then is digested with BamHI and again is purified on a 1% agarose gel. This fragment is designated herein F2.

The vector pA2-GP is used to express the endokine alpha protein in the baculovirus expression system, using standard methods, as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus, the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170:31–39, among others.

The plasmid is digested with the restriction enzyme BamHI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human endokine alpha gene by digesting DNA from individual colonies using BamHI and then analyzing the digestion product by gel electrophoresis. The sequence of the cloned fragment is confirmed by DNA sequencing.

5 μg of the plasmid is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 μg of BaculoGold™ virus DNA and 5 μg of the plasmid are mixed in a sterile well of a microtiter plate containing 50 μl of serum-free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 $\mu$l of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted endokine alpha is identified by DNA analysis including restriction mapping and sequencing of this plasmid.

Sf9 cells are grown in Grace's medium supplemented with 10% heat-inactivated FBS. The cells are infected with the recombinant baculovirus at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 $\mu$Ci of $^{35}$S-methionine and 5 $\mu$Ci $^{35}$S-cysteine (available from Amersham) are added. The cells are further incubated for 16 hours and then they are harvested by centrifugation, lysed and the labeled proteins are visualized by SDS-PAGE and autoradiography.

Example 3

Cloning and Expression in CHO Cells

The vector pC4 is used for the expression of endokine alpha protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing th& cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., *J Biol. Chem*. 253:1357–1370 (1978), Hamlin, J. L. and Ma, C., *Biochem. et Biophys. Acta*, 1097:107–143 (1990), Page, M. J. and Sydenham, M. A., *Biotechnology* 9:64–68) (1991). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol*. 5:438–447 (1985)) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the endokine alpha in a regulated way in mammalian cells (Gossen, M., & Bujard, H., *Proc. Natl. Acad. Sci. USA* 89: 5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718I and then dephosphorylated using calf intestinal phosphatase by procedures known in the art. The vector is then isolated from a 1% agarose gel.

The DNA sequence encoding the complete endokine alpha protein including its leader sequence is amplified using PCR oligonucleotide primers corresponding to the 5' and 3' sequences of the gene. The 5' primer has the sequence 5' GCG GGA TCC <u>GGA TCC</u>GCC ATC ATG CCT TTA AGC CAT TC 3' (SEQ ID NO:9) containing the underlined BamHI restriction enzyme site followed by an efficient signal for initiation of translation in eukaryotes, as described by Kozak, M., *J. Mol. Biol*. 196:947–950 (1987), and 17 bases of the coding sequence of endokine alpha shown in FIGS. 1A–1B (SEQ ID NO:1). The 3' primer has the sequence 5' GC GGA TCC <u>GGA TCC</u>CTA GGA GAT GAA TTG GGG ATT TG 3' (SEQ ID NO:10) containing the underlined Asp718I restriction site followed by nucleotides complementary to the non-translated region of the endokine alpha gene shown in FIGS. 1A–1B (SEQ ID NO:1).

The amplified fragment is digested with the endonucleases BamHI and Asp718I and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 $\mu$g of the expression plasmid pC4 is cotransfected with 0.5 $\mu$g of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 µM, 20 µM). The same procedure is repeated until clones are obtained which grow at a concentration of 100–200 µM. Expression of the desired gene product is analyzed, for instance, by SDS-PAGE and Western blot or by reverse phase HPLC analysis.

Example 4

Tissue Distribution of Endokine Alpha Expression

Northern blot analysis was carried out to examine the levels of expression of the gene encoding the endokine alpha protein in human tissues, using methods described by, among others, Sambrook et al., supra. A cDNA probe containing the entire nucleotide sequence of the endokine alpha protein of the present invention (SEQ ID NO:1) was labeled with $^{32}$P using the rediprime™ DNA labeling system (Amersham Life Science), according to manufacturer's instructions. After labelling, the probe was purified using a CHROMA SPIN-100™ column (Clontech Laboratories, Inc.), according to manufacturer's protocol number PT1200-1. The purified labelled probe was then used to examine various human tissues for the expression of the gene encoding the endokine alpha protein.

Multiple Tissue Northern (MTN) blots containing various human tissues (H) or human immune system tissues (IM) were obtained from Clontech and were examined with labelled probe using ExpressHyb™ Hybridization Solution (Clontech) according to manufacturer's protocol number PT1190-1. Following hybridization and washing, the blots were mounted and exposed to film at −70° C. overnight, and films developed according to standard procedures.

Expression of the gene encoding an endokine alpha protein of the present invention was detected in human brain striatum and pancreas tissue.

Example 5

Identification of A Novel Activation-Inducible Protein of the TNF Receptor Superfamily and Its Ligand Background Members of the TNFR superfamily share similar multiple cysteine-rich pseudorepeats of the extracellular domain, each containing 30–45 amino acids with six cysteines (Smith, C. A., et al, *Cell* 76:959–962 (1994)). Except for the death domain-containing family which includes TNFR1 (Schall, T. J., et al, *Cell* 61:361–370 (1990)), Fas (Trauth, B. C., et al, *Science* 245:301–305 (1989), Yonehara, S., et al, *J. Exp. Med.* 169:1747–1756 (1989), and Oehm, A., et al, *J. Biol. Chem.* 267:10709–10715 (1992)), DR3 (Chinnaiyan, A. M., et al, *Science* 274:990–992 (1996), Kitson, J., et al, *Nature* 384:372–375 (1996), Bodmer, J.-L., et al, *Immunity* 6:79–88 (1997), and Screaton, G. R., et al, *Proc. Natl. Acad. Sci. USA* 94:4615–4619 (1997)), DR4 (Wiley, S. R., et al, *Immunity* 3:673–682 (1995), Pitti, R. M., et al, *J. Biol. Chem.* 271:12687–2690 (1996), and Pan, G., et al, *Science* 276:111–113 (1997)), DR5 (Walczak, H., et al, *EMBO J.* 16:5386–5397 (1997), MacFarlane, M., et al, *J. Biol. Chem.* 272:25417–25420 (1997), Schneider, P., et al, *Immunity* 7:831–836 (1997), Chaudhary, P. M., et al, *Immunity* 7:821–830 (1997), and Sheridan, J. P., et al, *Science* 277:818–821(1997)), and decoy TRAIL receptors (Marsters, S. A., et al, *Cur. Biol.* 7:1003–1006 (1997), Pan, G., et al, *Science* 277:815–815 (1997), Degli-Esposti, M. A., et al, *J. Exp. Med.* 186:1165–1170 (1997), and Degli-Esposti, M. A., et al, *Immunity* 7:813–820 (1997)), no remarkable similarity is found within the intracellular domain of these molecules. However, there is a striking homology in the cytoplasmic domains of murine and human 4-1BB, CD27, and murine GITR within TNFR superfamily members (Kwon, B. S., et al, *Proc. Natl. Acad. Sci. USA* 86:1963–1967 (1989), Camerimi, D., et al, *J. Immunol.* 147:3165–3169 (1991), and Nocentini, G., et al, *Proc. Natl. Acad. Sci. USA* 94:6216–6221 (1997)). Acidic amino acids are especially highly conserved in the cytoplasmic domain of this subfamily. Like other TNFR superfamily members (Smith, C. A., et al, *Cell* 76:959–962 (1994)), this subfamily is implicated in diverse biological functions. First of all, 4-1BB and CD27 molecules provide strong costimulatory signals for T cell proliferation when ligated with their respective ligands or with agonistic antibodies (Smith, C. A., et al, *Cell* 76:959–962 (1994), and Pollok, K. E., et al, *J. Immunol.* 150:771–781 (1993)). In addition to functioning as an accessory molecule, CD27 induces apoptosis, which is mediated by a death domain-containing molecule called Siva (Prasad, K. V. S., et al, *Proc. Natl. Acad. Sci. USA* 94:6346–6351 (1997)). Recently identified murine GITR is shown to inhibit TCR-induced apoptosis (Nocentini, G., et al, *Proc. Natl. Acad. Sci. USA* 94:6216–6221 (1997)).

Although the immunological functions of subfamily members have been relatively well defined, insights into their signal transduction pathway have only recently been revealed (Arch, R. H., et al, *Mol. Cell. Biol.* 18:558–565 (1998), Jang, I. K., et al, *Biochem. Biophys. Res. Com.* 242:613–620 (1998), Saoulli, K., et al, *J. Exp. Med.* 187:1849–1862 (1998), and Akiba, H., et al, *J. Biol. Chem.* 273:13353–13358 (1998)). Two groups (Arch, R. H., et al, *Mol. Cell. Biol.* 18:558–565 (1998), and Jang, I. K., et al, *Biochem. Biophys. Res. Com.* 242:613–620 (1998)) have provided data indicating that association of 4-1BB with TRAF2 molecules initiates a signal cascade leading to activation of NF-κB. In the CD27 signaling pathway, both TRAF2 and TRAF5 mediate NF-κB and SAPK/JNK (stress-activated protein kinase/c-Jun N-terminal kinase) activation and NIK (NF-κB-inducing kinase) is a common downstream kinase of TRAF2 and TRAF5 (Akiba, H., et al, *J. Biol. Chem.* 273:13353–13358 (1998)).

Because the number of TNFR members is rapidly expanding, it was expected that even more numbers of the superfamily would exist. By a PCR-based strategy with murine GITR sequence and searching an EST (expressed sequence tag) database, a new member of the TNFR was discovered and named TR11. The following provides a characterization of the receptor TR11 and its ligand, endokine alpha.

Experimental Procedures cDNA cloning. A database containing more than two million ESTs obtained from over 750 different cDNA libraries was generated by Human Genome Sciences, Inc., using high throughput automated DNA sequence analysis of randomly selected human cDNA clones. A specific homology and motif search using the known amino acid sequence and motif of TNFR members against this database revealed several ESTs with a translated sequence 35–55% homologous to that of the TNFR family. Several clones were identified from cDNA libraries of PHA-activated T cells, T helper cells, leukocytes, a healing abdomen wound, primary dendritic cells and adipose tissue. A full-length TR-11 cDNA clone encoding an intact N-terminal signal peptide was obtained from a human activated T-cell library and selected for further investigation (see, U.S. patent application Ser. No. 09/176,200 filed Oct. 21, 1998). The complete cDNA sequence of both strands of this clone was determined, and its homology to TNFR members was confirmed. The same gene was also identified by a PCR-based strategy with murine GITR sequence. Similarly, endokine-α (TNF ligand 6) was identified through a systematic comparison of sequence homology with TNF ligand family members. Partial endokine-α sequences which were 25% homologous to that of TNF ligand family members were identified from endothelial, HUVEC (human umbilical vein endothelial cell), brain, and fetal liver cDNA libraries. A full-length cDNA clone was obtained from a human brain cDNA library.

Expression vectors. Full-length and HA (hemaglutinin A epitope)-tagged TR-11 encoding the putative entire TR-11 protein (amino acids 26–234) were amplified by PCR using sense (5'-CTAGCTAGCTAGVVVAGCGCCCC ACCGGGGGTCCC-3', and 5'-CTAGCTAGCTAGCTATCCATAT GATGTTCCAGAT-TATGCTCAGCGCCCCACCGGGGG TCCC-3', respectively) and anti-sense (5'-AAGGAAAAAAGCGGGCCGCTCA CACCCACAGGTCTCCCAG-3') primers, cut with Nhe I/Not I, and fused in frame downstream of a CD5 leader sequence (Jang, I. K., et al, Biochem. Biophys. Res. Com. 242:613–620(1998)) into the pcDNA3.1 (pcDNA3.1/CD5L-TR-11) and pcDNA3 (pcDNA3/CD5L-TR-11), respectively. Full-length endokine-α was amplified by PCR (sense, 5'-AGACCCAAGCTTTTGAAAATGAT ATGAGACGC-3'; anti-sense, 5'-AGACGGGATCCTCCTCCTATAGTAA GAAGGC-3'), cut with Hind III/BamH I, and inserted into pcDNA3.1 (pcDNA3.1/endokine-α) and pCEP4 (Invitrogen, Carlsbad, Calif.; pCEP4/endokine-α). pRK5-based expression vectors encoding Flag-tagged full-length TRAF1, TRAF2, TRAF3, TRAF5, TRAF6, NIK, dominant negative TRAF2 (dnTRAF2), or dnNIK have been described (Jang, I. K., et al, Biochem. Biophys. Res. Com. 242:613–620 (1998), Rothe, M., et al, Science 269:1421–1427 (1995), Hu, H. M., et al, J. Biol. Chem. 269:30069–30072 (1994), Nakano, H., et al, J. Biol. Chem. 271:14661–14664 (1996), Takeuchi, M., et al, J. Biol. Chem. 271:19935–19942 (1996), Cao, Z., et al, Nature 383:443–446 (1996), and Song, H. Y., et al, Proc. Natl. Acad. Sci. USA 94:9792–9796 (1997)). The NF-κB-dependent E-selectin-luciferase reporter gene (pELAM-Luc) and pRSV-β-galactosidase (pRSV-β-gal) plasmids were also described elsewhere (Rothe, M., et al, Science 269:1421–1427 (1995), and Schindler, U., et al, Mol. Cell. Biol. 14:5820–9796 (1994)).

Northern blot and RT (reverse transcriptase)-PCR analysis. For Northern blot analysis, cDNA probes were labeled with $^{32}$P using the Rediprime DNA labeling system (Amersham Life Science, Arlington Height, Ill.), according to the manufacturer's instructions. Unincorporated nucleotide was removed from the labeled probe using CHROMA SPIN-100 (Clonetech, Palo Alto, Calif.). Two human multiple tissue poly (A) RNA blots containing approximately 2 μg of poly (A) RNA per lane from various human tissues were purchased from Clontech. In addition, two cell line blots containing 20 mg total RNA from different cell lines were used. Northern blotting was performed with the Expressed Hybridization Solution (Clonetech) according to the manufacturer's manual. For RT-PCR analysis, total RNA was isolated from human PBMC after stimulation with dexamethasone, PMA/ionomycin, or anti-CD3/CD28 mAbs, and from unstimulated or LPS-stimulated HUVEC cells. RT-PCR was performed under standard conditions.

Interaction of TR-11 with TRAFs. pcDNA3/CD5L-TR-11-HA plasmid (5 μg/10 cm-plate) was co-transfected into HEK293 EBNA cells (2×10$^6$ cells/plate) by the standard calcium phosphate precipitation method with pRK/TRAF1, 2, 3, 5, or 6-Flag vector (5 μg/plate). Twenty four-hours after transfection, cells were lysed with 1 ml of lysis buffer (50 mM HEPES [pH7.4], 250 mM NaCl, 0.1% Nonidet P-40, 5 mM EDTA, 10% glycerol, and protease inhibitors). For immunoprecipitation, lysates were incubated with anti-Flag M2 (Eastman Kodak, Rochester, N.Y.) or control murine IgG1 mAb at 4° C. for 1 h, followed by incubation with 20 μl of a 1:1 slurry of protein G-Sepharose (PharMingen, San Diego, Calif.) for another hour. Precipitates were thoroughly washed with lysis buffer, then fractionated on a 10% SDS-polyacrylamide gel before transfer to PVDF membrane (Millipore, Bedfore, Mass.). Western blot analysis was performed with anti-HA mAb coupled with horseradish peroxidase (Boehringer Mannheim, Indianapolis, Ind.) and visualized using the enhanced chemiluminescence Western blotting detection system (Amersham).

Analysis of NF-κB by reporter assay. Approximately 0.5×10$^6$ HEK293 EBNA cells/well were seeded on 6-well plates. After 24 h, cells were transfected by the standard calcium phosphate precipitation method using various combinations of pcDNA3.1/CD5L-TR-11 plus pRK5 plasmids encoding TRAFs, dnTRAF2, NIK, or dnNIK. The total amount of plasmid was adjusted to 2.0 μg by adding empty vector. Twenty-four hours after transfection, cells were lysed in 200 μl reporter lysis buffer (Promega, Madison, Wis.). Luciferase activity was measured using 20 μl cell extract. 5 μl cell extract was used to assay β-galactosidase activity as an internal control, and luminescence values were normalized by individual β-galactosidase activity.

Recombinant protein production and purification. TR-11-Fc fusion protein was used for ligand screening and cell-binding experiments. A fragment encoding the predicted extracellular domain of TR-11 (amino acids 26–139) was amplified using a sense primer flanked by an Nhe I site (5'-AGACCCAAGCTTGTGGGCTCTTGAAACCCGGCA TG-3') and an antisense primer flanked by a Bgl II site (5'-GAAAGATCTGGGCTCTGCCGG CGGGGACCCTGGGAC-3'). The amplified fragment was cut with Nhe I/Bgl II and cloned into mammalian vector pCEP4, in frame with CD5L at the 5' end and with the Fc portion of human IgG1 at the 3' end (pCEP4/CD5L-TR-11-Fc). pCEP4/CD5L-TR-11-Fc was transfected into HEK293 EBNA cells. TR-11-Fc fusion protein was purified from pCEP4/CD5L-TR-11-Fc-transfected HEK293 EBNA cell supernatants using protein G column. To generate a Flag-tagged soluble form of endokine-α protein (amino acids 39–169), the flag-tagged endokine-α expression vector (pCEP4/CD5L-endokine-α-Flag) was constructed by PCR amplification of endokine-α coding sequences using sense (5'-CTAGCTAGCCCAGCGCCCCGACTACAAG-GACGACGATGACAAGGA GACTGCTAAGGAGCCC-3') and antisense (5'-CCGCTCGAGCTATAG TAAGAAGGCTCC-3') primers, digesting the product with Nhe I/Xho I and cloning into pCEP4, in frame with the CD5L sequence. The construct was expressed in HEK293 EBNA cells. Transfected cell supernatants containing secreted endokine-α-Flag were harvested and used for binding assays. For some experiments, endokine-α-Flag protein was purified from harvested supernatants, using anti-Flag gel (Sigma, St. Louis. Mo.) according to the manufacturer's instructions.

Binding assay. Protein binding assays were done essentially as described (Pan, G., et al, *Science* 276:111–113 (1997)). For cell-binding assays, HEK293 EBNA cells were transfected using pcDNA3.1/CD5L-TR-11 or pcDNA3.1, as described above. Forty-eight hours after transfection, cells were harvested and incubated consecutively with endokine-α-Flag-containing supernatant, anti-Flag antibody, and FITC-conjugated anti-mouse IgG antibody (Southern Biotechnology, Birmingham, Ala.). Flow cytometry analysis was performed using the Becton Dickinson FACScan (San Jose, Calif.). Jurkat T cells were stably transfected by electroporation using linearized pcDNA3.1/CD5L-TR-11, and selected in the presence of Zeocin (Invitrogen). A binding assay for this cell line was performed as described above. To test the ability of TR-11-Fc fusion protein to bind membrane-bound endokine-α, pCEP4/endokine-α was stably transfected into HEK293 EBNA cells. After selection in the presence of hygromycin, endokine-α-expressing cells were harvested and incubated with TR-11-Fc protein, followed by FITC-conjugated anti-human IgG1 antibody (Southern Biotechnology). The Becton Dickinson FACScan was used for flow cytometry analysis.

Results and Discussion

TR-11 was identified by searching an EST database and by a PCR-based strategy with murine GITR sequence. A full-length cDNA of a clone from a human activated T-cell cDNA library, which is tentatively named TR-11 (for activation-inducible TNFR family member), encodes a 234 amino acid type I transmembrane protein with a calculated MW of 25 kDa. The receptor has a signal peptide (the first 25 amino acids) and a single transmembrane region (amino acids 140–158). When compared with the extracellular domain of other TNFR family members, TR-11 displays three cysteine-rich pseudorepeats corresponding to the second, third, and fourth TNFR motif, respectively. The first cysteine pseudorepeat contains eight cysteine residues and lacks C4. Therefore, it is unlikely that the canonical pattern of C1–C2, C3–C5, and C4–C6 disulfide bridges exist in this motif. The second pseudorepeat shows some features of the third TNFR motif, but it is atypical in that C5 is not present even though it contains 7 cysteine residues. The third pseudorepeat shows extensive homologies with the fourth pseudorepeat of 4-1BB. The cytoplasmic domain contains acidic amino acids which are highly conserved in the cytoplasmic domains of 4-1BB, CD27, and GITR. Overall, TR-11 exhibits a high homology (55% identity) to murine GITR, but there is a mismatch in the first cysteine-rich pseudorepeat between GITR and TR-11, because the first pseudorepeat of GITR corresponds to the first TNFR cysteine-rich motif (Nocentini, G., et al, *Proc. Natl. Acad. Sci. USA* 94:6216–6221 (1997)).

The expression of TR-11 mRNA was investigated in multiple human tissues by Northern blot hybridization. 1.25-kb mRNA was detected in lymph node, PBL, and, weakly, in spleen. We also tested a variety of tumor cell lines for expression of TR-11 mRNA. 1.25-kb message was detected only in the colorectal adenocarcinoma cell line, SW480, among the cell lines tested. The expression of virtually all members of the TNFR superfamily is enhanced by antigen stimulation/lymphocyte activation (Smith, C. A., et al, *Cell* 76:959–962 (1994)). Consistent with this idea, TR-11 expression was upregulated in PBMC after stimulation. No TR-11 message was detectable in unstimulated PBMC when we used a sensitive RT-PCR method. TR-11 expression was clearly induced within 24 h by typical PBMC stimulation such as treatment with PMA plus ionomycin or soluble anti-CD3 plus anti-CD28 mAbs. FACS analysis for TR-11 expression, however, showed that a small population of activated PBMC expressed TR-11 on the cell surface at 48 h after stimulation, suggesting that a prolonged period of stimulation is required for maximum expression of TR-11 (BK, unpublished data). Expression of TR-11 was not induced by treatment with dexamethasone. This property was different from that of GITR (Nocentini, G., et al, *Proc. Natl. Acad. Sci. USA* 94:6216–6221 (1997)).

Recently it has been shown that 4-1BB molecules associate with TRAF1, TRAF2, and TRAF3 (Arch, R. H., et al, *Mol. Cell. Biol.* 18:558–565 (1998), Jang, I. K., et al, *Biochem. Biophys. Res. Com.* 242:613–620 (1998), and Saoulli, K., et al, *J. Exp. Med.* 187:1849–1862 (1998)). Because TR-11's cytoplasmic domain is similar to that of 4-1BB, its ability to co-precipitate five of the six known TRAFs that were overexpressed in HEK293 EBNA cells was tested. An interaction of TR-11 with TRAF1, TRAF2, and TRAF3 was observed but not with TRAF5 and TRAF6. The association of TR-11 with TRAF2 suggested that, like other members of the TNFR superfamily (Arch, R. H., et al, *Mol. Cell. Biol.* 18:558–565 (1998), Jang, I. K., et al, *Biochem. Biophys. Res. Com.* 242:613–620 (1998), Akiba, H., et al, *J. Biol. Chem.* 273:13353–13358 (1998), Rothe, M., et al, *Science* 269:1421–1427 (1995), Cheng, G., et al, *Science* 267:1494–1498 (1995), Duckett, C. S., et al, *Mol Cell. Biol.* 17:1535–1542 (1997), and VanArsdale, T. L., et al, *Proc. Natl. Acad. Sci. USA* 94:2460–2465 (1996)), TR-11 might mediate NF-κB activation through TRAF2. To test this possibility, an NF-κB reporter system in HEK293 EBNA cells was used (Rothe, M., et al, *Science* 269:1421–1427 (1995)). Co-transfection with the TR-11 expression vector typically induced greater than 3-fold higher luciferase activity when compared with the vector-transfection control. When co-expressed with TRAF2, TR-11 induced greater luciferase activity than did TRAF2 alone. More importantly, overexpression of dominant-negative TRAF2, which lacked the RING and zinc finger motifs (Rothe, M., et al, *Science* 269:1421–1427 (1995)), abrogated the luciferase activity induced by TR-11. This indicates that TRAF2 is an important mediator of NF-κB activation for TR-11. A similar observation was made when the activity of NIK, which was thought to lie downstream of TRAF2 in the NF-κB signaling pathway, was blocked by overexpression of the dominant-negative NIK (Song, H. Y., et al, *Proc. Natl. Acad. Sci. USA* 94:9792–9796 (1997)), which lacked the two lysine residues of catalytic domain. Taken together, these data indicate that TR-11 mediates NF-κB activation through the TRAF2/NIK pathway. Since TRAF1 and TRAF3 were found to associate with TR-11 in HEK293 EBNA cells, the effects of TRAF1 and TRAF3 on NF-κB activation induced by TR-11 was examined. The introduction of TRAF3 nearly abolished the luciferase activity induced by TR-11 overexpression. To a lesser extent, TRAF1 overexpression diminished TR-11-induced NF-κB activation. These data suggest that TRAF1 and especially TRAF3 downregulate TR-11-induced NF-κB activation.

To identify TR-11 ligand, a panel of Flag-tagged candidate TNF ligand proteins for binding to TR-11-Fc fusion protein was screened by immunoprecipitation. TR-11-Fc selectively bound endokine-α-Flag among Flag-tagged TNF ligand proteins tested. In our experimental conditions, 4-1BB and TR2 (HVEM) bound their cognate ligands, 4-1BBL and LIGHT (Mauri, D. N., et al, *Immunity* 8:21–30 (1998)), respectively. Furthermore, this data clearly showed that endokine-α-Flag protein bound TR-11 transiently expressed on the cell surface of HEK293 EBNA cells and TR-11 constitutively expressed on the cell surface of Jurkat cell. Since endokine-α is a transmembrane protein (see below), flow cytometry to was used determine whether TR-11-Fc fusion protein was able to bind HEK293 EBNA cells that were stably transfected with full length endokine-α. The results demonstrate that TR-11-Fc protein was capable of binding endokine-α expressed on HEK293 EBNA cells.

Next, it was determined whether interactions between TR-11 and endokine-α would result in NF-κB activation. In an NF-κB reporter assay, ligand-dependent NF-κB activation was demonstrated by cotransfecting transmembrane endokine-α with TR-11 or transfecting endokine-a-expressing HEK293 EBNA cells. In addition, when TR-11 was transiently transfected into HEK293 EBNA cells which constitutively secreted soluble endokine-α protein, NF-κB activation markedly increased as compared to empty vector-transfected HEK293 EBNA cells. Similarly, higher NF-κB activation was induced by treating with soluble endokine-α protein HEK293 cells which were transiently transfected with TR-11. This indicates that endokine-α is able to trigger TR-11-specific activation of NF-κB. It appears that higher induction of NF-κB by endokine-α is correlated with a stronger association of TR-11 with TRAF2 in HEK293 EBNA cells, since stronger association of TR-11 with TRAF2 was observed in cells which were cotransfected with endokine-α than in cells which were transfected with TR-11 alone.

Endokine-α was one of the TNF ligand proteins initially identified by an EST database search. Hydrophilicity analysis of a full-length endokine-α clone from a brain cDNA library predicts a single hydrophobic transmembrane domain and the absence of a signal sequence. Endokine-α contains two potential glycosylation sites in the C-terminal region. These features suggest that endokine-α is a type II membrane protein with the C-terminal region extracellular. Northern blot analysis of human tissue RNAs revealed expression of a single 2.4-kb endokine-α mRNA in pancreas. Various human cell lines and PBMC were also examined for endokine-α expression. No message was detectable in either unstimulated or stimulated T-cell lines (CEM-6 and Jurkat), B-cell lines (Priess and Frev), promyelocytic cell line (HL-60), monocytic cell line (THP-1), and PBMC by RT-PCR. In contrast, HUVEC cells constitutively expressed endokine-α and its expression was upregulated after stimulation with LPS. Therefore, it is believed that TR-11 and its ligand are important for interactions between activated T lymphocytes and blood vessels.

TR-11 has 55% identity with murine GITR at the amino acid level. The high sequence conservation between human and mouse provides evidence that TR-11 is the human homologue of murine GITR. At this point, however, the possibility remains that these two receptors may serve distinct functions from one another, based on the following facts: (1) There is a mismatch in the first cysteine-rich pseudorepeat between GITR and TR-11; (2) in contrast to GITR, TR-11 is not inducible by dexamethasone.

In summary, a novel protein of the TNFR superfamily, TR-11, which activates NF-κB through a TRAF2-mediated mechanism has identified. Expression of TR-11 is activation-inducible. The ligand for TR-11, endokine-α, is a member of the TNF ligand family and is constitutively expressed in an endothelial cell line. This indicates that TR-11 and its ligand may be involved in activated T-cell trafficking.

Example 6

The Effects of Endokine Alpha on Monocytes

These studies disclose that treatment with endokine-α induced TNF-α, MCP-1, IL-8 and IL-10 release from monocytes and inhibited the production of IL-12 in monocytes. (data not shown).

Methods

Monocyte purification. Peripheral blood mononuclear cells (PBMC) were purified from single donor leukopacks (American Red Cross, Baltimore, Md.) by centrifugation through a Histopaque gradient (Sigma). Monocytes were isolated from PBMC by counterflow centrifugal elutriation.

ELISA. Human monocytes were incubated at a density of $5 \times 10^5$ cells/ml with increasing concentrations of endokine-α. For IL-12 production, the cells were primed overnight with IFN-γ (100 U/ml) in presence of Endokine-α. LPS (10 ng/ml) was then added. Conditioned media was collected after 24 h and kept frozen until use. ELISA kits for the measurement of TNF-α, IL-10, MCP-1 and IL-8 were purchased from R & D Systems (Minneapolis, Minn.). Each value was the mean of triplicate samples±standard deviation.

Oxidative burst. Purified monocytes were plated in 96-well plate at $2\text{-}1 \times 10^5$ cell/well. Increasing concentrations of Endokine-α are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) was added, together with the stimulant (200 nM PMA). The plates were incubated at 37° C. for 2 hours and the reaction was stopped by adding 20 μl 1N NaOH per well. The absorbance was read at 610 nm. To calculate the amount of $H_2O_2$ produced by the macrophages, a standard curve of a $H_2O_2$ solution of known molarity was done for each experiment.

| Effect of Endokine-a treatment on IL-12 secretion by monocytes | | |
|---|---|---|
| Treatment (mg/ml) | IL-12 (pg/ml) | Inhibition % |
| — | 513 | |
| TL-60.2 | 600 | 0 |
| TL-61 | 421 | 28 |
| TL-65 | 54 | 89 |

Monocytes ($5 \times 10^5$/ml) were incubated with IFN-g (100 U/ml) and TL-6. After 16 hours, LPS (10 ng/ml) was added to the cultures. Conditioned media was collected 24 hours following LPS addition and analyzed in ELISA for IL-12 content.

Example 7

Assays to Detect Stimulation or Inhibition of B cell Proliferation and Differentiation Background Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL5, IL6, IL-7, IL10, IL-13, IL14 and IL15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

Experimental Procedure

In vitro assay. Purified Endokine-α protein, or truncated forms thereof, is assessed for its ability to induce activation, proliferation, differentiation or inhibition and/or death in B-cell populations and their precursors. The activity of Endokine-α protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R (B220). Various dilutions of each sample are placed into individual wells of a 96-well plate to which are added $10^5$ B-cells suspended in culture medium (RPMI 1640 containing 10% FBS, $5 \times 10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with $^3$H-thymidine (6.7 Ci/mM) beginning 72 h post factor addition. The positive and negative controls are IL2 and medium respectively.

In vivo assay. BALB/c mice are injected (i.p.) twice per day with buffer only, or 2 mg/Kg of endokine-α protein, or truncated forms thereof. Mice receive this treatment for 4 consecutive days, at which time they are sacrificed and various tissues and serum collected for analyses. Comparison of H&E sections from normal and endokine-α protein-treated spleens identify the results of the activity of endokine-α protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from endokine-α protein-treated mice is used to indicate whether endokine-α protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and Endokine-α protein-treated mice.

Example 8

Assays to Detect Stimulation or Inhibition of T cell Proliferation and Differentiation The anti-CD3 and/or PHA costimulation assay is used to detected the stimulation or inhibition of T cell proliferation and differentiation.

Assay Parameters
Cells:
PBMC per well: $10^5$
PBMC recovered per donor: $200 \times 10^6$
Total plates per day: 20
Supernatants per plate: 48 (each assayed in duplicate)
Total supernatants per day per donor: 960 (two donors per day)
Need an additional 4 units of blood/week to accommodate new assay.
Reagents:
anti-human CD3 mAb (25 pg/mL final concentration in each well) PHA
rhIL-2 (positive control)
$^3$H-thymidine (0.5 $\mu$Ci/well, 6.7 Ci/mmole)
96-well plates
Protocol:
Purify PBMC.
Prepare plates with appropriate controls.
Incubate at 37° C. for 3–4 days.
Add $^3$H-TdR and return to incubator for an additional 20–24 hours.
Harvest and count.
Outcomes This assay allows the determination of whether Endokine-α enhances or inhibits anti-CD3-dependent proliferation of PBMCs and whether Endokine-α stimulates PBMC proliferation in the absence of costimulatory signals.

Example 9

Isolation of Antibody Fragments Directed Against Polypeptides of the Present Invention from a Library of ScFvs Naturally occuring V-genes isolated from human PBLs are constructed into a large library of antibody fragments which contain reactivities against polypeptides of the present invention to which the donor may or may not have been exposed (see e.g., U.S. Pat. No. 5,885,793 incorporated herein in its entirety by reference).

Rescue of the library. A library of scFvs is constructed from the RNA of human PBLs as described in WO92/01047. To rescue phage displaying antibody fragments, approximately $10^9$ *E. coli* harbouring the phagemid are used to inoculate 50 ml of 2xTY containing 1% glucose and 100 ug/ml of ampicillin (2xTY-AMP-GLU) and grown to an O.D. of 0.8 with shaking. Five ml of this culture is used to innoculate 50 ml of 2xTY-AMP-GLU. Next $2 \times 10^8$ TU of delta gene 3 helper phage (M13 delta gene III, see WO 92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the library. Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 10

Method of Determining Alterations in the Endokine Alpha Gene

RNA is isolated from entire families or individual patients presenting with a phenotype of interest (such as a disease). cDNA is then generated from these RNA samples using protocols known in the art. (see, Sambrook.) The cDNA is then used as a template for PCR, employing primers surrounding regions of interest in SEQ ID NO:1. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase (Epicentre Technologies). The intron-exon borders of selected exons of endokine alpha are also determined and genomic PCR products analyzed to confirm the results. PCR products harboring suspected mutations in endokine alpha are then cloned and sequenced to validate the results of the direct sequencing.

PCR products of endokine alpha are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in endokine alpha not present in unaffected individuals.

Genomic rearrangements are also observed as a method of determining alterations in the endokine alpha gene. Genomic clones isolated using techniques known in the art are nick-translated with digoxigenindeoxy-uridine 5'-triphosphate (Boehringer Manheim), and FISH performed as described in Johnson, C. G. et al., Methods Cell Biol. 35:73–99 (1991). Hybridization with the labeled probe is carried out using a vast excess of human cot-1 DNA for specific hybridization to the endokine alpha genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, C. V. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of endokine alpha (hybridized by the probe) are identified as insertions, deletions, and translocations. These endokine alpha alterations are used as a diagnostic marker for an associated disease.

Example 11

Method of Detecting Abnormal Levels of Endokine Alpha in a Biological Sample Endokine alpha polypeptides can be detected in a biological sample, and if an increased or decreased level of endokine alpha is detected, this polypeptide is a marker for a particular phenotype. Methods of detection are numerous, and thus, it is understood that one skilled in the art can modify the following assay to fit their particular needs.

For example, antibody-sandwich ELISAs are used to detect endokine alpha in a sample, preferably a biological sample. Wells of a microtiter plate are coated with specific antibodies to endokine alpha, at a final concentration of 0.2 to 10 ug/ml. The antibodies are either monoclonal or polyclonal and are produced using technique known in the art. The wells are blocked so that non-specific binding of endokine alpha to the well is reduced.

The coated wells are then incubated for >2 hours at RT with a sample containing endokine alpha. Preferably, serial dilutions of the sample should be used to validate results.

The plates are then washed three times with deionized or distilled water to remove unbounded endokine alpha.

Next, 50 µl of specific antibody-alkaline phosphatase conjugate, at a concentration of 25–400 ng, is added and incubated for 2 hours at room temperature. The plates are again washed three times with deionized or distilled water to remove unbounded conjugate.

Seventy-five ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is preparded using the experimental results from serial dilutions of a control sample with the sample concentration plotted on the X-axis (log scale) and fluorescence or absorbance on the Y-axis (linear scale). The endokine alpha polypeptide concentration in a sample is then interpolated using the standard curve based on the measured flourescence of that sample.

Example 12

Method of Treating Decreased Levels of Endokine Alpha

The present invention also relates to a method for treating an individual in need of an increased level of endokine alpha biological activity in the body comprising administering to such an individual a composition comprising a therapeutically effective amount of endokine alpha or an agonist thereof.

Moreover, it will be appreciated that conditions caused by a decrease in the standard or normal expression level of endokine alpha in an individual can be treated by administering endokine alpha, preferably in a soluble and/or secreted form. Thus, the invention also provides a method of treatment of an individual in need of an increased level of endokine alpha polypeptide comprising administering to such an individual apharmaceutical composition comprising an amount of endokine alpha to increase the biological activity level of endokine alpha in such an individual.

For example, a patient with decreased levels of endokine alpha polypeptide receives a daily dose 0.1–100 µg/kg of the polypeptide for six consecutive days. Preferably, the polypeptide is in a soluble and/or secreted form.

Example 13

Method of Treating Increased Levels of Endokine Alpha

The present invention relates to a method for treating an individual in need of a decreased level of endokine alpha biological activity in the body comprising, administering to such an individual a composition comprising a therapeutically effective amount of endokine alpha antagonist. Preferred antagonists for use in the present invention are endokine alpha-specific antibodies or endokine alpha antisense polynucleotides.

Antisense technology is used to inhibit production of endokine alpha. This technology is one example of a method of decreasing levels of endokine alpha polypeptide, preferably a soluble and/or secreted form, due to a variety of etiologies, such as cancer.

For example, a patient diagnosed with abnormally increased levels of endokine alpha is administered intravenously antisense polynucleotides at 0.5, 1.0, 1.5, 2.0 and 3.0 mg/kg day for 21 days. This treatment is repeated after a 7-day rest period if the is determined to be well tolerated.

Example 14

Method of Treatment Using Gene Therapy—Ex vivo

One method of gene therapy transplants fibroblasts, which are capable of expressing soluble and/or mature endokine alpha polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted; the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA* 7:219–25 (1988)), flanked by the long terminal repeats of the Moloney murine sarcoma virus, is digested with EcoRI and HindIII and subsequently treated with calfintestinal phosphatase. The linear vector is fractionated on agarose gel and purified, using glass beads.

The cDNA encoding endokine alpha can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanarnycin for the purpose of confirming that the vector contains properly inserted endokine alpha.

The amphotropic pA317 or GP+am 12 packaging cells are grown in tissue culture to confluent density in Dulbecco's Modified Eagles Medium (DMEM) with 10% calf serum (CS), penicillin and streptomycin. The MSV vector containing the endokine alpha gene is then added to the media and the packaging cells transduced with the vector. The packaging cells now produce infectious viral particles containing the endokine alpha gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether endokine alpha protein is produced.

The engineered fibroblasts are then transplanted onto the host, either alone or after having been grown to confluence on cytodex 3 microcarrier beads.

Example 15

Method of Treatment Using Gene Therapy—In vivo

Another aspect of the present invention is using in vivo gene therapy methods to treat disorders, diseases and conditions. The gene therapy method relates to the introduction of naked nucleic acid (DNA, RNA, and antisense DNA or RNA) endokine alpha sequences into an animal to increase or decrease the expression of the endokine alpha polypeptide. The endokine alpha polynucleotide may be operatively linked to a promoter or any other genetic elements necessary for the expression of the endokine alpha polypeptide by the target tissue. Such gene therapy and delivery techniques and methods are known in the art, see, for example, WO 90/11092, WO 98/11779; U.S. Pat. Nos. 5,693,622, 5,705, 151, 5,580,859; Tabata H. et al., *Cardiovasc. Res.* 35:470–479 (1997); Chao J. et al., *Pharmacol. Res.* 35:517–522(1997); Wolff J. A. *Neuromuscul. Disord.* 7:314–318 (1997); Schwartz B. et al., *Gene Ther.* 3:405–411 (1996); Tsurumi Y. et al., *Circulation* 94:3281–3290 (1996) (incorporated herein by reference).

The endokine alpha polynucleotide constructs may be delivered by any method that delivers injectable materials to the cells of an animal, such as, injection into the interstitial space of tissues (heart, muscle, skin, lung, liver, intestine and the like). The endokine alpha polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the endokine alpha polynucleotides may also be delivered in liposome formulations (such as those taught in Felgner P. L. et al. *Ann. NY Acad. Sci.* 772:126–139 (1995), and Abdallah B. et al. *Biol. Cell* 85:1–7 (1995)) which can be prepared by methods well known to those skilled in the art.

The endokine alpha polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The endokine alpha polynucleotide construct can be delivered to the interstitial space of tissues within an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked endokine alpha polynucleotide injection, an effective dosage amount of DNA or RNA will be in the range of from about 0.05 $\mu$g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked endokine alpha polynucleotide constructs can be delivered to arteries during angioplasty by the catheter used in the procedure.

The dose response effects of injected endokine alpha polynucleotide in muscle in vivo are determined as follows. Suitable endokine alpha template DNA for production of mRNA coding for endokine alpha polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The endokine alpha template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 $\mu$m cross-section of the individual quadriceps muscles is histochemically stained for endokine alpha protein. A time course for endokine alpha protein expression may be done in a similar fashion except that quadriceps from different mice are harvested at different times. Persistence of endokine alpha DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using endokine alpha naked DNA.

Example 16

Gene Therapy Using Endogenous Endokine Alpha Gene

Another method of gene therapy according to the present invention involves operably associating the endogenous endokine alpha sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., *Proc. Natl. Acad. Sci. USA* 86:8932–8935 (1989); and Zijlstra et al., *Nature* 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous endokine alpha, flanking the promoter. The targeting sequence will be sufficiently near the 5' end of endokine alpha so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides viaelectroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous endokine alpha sequence. This results in the expression of endokine alpha in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are again centrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the endokine alpha locus, plasmid pUC18 (MBI Fermentas, Amherst, N.Y.) is digested with HindIII. The CMV promoter is amplified by PCR with an XbaI site on the 5' end and a BamHI site on the 3' end. Two endokine alpha non-coding sequences are amplified via PCR; one endokine alpha non-coding sequence (endokine alpha fragment 1) is amplified with a HindIII site at the 5' end and an Xba site at the 3' end; the other endokine alpha non-coding sequence (endokine alpha fragment 2) is amplified with a BamHI site at the 5' end and a HindIII site at the 3' end. The CMV promoter and endokine alpha fragments are digested with the appropriate enzymes (CMV promoter—XbaI and BamHI; endokine alpha fragment 1—XbaI; endokine alpha fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 $\mu$g/ml. 0.5 ml of the cell suspension (containing approximately $1-5\times10^6$ cells) is then added to the cuvette, and the cell suspension and DNA solutions are gently mixed. Electroporation is performed with a Gene-Pulser apparatus (Bio-Rad). Capacitance and voltage are set at 960 $\mu$F and 250–300 V, respectively. As voltage increases, cell survival decreases, but the percentage of surviving cells that stably incorporate the introduced DNA into their genome increases dramatically. Given these parameters, a pulse time of approximately 14–20 msec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and the cells are incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 17

Effect of Endokine Alpha on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-$\alpha$, causes a rapid change in surface phenotype (increased expression of MHC class I and II, costimulatory and adhesion molecules, downregulation of FC$\gamma$II, upregulation of CD83). These changes correlate with increased antigen-presenting capacity and with functional maturation of the dendritic cells.

FACS analysis of surface antigens is performed as follows. Cells are treated 1–3 days with increasing concentrations of endokine alpha or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines. Cytokines generated by dendritic cells, in particular IL-12, are important, in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells (106/ml) are treated with increasing concentrations of endokine alpha for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of endokine alpha or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease ionocyte survival) are known in the art and may routinely be applied to determine whether a molecule of the invention functions as an inhibitor or activator of monocytes. Endokine alpha, agonists, or antagonists of endokine alpha can be screened using the three assays described below. For each of these assays, peripheral blood mononuclear cells (PBMC) are purified from single donor leuko-packs (American Red Cross, Baltimore, Md.) by centrifugation through a Histopaque gradient (Sigma). Monocytes are isolated from PBMC by counterflow centrifugal elutriation.

1. Monocyte Survival Assay. Human peripheral blood monocytes progressively lose viability when cultured in absence of serum or other stimuli. Their death results from an internally regulated process (apoptosis). Addition to the culture of activating factors, such as TNF-alpha, dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 µg/ml, and then incubated at room temperature for 5 minutes before FAC Scan analysis. PI uptake has been demonstrated to correlate with DNA fragmentation in this experimental paradigm.

2. Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of endokine alpha or in the absence of endokine alpha. For IL-12 production, the cells are primed overnight with IFN-γ (100 U/ml) in presence of endokine alpha. LPS (10 ng/ml) is then added. Conditioned media is collected after 24 h and kept frozen until use. Measurement of TNF-α, IL-10, MCP-1 and IL-8 is then performed using a commercially available ELISA kit (e.g., R & D Systems (Minneapolis, Minn.)) applying the standard protocols provided with the kit.

3. Oxidative burst. Purified monocytes are plated in 96-well plates at $2-1\times10^5$ cell/well. Increasing concentrations of endokine alpha are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 µl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in endokine alphaprotein. However, one skilled in the art could easily modify the exemplified studies to test the activity of endokine alpha polynucleotides (e.g., gene therapy), agonists, and/or antagonists of endokine alpha.

Example 18

Assay to Detect Stimulation or Inhibition of T Cell Proliferation

A CD3-induced proliferation assay is performed on PBMCs and is measured by the uptake of $^3$H-thymidine. The assay is performed as follows. Ninety-six well plates are coated with 100 µl/well of mAb to CD3 (HIT3a, Pharmingen) or isotype-matched control mAb (B33.1) overnight at 4° C. (1 µg/ml in 0.05 M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of endokine alpha protein (total volume 200 µl). Relevant protein buffer and medium alone are controls. After 48 hour culture at 37° C., plates are spun for 2 min. at 1000 rpm and 100 µl of supernatant is removed and stored −20° C. for measurement of IL-2 (or other cytokines) if effect on proliferation is observed. Wells are supplemented with 100 µl of medium containing 0.5 µCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100

U/ml) is also used as a control which enhances proliferation. Control antibody which does not induce proliferation of T cells is used as the negative controls for the effects of endokine alpha proteins.

The studies described in this example tested activity in endokine alpha protein. However, one skilled in the art could easily modify the exemplified studies to test the activity of endokine alpha polynucleotides (e.g., gene therapy), agonists, and/or antagonists of endokine alpha.

Example 19

Production of an Antibody a) Hybridoma Technology

The antibodies of the present invention can be prepared by a variety of methods. (see, Current Protocols, Chapter 2.) As one example of such methods, cells expressing Endokine alpha are administered to an animal to induce the production of sera containing polyclonal antibodies. In a preferred method, a preparation of Endokine alpha protein is prepared and purified to render it substantially free of natural contaminants. Such a preparation is then introduced into an animal in order to produce polyclonal antisera of greater specific activity.

Monoclonal antibodies specific for protein Endokine alpha are prepared using hybridoma technology. (Kohler et al., *Nature* 256:495 (1975); Kohler et al., *Eur. J. Immunol.* 6:511 (1976); Kohler et al., *Eur. J. Immunol.* 6:292 (1976); Hammerling et al., in: *Monoclonal Antibodies and T-Cell Hybridomas*, Elsevier, N.Y., pp. 563–681 (1981)). In general, an animal (preferably a mouse) is immunized with Endokine alpha polypeptide or, more preferably, with a secreted Endokine alpha polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the Endokine alpha polypeptide.

Alternatively, additional antibodies capable of binding to Endokine alpha polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the Endokine alpha protein-specific antibody can be blocked by Endokine alpha. Such antibodies comprise anti-idiotypic antibodies to the Endokine alpha protein-specific antibody and are used to immunize an animal to induce formation of further Endokine alpha protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (see, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).)

b) Isolation Of Antibody Fragments Directed Against Endokine alpha From A Library Of scFvs Naturally occurring V-genes isolated from human PBLs are constructed. into a library of antibody fragments which contain reactivities against Endokine alpha to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 μg/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 ug ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/mi or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6.

Clones positive in ELISA are further characterized by PCR fingerprinting (see, e.g., PCT publication WO 92/01047) and then by sequencing.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference.

What is claimed is:

1. An isolated antibody, which specifically binds the protein of SEQ ID NO: 2.

2. The antibody of claim 1, which specifically binds a protein of 30 contiguous amino acids of SEQ ID NO:2.

3. The antibody of claim 2, which specifically binds a protein of 15 contiguous amino acids of SEQ ID NO:2.

4. The antibody of claim 1, which specifically binds the protein of amino acids 44 to 158 of SEQ ID NO:2.

5. The antibody of claim 1, which specifically binds the protein of amino acids 44 to 54 of SEQ ID NO:2.

6. The antibody of claim 1, which specifically binds the protein of amino acids 57 to 68 of SEQ ID NO:2.

7. The antibody of claim 1, which specifically binds the protein of amino acids 69 to 78 of SEQ ID NO:2.

8. The antibody of claim 1, which specifically binds the protein of amino acids 94 to 105 of SEQ ID NO:2.

9. The antibody of claim 1, which specifically binds the protein of amino acids 108 to 132 of SEQ ID NO:2.

10. The antibody of claim 1, which specifically binds the protein of amino acids 148 to 158 of SEQ ID NO:2.

11. The antibody of claim 1, wherein said antibody is polyclonal.

12. The antibody of claim 1, wherein said antibody is monoclonal.

13. The antibody of claim 1, wherein said antibody is chimeric.

14. The antibody of claim 1, wherein said antibody is humanized.

15. A composition comprising the antibody of claim 1 and a carrier.

16. A method of producing the antibody of claim 1 comprising:
   (a) immunizing an animal with a protein comprising 15 contiguous amino acids of SEQ ID NO: 2; and
   (b) recovering said antibody.

17. A method of detecting the protein of SEQ ID NO: 2 in a biological sample comprising:
   (a) contacting a biological sample with the antibody of claim 1; and
   (b) determining the presence or absence of said protein in said biological sample.

18. An isolated antibody fragment, which specifically binds the protein of SEQ ID NO: 2.

19. The antibody fragment of claim 18, which specifically binds a protein of 30 contiguous amino acids of SEQ ID NO:2.

20. The antibody fragment of claim 19, which specifically binds a protein of 15 contiguous amino acids of SEQ ID NO:2.

21. The antibody fragment of claim 18, which specifically binds the protein of amino acids 44 to 158 of SEQ ID NO:2.

22. The antibody fragment of claim 18, which specifically binds the protein of amino acids 44 to 54 of SEQ ID NO:2.

23. The antibody fragment of claim 18, which specifically binds the protein of amino acids 57 to 68 of SEQ ID NO:2.

24. The antibody fragment of claim 18, which specifically binds the protein of amino acids 69 to 78 of SEQ ID NO:2.

25. The antibody fragment of claim 18, which specifically binds the protein of amino acids 94 to 105 of SEQ ID NO:2.

26. The antibody fragment of claim 18, which specifically binds the protein of amino acids 108 to 132 of SEQ ID NO:2.

27. The antibody fragment of claim 18, which specifically binds the protein of amino acids 148 to 158 of SEQ ID NO:2.

28. The antibody fragment of claim 18, wherein said antibody fragment comprises a Fab fragment.

29. The antibody fragment of claim 18, wherein said antibody fragment comprises a single chain antibody.

30. The antibody fragment of claim 18, wherein said antibody fragment comprises a Fvs antibody.

31. The antibody fragment of claim 18, wherein said antibody fragment is chimeric.

32. The antibody fragment of claim 18, wherein said antibody fragment is humanized.

33. A composition comprising the antibody fragment of claim 18 and a carrier.

34. A method of detecting the protein of SEQ ID NO: 2 in a biological sample comprising:
   (a) contacting a biological sample with the antibody fragment of claim 18; and
   (b) determining the presence or absence of said protein in said biological sample.

35. An isolated antibody, which specifically binds the protein encoded by ATCC Deposit No. 97640.

36. The antibody of claim 35, which specifically binds the mature protein encoded by ATCC Deposit No. 97640.

37. The antibody of claim 35, which specifically binds a protein of 30 contiguous amino acids encoded by ATCC Deposit No. 97640.

38. The antibody of claim 37, which specifically binds a protein of 15 contiguous amino acids encoded by ATCC Deposit No. 97640.

39. The antibody of claim 35, wherein said antibody is polyclonal.

40. The antibody of claim 35, wherein said antibody is monoclonal.

41. The antibody of claim 35, wherein said antibody is chimeric.

42. The antibody of claim 35, wherein said antibody is humanized.

43. A composition comprising the antibody of claim 35 and a carrier.

44. A method of producing the antibody of claim 35 comprising:
   (a) immunizing an animal with a protein comprising 15 contiguous amino acids of the polypeptide encoded by ATCC Deposit No. 97640; and
   (b) recovering said antibody.

45. A method of detecting the protein encoded by ATCC Deposit No. 97640 in a biological sample comprising:
   (a) contacting a biological sample with the antibody of claim 35; and
   (b) determining the presence or absence of said protein in said biological sample.

46. An isolated antibody fragment, which specifically binds the protein encoded by ATCC Deposit No. 97640.

47. The antibody fragment of claim 46, which specifically binds the mature protein encoded by ATCC Deposit No. 97640.

48. The antibody fragment of claim 46, which specifically binds a protein of 30 contiguous amino acids encoded by ATCC Deposit No. 97640.

49. The antibody fragment of claim 48, which specifically binds a protein of 15 contiguous amino acids encoded by ATCC Deposit No. 97640.

50. The antibody fragment of claim 46, wherein said antibody fragment comprises a Fab fragment.

51. The antibody fragment of claim 46, wherein said antibody fragment comprises a single chain antibody.

52. The antibody fragment of claim 46, wherein said antibody fragment comprises a Fvs antibody.

53. The antibody fragment of claim 46, wherein said antibody fragment is chimeric.

54. The antibody fragment of claim 46, wherein said antibody fragment is humanized.

55. A composition comprising the antibody fragment of claim 46 and a carrier.

56. A method of detecting the protein encoded by ATCC Deposit No. 97640 in a biological sample comprising:
   (a) contacting a biological sample with the antibody fragment of claim 46, and
   (b) determining the presence or absence of said protein in said biological sample.

* * * * *

UNITED STATES PATENT AND TRADEMARK OFFICE
CERTIFICATE OF CORRECTION

PATENT NO.     : 6,406,867 B1
DATED          : June 18, 2002
INVENTOR(S)    : Yu et al.

It is certified that error appears in the above-identified patent and that said Letters Patent is hereby corrected as shown below:

<u>Title page,</u>
Item [54], delete "ANTIBODY TO HUMAN ENDOKINE ALPHA AND METHODS OF USE" and insert therein -- HUMAN ENDOKINE ALPHA ANTIBODIES --.

Signed and Sealed this

Tenth Day of September, 2002

Attest:

Attesting Officer

JAMES E. ROGAN
*Director of the United States Patent and Trademark Office*